(12) United States Patent
Shapiro

(10) Patent No.: US 10,221,182 B2
(45) Date of Patent: Mar. 5, 2019

(54) 3,3-DIFLUORO-PIPERIDINE DERIVATIVES AS NR2B NMDA RECEPTOR ANTAGONISTS

(71) Applicant: Rugen Holdings (Cayman) Limited, Grand Cayman (KY)

(72) Inventor: Gideon Shapiro, Gainesville, FL (US)

(73) Assignee: RUGEN HOLDINGS (CAYMAN) LIMITED, Grand Cayman (KY)

( * ) Notice: Subject to any disclaimer, the term of this patent is extended or adjusted under 35 U.S.C. 154(b) by 0 days.

(21) Appl. No.: 15/548,594

(22) PCT Filed: Feb. 3, 2016

(86) PCT No.: PCT/US2016/016442
§ 371 (c)(1),
(2) Date: Aug. 3, 2017

(87) PCT Pub. No.: WO2016/126869
PCT Pub. Date: Aug. 11, 2016

(65) Prior Publication Data
US 2018/0030055 A1      Feb. 1, 2018

Related U.S. Application Data

(60) Provisional application No. 62/111,967, filed on Feb. 4, 2015.

(51) Int. Cl.
| | | |
|---|---|---|
| C07D 487/04 | (2006.01) | |
| A61K 31/55 | (2006.01) | |
| A61P 25/00 | (2006.01) | |
| A61P 25/24 | (2006.01) | |
| A61P 25/28 | (2006.01) | |
| A61P 25/08 | (2006.01) | |

(52) U.S. Cl.
CPC ........... *C07D 487/04* (2013.01); *A61P 25/00* (2018.01); *A61P 25/08* (2018.01); *A61P 25/24* (2018.01); *A61P 25/28* (2018.01)

(58) Field of Classification Search
None
See application file for complete search history.

(56) References Cited

U.S. PATENT DOCUMENTS

| | | | |
|---|---|---|---|
| 6,008,233 | A | 12/1999 | Andino et al. |
| 7,592,360 | B2 | 9/2009 | Liverton et al. |
| 9,567,341 | B2 | 2/2017 | Shapiro |
| 9,968,610 | B2 * | 5/2018 | Shapiro ................. A61K 9/0053 |
| 10,030,026 | B2 | 7/2018 | Shapiro |
| 2007/0293515 | A1 | 12/2007 | Layton et al. |
| 2009/0062261 | A1 | 3/2009 | Masui et al. |
| 2010/0105650 | A1 | 4/2010 | Plettenburg et al. |
| 2011/0280808 | A1 | 11/2011 | Kroth et al. |
| 2013/0096115 | A1 | 4/2013 | Lichter et al. |
| 2013/0225575 | A1 | 8/2013 | Lichter et al. |
| 2013/0231348 | A1 | 9/2013 | Campbell et al. |
| 2014/0018348 | A1 | 1/2014 | Javitt |
| 2014/0336185 | A1 | 11/2014 | Boehm et al. |
| 2016/0075713 | A1 | 3/2016 | Shapiro |
| 2017/0101412 | A1 | 4/2017 | Shapiro |
| 2017/0209449 | A1 | 7/2017 | Shapiro |
| 2018/0170935 | A1 | 6/2018 | Shapiro |

FOREIGN PATENT DOCUMENTS

| | | | |
|---|---|---|---|
| CN | 1503793 | A | 6/2004 |
| CN | 101163482 | A | 4/2008 |
| EP | 3194403 | A1 | 7/2017 |
| WO | WO-02068409 | A1 | 9/2002 |
| WO | WO-2004/108705 | A1 | 12/2004 |
| WO | WO-2005/102390 | A2 | 11/2005 |
| WO | WO-2006/113471 | A2 | 10/2006 |
| WO | WO-2007/061868 | A2 | 5/2007 |

(Continued)

OTHER PUBLICATIONS

International Search Report for PCT/US2016/016442, 3 pages (dated Apr. 8, 2016).
Written Opinion for PCT/US2016/016442, 9 pages (dated Apr. 8, 2016).
U.S. Appl. No. 15/513,112, filed Mar. 21, 2017, Liu et al.
U.S. Appl. No. 15/961,553, filed Apr. 24, 2018, Shapiro et al.
U.S. Appl. No. 16/100,596, filed Aug. 10, 2018, Shapiro et al.
Addy, C. et al., Single-dose administration of MK-0657, an NR2B-selective NMDA antagonist, does not result in clinically meaningful improvement in motor function in patients with moderate Parkinson's disease, J Clin Pharmacol, 49(7):856-864 (2009).

(Continued)

*Primary Examiner* — Zinna Northington Davis
(74) *Attorney, Agent, or Firm* — Choate, Hall & Stewart LLP; Brenda Herschbach Jarrell; Kristen C. Buteau

(57) ABSTRACT

Disclosed are chemical entities of Formula (I): wherein X, Y, Z, $R^1$, $R^3$, $R^4$ and $R^5$ are defined herein, as NR2B subtype selective receptor antagonists. Also disclosed are pharmaceutical compositions comprising a chemical entity of Formula (I), and methods of treating various diseases and disorders associated with NR2B antagonism, e.g., diseases and disorders of the CNS, such as depression, by administering a chemical entity of Formula (I).

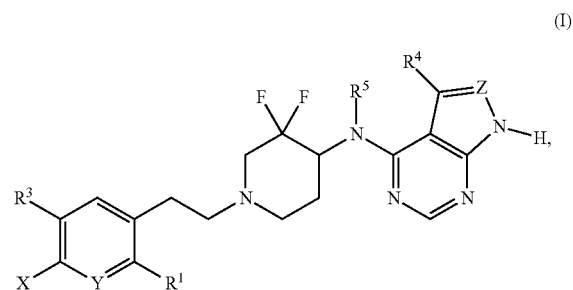

(I)

19 Claims, 1 Drawing Sheet

(56) References Cited

FOREIGN PATENT DOCUMENTS

| WO | WO-2010/015637 A1 | 2/2010 |
|---|---|---|
| WO | WO-2012/123312 A1 | 9/2012 |
| WO | WO-2014/120800 A1 | 8/2014 |
| WO | WO-2015/171770 A1 | 11/2015 |
| WO | WO-2015/187845 A1 | 12/2015 |
| WO | WO-2016/044323 A1 | 3/2016 |
| WO | WO-2016/049048 A1 | 3/2016 |
| WO | WO-2016/100349 A2 | 6/2016 |
| WO | WO-2016/126869 A1 | 8/2016 |
| WO | WO-2016/196513 A1 | 12/2016 |
| WO | WO-2018/098128 A1 | 5/2018 |

OTHER PUBLICATIONS

Ayata, C. et al., Suppression of cortical spreading depression in migraine prophylaxi, Ann Neurol, 59(4):652-661 (2006).
Bandyopadhyay, S. and Hablitz, J., NR2B antagonists restrict spatiotemporal spread of activity in a rat model of cortical dysplasia, Epilepsy Research, 72:127-139 (2006).
Barton, M. et al., Pharmacological characterization of the 6 Hz psychomotor seizure model of partial epilepsy, Epilepsy Res, 47(3):217-227 (2001).
Bausch, S. et al., Inverse relationship between seizure expression and extrasynaptic NMDAR function following chronic NMDAR inhibition, Epilepsia, 51(Suppl 3):102-105 (2010).
Beinat, C. et al., Insights into Structure-Activity Relationships and CNS Therapeutic Applications of NR2B Selective Antagonists, Current Medicinal Chemistry, 17:4166-4190 (2010).
Berge, S. et al., Pharmaceutical salts, J Pharm Sci, 66(1):1-19 (1977).
Bezzard et al., Neuroscience Disease Models, Neuroscience, 211:1 (2012).
Bogdanova, O. et al., Factors influencing behavior in the forced swim test, Physiol Behav, 118:227-239 (2013).
Borza, I. and Domany, G., NR2B selective NMDA antagonists: the evolution of the ifenprodil-type pharmacophore, Curr Top Med Chem, 6(7):687-695 (2006).
Boyce-Rustay, J.M. and Holmes, A., Functional Roles of NMDA Receptor NR2A and NR2B Subunits in the Acute Intoxicating Effects of Ethanol in Mice, Synapse, 56:222-225 (2005).
Brown, D. et al., 2,6-Disubstituted pyrazines and related analogs as NR2B site antagonists of the NMDA receptor with anti-depressant activity, Bioorg Med Chem Lett, 21(11):3399-3403 (2011).
Brown, W. et al., Comparative assay of an antiepileptic drugs by psychomotor seizure test and minimal electroshock threshold test, J Pharmacol Exp Ther, 107(3):273-283 (1953).
Can, A. et al., The mouse forced swim test, J Vis Exp, (59):e3638 (2012).
Castel-Branco, M. et al., The maximal electroshock seizure (MES) model in the preclinical assessment of potential new antiepileptic drugs, Methods Find Exp Clin Pharmacol, 31(2):101-106 (2009).
Chen, M. et al., Differential Roles of NMDA Receptor Subtypes in Ischemic Neuronal Cell Death and Ischemic Tolerance, Stroke, 39:3042-3048 (2008).
Chenard, B. et al., (1S,2S)-1-(4-hydroxyphenyl)-2-(4-hydroxy-4-phenylpiperidino)-1-propanol: a potent new neuroprotectant which blocks N-methyl-D-aspartate responses, J Med Chem, 38(16):3138-3145 (1995).
Chermat and Simon, Fiche Technique, Journal of Pharmacology, 6:494-496 (1975).
Claiborne, C. et al., Orally efficacious NR2B-selective NMDA receptor antagonists, Bioorg Med Chem Lett, 13(4):697-700 (2003).
Cull-Candy, S. et al., NMDA receptor diversity in the cerebellum: identification of subunits contributing to functional receptors, Neuropharmacology, 37(10-11):1369-1380 (1998).
Curran, H. and Morgan, C., Cognitive, dissociative and psychotogenic effects of ketamine in recreational users on the night of drug use and 3 days later, Addiction, 95(4):575-590 (2000).

Curtis, N. et al., Novel N1-(benzyl)cinnamamidine derived NR2B subtype-selective NMDA receptor antagonists, Bioorg Med Chem Lett, 13(4):693-696 (2003).
Dalby, N. and Nielsen, E., Comparison of the preclinical anticonvulsant profiles of tiagabine, lamotrigine, gabapentin and vigabatrin, Epilepsy Res, 28(1):63-72 (1997).
Damasio, Antonio R., Alzheimer's Disease and Related Dementias, Cecil Textbook of Medicine, 20th Edition, 2:1992-1996 (1996).
Dubuisson, D. and Dennis, S., The formalin test: a quantitative study of the analgesic effects of morphine, meperidine, and brain stem stimulation in rats and cats, Pain, 4(2):161-74 (1977).
Duman, C., Models of depression, Vitam Horm, 82:1-21 (2010).
Esneault, E. et al., Evaluation of pro-convulsant risk in the rat: spontaneous and provoked convulsions, J Pharmacol Toxicol Methods, 72:59-66 (2015).
Fischer, G. et al., Ro 25-6981, a highly potent and selective blocker of N-methyl-D-aspartate receptors containing the NR2B subunit, Characterization in vitro, J Pharmacol Exp Ther, 283(3):1285-1292 (1997).
Fisher, R. et al., Epileptic seizures and epilepsy: definitions proposed by the International League Against Epilepsy (ILAE) and the International Bureau for Epilepsy (IBE), Epilepsia, 46(4):470-472 (2005).
Garner, R. et al., Preclinical pharmacology and pharmacokinetics of CERC-301, a GluN2B-selective N-methyl-D-aspartate receptor antagonist, Pharmacology Research & Perspectives, 3(6):e00198 (2015).
Ghasemi, M. and Schachter, S.C., The NMDA receptor complex as a therapeutic target in epilepsy: a review, Epilepsy & Behavior, 22:617-640 (2011).
Giannini, A. James et al., Phencyclidine and the Dissociativese, Psychiatric Medicine, 3:197-217 (1985).
Haas, D. and Harper, D., Ketamine: a review of its pharmacologic properties and use in ambulatory anesthesia, Anesth Prog, 39(3):61-68 (1992).
Hancox, J. and James, A., Refining insights into high-affinity drug binding to the human ether-à-go-go-related gene potassium channel, Mol Pharmacol, 73(6):1592-1595 (2008).
Hansen, K. et al., Pharmacological characterization of ligands at recombinant NMDA receptor subtypes by electrophysiological recordings and intracellular calcium measurements, Comb Chem High Throughput Screen, 11(4):304-315 (2008).
Hardy, J. et al., Randomized, double-blind, placebo-controlled study to assess the efficacy and toxicity of subcutaneous ketamine in the management of cancer pain, J Clin Oncol, 30(29):3611-3617 (2012).
Hooft, R. et al., Determination of absolute structure using Bayesian statistics on Bijvoet differences, J Appl Crystallogr, 41(Pt 1):96-103 (2008).
Ibrahim, L. et al., Randomized, placebo-controlled, crossover pilot trial of the oral selective NR2B antagonist MK-0657 in patients with treatment-resistant major depressive disorder, J Clin Psychopharmacol, 32(4):551-557 (2012).
International Search Report for PCT/US2015/034009, 3 pages (dated Sep. 30, 2015).
International Search Report for PCT/US2015/050267, 4 pages (dated Dec. 9, 2015).
International Search Report for PCT/US2015/051488, 4 pages (dated Jan. 27, 2016).
International Search Report for PCT/US2016/35098, 3 pages (dated Aug. 31, 2016).
International Search Report for PCT/US2017/062726 (Treatment of Autism Spectrum Disorders, Obsessive-Compulsive Disorder and Anxiety Disorders, filed Nov. 21, 2017), issued by ISA/EP, 7 pages (dated Apr. 3, 2018).
Jimenez-Sanchez, L. et al., The Role of GluN2A and GluN2B Subunits on the Effect of NMDA Receptor Antagonists in Modeling Schizophrenia and Treating Refractory Depression, Neuropsychopharmacology, 39:2673-2680 (2014).
Jordan, V. Craig, Tamoxifen: A Most Unlikely Pioneering Medicine, Nature Reviews: Drug Discovery, 2(3):205-213 (2003).
Kao, J. et al., NR2B subunit of NMDA receptor at nucleus accumbens is involved in morphine rewarding effect by siRNA study, Drug and Alcohol Dependence, 118:366-374 (2011).

(56) References Cited

OTHER PUBLICATIONS

Katalinic, N. et al., Ketamine as a new treatment for depression: a review of its efficacy and adverse effects, Aust N Z J Psychiatry, 47(8):710-727 (2013).
Kawai, M. et al., Discovery of novel and orally active NR2B-selective N-methyl-D-aspartate (NMDA) antagonists, pyridinol derivatives with reduced HERG binding affinity, Bioorg Med Chem Lett, 17(20):5533-5536 (2007).
Khisti, R. et al., Haloperidol-induced catalepsy: a model for screening antidepressants effective in treatment of depression with Parkinson's disease, Indian J Exp Biol, 35(12):1297-1301 (1997).
Kiss, L. et al., In vitro characterization of novel NR2B selective NMDA receptor antagonists, Neurochem Int, 46(6):453-464 (2005).
Kong, M. et al., NR2B antagonist CP-101,606 inhibits NR2B phosphorylation at tyrosine-1472 and its interactions with Fyn in levodopa-induced dyskinesia rat model, Behavioural Brain Research, 282:46-53 (2015).
Konitsiotis, S. et al., Effects of N-methyl-D-aspartate receptor antagonism on neuroleptic-indeuced orofacial dyskinesias, Physchopharmacology, 185:369-377 (2006).
Koudih, R. et al., Synthesis and in vitro characterization of trans- and cis-[(18)F]-4-methylbenzyl 4-[(pyrimidin-2-ylamino)methyl]-3-fluoropiperidine-1-carboxylates as new potential PET radiotracer candidates for the NR2B subtype N-methyl-D-aspartate receptor, Eur J Med Chem, 53:408-415 (2012).
Krall, R. et al., Antiepileptic drug development: II. Anticonvulsant drug screening, Epilepsia, 19(4):409-428 (1978).
Krska, S. et al., Enantioselective synthesis of a chiral fluoropiperidine via asymmetric hydrogenation of a vinyl fluoride, Tetrahedron, 65:8987-8994 (2009).
Layton, M. et al., Recent advances in the development of NR2B subtype-selective NMDA receptor antagonists, Curr Top Med Chem, 6(7):697-709 (2006).
Layton, M.E. et al., Discovery of 3-Substituted Aminocyclopentances as Potent and Orally Bioavailable NR2B Subtype-Selective NMDA Antagonists, ACS Chem. Neurosci., 2:352-362 (2011).
Lemke, J. et al., GRIN2B Mutations in West Syndrome and Intellectual Disability with Focal Epilepsy, Ann Neurol, 75:147-154 (2014).
Li, L. et al., Role of NR2B-type NMDA receptors in selective neurodegeneration in Huntington disease, Neurobiology of Aging, 24:1113-1121 (2003).
Lima-Ojeda, J.M. et al., Pharmacological blockad of GluN2B-containing NMDA reeptors induces antidepressant-like effects lacking psychotomimetic action and neurotoxicity in the perinatal and adult rodent brain, Progress in Neuro-Psychopharmacology & Biological Psychiatry, 45:28-33 (2013).
Liverton, N. et al., Identification and characterization of 4-methylbenzyl 4-[(pyrimidin-2-ylamino)methyl]piperidine-1-carboxylate, an orally bioavailable, brain penetrant NR2B selective N-methyl-D-aspartate receptor antagonist, J Med Chem, 50(4):807-819 (2007).
Loscher, Wolfgang, Critical review of current animal models of seizures and epilepsy used in the discovery and development of new antiepileptic drugs, Seizure, 20(5):359-368 (2011).
Lucki, I. et al., Sensitivity to the effects of pharmacologically selective antidepressants in different strains of mice, Psychopharmacology (Berl), 155(3):315-322 (2001).
Mares, P. and Mikulecka, A., Different effects of two N-methyl-D-aspartate receptor antagonists on seizures, spontaneous behavior, and motor performance in immature rats, Epilepsy & Behavior, 14:32-39 (2009).
Mares, P., Age and activation determines the anticonvulsant effect in ifenprodil in rats, Naunyn-Schmiedeberg's Arch Pharmacol, 387:753-761 (2014).
Mathews, D. and Zarate, C., Current status of ketamine and related compounds for depression, J Clin Psychiatry, 74(5):516-517 (2013).
Menniti, F. et al., CP-101,606: An NR2B-Selective NMDA Receptor Antagonist, CNS Drug Reviews, 4(4):307-322 (1998).

Menniti, F.S. et al., CP-101,606, An NR2B subunit selective NMDA receptor antagonist, inhibits NMDA and injury induced c-fos expression and corticol spreading depression in rodents, Neurpharmacology, 39:1147-1155 (2000).
Mony, L. et al., Allosteric modulators of NR2B-containing NMDA receptors: molecular mechanisms and therapeutic potential, Br J Pharmacol, 157(8):1301-1317 (2009).
Murrough, J. et al., Antidepressant efficacy of ketamine in treatment-resistant major depression: a two-site randomized controlled trial, Am J Psychiatry, 170(10):1134-1142 (2013).
Naspolini, A.P. et al., Traxoprodil decreases pentylenetetrazol-induced seizures, Epilepsy Research, 100:12-19 (2012).
Neligan, et al., The epidemiology of the epilepsies, Handb Clin Neurol, 107:113-133 (2012).
Nielsen, D. et al., Antidepressant-like activity of corticotropin-releasing factor type-1 receptor antagonists in mice, European Journal of Pharmacology, 499:135-146 (2004).
Niesters, M. et al., Ketamine for chronic pain: risks and benefits, British Journal of Clinical Pharmacology, 77(2):357-367 (2013).
Noppers, I. et al., Drug-induced liver injury following a repeated course of ketamine treatment for chronic pain in CRPS type 1 patients: a report of 3 cases, Pain, 152(9):2173-2178 (2011).
Nutt, J.G. et al., Effects of NR2B Selective NMDA Glutamate Antagonist, CP-101,606, on Dyskinesia and Parkinsonism, Movement Disorders, 23(13):1860-1866 (2008).
Paoletti, P. et al., NMDA receptor subunit diversity: impact on receptor properties, synaptic plasticity and disease, Nat Rev Neurosci, 14(6):383-400 (2013).
Peeters, M. et al., Effects of Pan- and Subtype-Selective N-Methyl-D-aspartate Receptor Antagonists on Cortical Spreading Depression in the Rat: Therapeutic Potential for Migraine, The Journal of Pharmacology and Experimental Therapeutics, 321(2):564-572 (2007).
Porsolt, et al., Behavioral Despair in Rats: A New Model Sensitive to Antidepressant Treatments, Eur. J. Pharmacol., 47:379-391 (1978).
Porsolt, R. et al., Behavioral despair in mice: a primary screening test for antidepressants, Arch Int Pharmacodyn Ther, 229(2):327-336 (1977).
Porsolt, R. et al., Depression: a new animal model sensitive to antidepressant treatments, Nature, 266(5604):730-732 (1977).
Preskorn, S. et al., An innovative design to establish proof of concept of the antidepressant effects of the NR2B subunit selective N-methyl-D-aspartate antagonist, CP-101,606, in patients with treatment-refractory major depressive disorder, J Clin Psychopharmacol, 28(6):631-637 (2008).
Reynolds, I. and Miller, R., Ifenprodil is a novel type of N-methyl-D-aspartate receptor antagonist: interaction with polyamines, Mol Pharmacol, 36(5):758-765 (1989).
Ruppa, K. et al., NMDA Antagonists of GluN2B Subtype and Modulators of GluN2A, GluN2C, and GluN2D Subtypes—Recent Results and Developments, Annual Reports in Medicinal Chemistry, 47:89-103 (2012).
Sanacora, G. et al., Targeting the glutamatergic system to develop novel, improved therapeutics for mood disorders, Nat Rev Drug Discov, 7(5):426-437 (2008).
Sang, C.N. et al., The NR2B subunit-selective NMDA receptor antagonist, CP-101,606, reduces spontaneous pain intensity in patients with central and peripheral neuropathic pain, Society for Neuroscience, Abstract 814.9 (2003).
Shatillo, A., et al., Involvement of NMDA receptor subtypes in cortical spreading depression in rats assessed by fMRI, Neuropharmacology, 93:164-170 (2015).
Shehadeh, J. et al., Striatal neuronal apoptosis is preferentially enhanced by NMDA receptor activation in YAC transgenic mouse model of Huntington disease, Neurobiology of Disease, 21:392-403 (2006).
Slattery, D. and Cryan, J., Using the rat forced swim test to assess antidepressant-like activity in rodents, Nat Protoc, 7(6):1009-1014 (2012).
Steece-Collier, K. et al., Antiparkinsonian actions of CP-101,606, an antagonist of NR2B subunit-containing N-methyl-d-aspartate receptors, Exp Neurol, 163(1):239-243 (2000).
Swinyard, E. et al., Comparative assays of antiepileptic drugs in mice and rats, J Pharmacol Exp Ther, 106(3):319-330 (1952).

(56) References Cited

OTHER PUBLICATIONS

Szczurowska, E. and Mares, P., Different action of a specific NR2B/NMDA antagonist Ro 25/6981 on cortical evoked potentials and epileptic afterdischarges in immature rats, Brain Research Bulletin, 111:1-8 (2015).

Tahirovic, Y.A. et al., Enantiomeric Propanolamines as selective N-Methyl-D-aspartate 2B Receptor Antagonists, J. Med. Chem., 51:5506-5521 (2008).

Tang, W. and Zhang, X., New chiral phosphorus ligands for enantioselective hydrogenation, Chem Rev,103(8):3029-3070 (2003).

Taniguchi, K. et al., Antinociceptive activity of CP-101,606 an NMDA receptor NR2B subunit antagonist, British Journal of Pharmacology, 122:809-812 (1997).

Traynelis, S. et al., Glutamate receptor ion channels: structure, regulation, and function, Pharmacol Rev, 62(3):405-496 (2010).

Tudge, M. et al., Development of a Kilogram-Scale Asymmetric Synthesis of a Potent DP Receptor Antagonist, Organic Process Research and Development, 14:787-798 (2010).

Vengeliene, V. et al., The role of the NMDA receptor in alcohol relapse: a pharmacological mapping study using the alcohol deprivation effect, Neuropharmacology, 48:822-829 (2005).

Wang, H. et al., pH-Sensitive NMDA Inhibitors Improve Outcome in a Murine Model of SAH, Neurocrit Care, 21:119-131 (2014).

Wang, X.M. and Bausch, S.B., Effects of distinct classes of N-methyl-D-aspartate receptor antagonist on seizures, axonal sprouting and neuronal loss in vitro: suppression by NR2B-selective antagonists, Neuropharmacology, 47:1008-1020 (2004).

Warraich, S.T. et al., Evaluation of behavioural effects of a selective NMDA NR1A/2B receptor antagonist in the unilateral 6-OHDA lesion rat model, Brain Research Bulletin, 79:85-90 (2009).

Wessel, R.H. et al., NR2B selective NMDA receptor antagonist CP-101,606 prevents levodopa-induced motor response alterations in hemi-parkinsonian rats, Neuropharmacology, 47:184-194 (2004).

Written Opinion for PCT/US2015/034009, 6 pages (dated Sep. 30, 2015).

Written Opinion for PCT/US2015/050267, 5 pages (dated Dec. 9, 2015).

Written Opinion for PCT/US2015/051488, 9 pages (dated Jan. 27, 2016).

Written Opinion for PCT/US2016/35098, 8 pages (dated Aug. 31, 2016).

Written Opinion for PCT/US2017/062726 (Treatment of Autism Spectrum Disorders, Obsessive-Compulsive Disorder and Anxiety Disorders, filed Nov. 21, 2017), issued by ISA/EP, 11 pages (dated Apr. 3, 2018).

Xie, X. et al., Role of a Hippocampal Src-Family Kinase-Mediated Glutamatergic Mechanism in Drug Context-Induced Cocaine Seeking, Neuropsychopharmacology, 38:2657-2665 (2013).

Yuan, H. et al., Context-Dependent GluN2B-Selective Inhibitors of NMDA Receptor Function Are Neuroprotective with Minimal Side Effects, Neuron, 85:1305-1318 (2015).

Zarate, C. et al., A randomized trial of an N-methyl-D-aspartate antagonist in treatment-resistant major depression, Arch Gen Psychiatry, 63(8):856-864 (2006).

Zarate, C. et al., Replication of ketamine's antidepressant efficacy in bipolar depression: a randomized controlled add-on trial, Biol Psychiatry, 71(11):939-946 (2012).

Zeron, M.M. et al., Increased Sensitivity to N-Methyl-D-Aspartate Receptor-Mediated Excitotoxicity in a Mouse Model of Huntington's Disease, Neuron, 33:849-860 (2002).

* cited by examiner

3,3-DIFLUORO-PIPERIDINE DERIVATIVES AS NR2B NMDA RECEPTOR ANTAGONISTS

BACKGROUND

Non-selective NMDA receptor antagonists, originally developed in stroke and head trauma, have more recently shown clinical efficacy in treating depression. The non-selective NMDA receptor antagonist, ketamine, has been shown to have rapid onset and efficacy in depression resistant to standard monoamine reuptake inhibitor therapy (Mathews and Zarate, 2013, *J. Clin. Psychiatry* 74:516-158). However, non-selective NMDA receptor antagonists such as ketamine have a range of undesirable pharmacological activities which limit application in humans. In particular dissociative or psychogenic side effects are particularly prominent for non-selective NMDA receptor antagonists. More recently, NR2B subtype selective NMDA receptor antagonists have demonstrated potential in a wide range of clinical indications. In particular, NR2B antagonists have also demonstrated antidepressant activity in early stage clinical trials (Ibrahim et al., 2012, *J. Clin. Psychopharmacol.* 32, 551-557; Preskorn et al., 2008, *J. Clin. Psychopharmacol.* 28, 631-637). Furthermore, selective NR2B antagonists have advantages over unselective NMDA receptor antagonists such as ketamine due to greatly diminished dissociative side effects. However, NR2B antagonists described to date have generally exhibited drawbacks with regard to other drug properties which have limited potential use in human drug therapy.

SUMMARY

For broad scope of application and safe human use in a range of clinical indications including depression, improved NR2B subtype selective antagonists are needed. The present invention, among other things, addresses the need for NR2B receptor antagonists that are improved in one or more aspects exemplified by pharmacokinetic performance, oral activity, cardiovascular safety, and in vitro and in vivo therapeutic safety index measures.

In some embodiments, the present invention encompasses the insight that chemical entities of formula I:

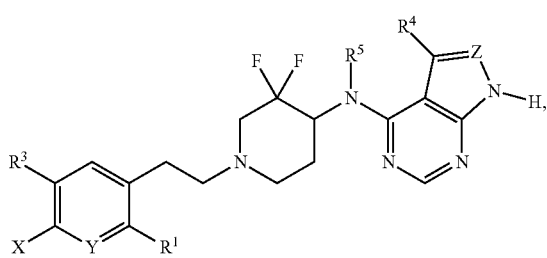

wherein X, Y, Z, $R^1$, $R^3$, $R^4$ and $R^5$ are defined herein, are NR2B subtype selective receptor antagonists. Chemical entities of formula I, and pharmaceutically acceptable compositions thereof, are useful for treating a variety of diseases and disorders associated with NR2B receptor antagonism. Such diseases and disorders include those described herein.

DETAILED DESCRIPTION OF CERTAIN EMBODIMENTS

General Description of Chemical Entities

Figure 1A:
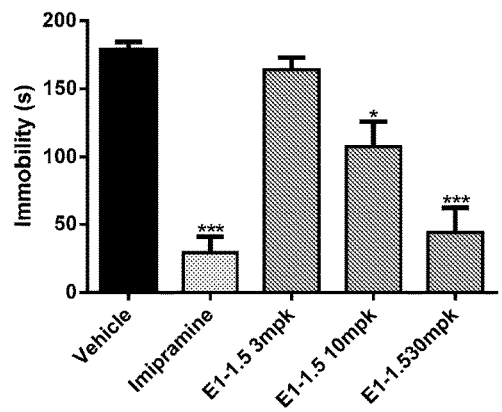
FIGS. 1A and 1B show results of the forced swim test as described in Example 2.4.1 with compounds E1-1.5 ((+)-(R*)-N-(3,3-difluoro-1-(4-(trifluoromethyl)phenethyl)piperidin-4-yl)-1H-pyrazolo[3,4-d]pyrimidin-4-amine) and E2-1.5 ((−)-(S*)-N-(3,3-difluoro-1-(4-(trifluoro-methyl)phenethyl)piperidin-4-yl)-1H-pyrazolo[3,4-d]pyrimidin-4-amine), respectively.

In some embodiments, the present invention provides chemical entities of formula I:

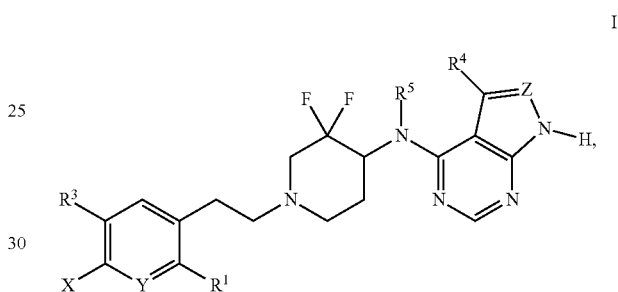

wherein:
X is —H; halo; $C_1$-$C_6$ alkyl optionally substituted with 1 to 6 fluoro; $C_3$-$C_6$ cycloalkyl; $C_1$-$C_4$ alkoxy optionally substituted with 1 to 6 fluoro; —CN; —NO$_2$; —N($R^7$)($R^8$); —SR$^7$; —S(O)$_2$R$^6$; or —CO$_2$R$^2$;
Y is C($R^2$) or N;
Z is C(H) or N;
$R^1$ is —H, halo, $C_1$-$C_4$ alkyl optionally substituted with 1 to 3 fluoro; $C_3$-$C_6$ cycloalkyl; $C_1$-$C_4$ alkoxy optionally substituted with 1 to 3 fluoro; —CN; —NO$_2$; —N($R^7$)($R^8$); —CO$_2$R$^7$; or —C(O)N($R^7$)($R^8$);
$R^2$ is —H; halo; $C_1$-$C_4$ alkyl optionally substituted with 1 to 3 fluoro; cyclopropyl; or $C_1$-$C_4$ alkoxy optionally substituted with 1 to 3 fluoro;
$R^3$ is —H, —F, —Cl, —CH$_3$, —CF$_3$ or —OCH$_3$;
$R^4$ is —H, —F; —Cl; $C_1$-$C_3$ alkyl optionally substituted with 1 to 3 fluoro; or cyclopropyl;
$R^5$ is —H or —CH$_3$;
each instance of $R^6$ independently is $C_1$-$C_4$ alkyl optionally substituted with 1 to 3 fluoro;
each instance of $R^7$ independently is $C_1$-$C_4$ alkyl; and
each instance of $R^8$ independently is —H or $C_1$-$C_4$ alkyl.

Unless otherwise specified or clear from context, the term "chemical entity" refers to a compound having the indicated structure, whether in its "free" form (e.g., "free compound" or "free base" or "free acid" form, as applicable), or in a salt form, particularly a pharmaceutically acceptable salt form, and furthermore whether in solid state form or otherwise. In some embodiments, a solid state form is an amorphous (i.e., non-crystalline) form; in some embodiments, a solid state form is a crystalline form. In some embodiments, a crystalline form is a polymorph, pseudohydrate, or hydrate. Similarly, the term encompasses the compound whether provided in solid form or otherwise. Unless otherwise specified, all statements made herein regarding "compounds" apply to the associated chemical entities, as defined.

Chemical Entities and Definitions

Unless otherwise specified, the word "includes" (or any variation thereon, e.g., "include", "including", etc.) is intended to be open-ended. For example, "A includes 1, 2 and 3" means that A includes but is not limited to 1, 2 and 3.

Unless otherwise specified, the phrase "such as" is intended to be open-ended. For example, "A can be a halogen, such as chlorine or bromine" means that A can be, but is not limited to, chlorine or bromine.

Chemical entities of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

The term "alkyl", as by itself or as part of another substituent, means a substituted or unsubstituted, linear or branched, univalent hydrocarbon chain that is completely saturated or that contains one or more units of unsaturation. Unless otherwise specified, alkyl groups contain 1 to 7 carbon atoms ("$C_1$-$C_7$ alkyl"). In some embodiments, alkyl groups contain 1 to 6 carbon atoms ("$C_1$-$C_6$ alkyl"). In some embodiments, alkyl groups contain 1 to 5 carbon atoms ("$C_1$-$C_5$ alkyl"). In some embodiments, alkyl groups contain 1 to 4 carbon atoms ("$C_1$-$C_4$ alkyl"). In some embodiments, alkyl groups contain 3 to 7 carbon atoms ("$C_3$-$C_7$ alkyl"). Examples of saturated alkyl groups include methyl, ethyl, n-propyl, i-propyl, n-butyl, t-butyl, i-butyl, s-butyl, homologs and isomers of, for example, n-pentyl, n-hexyl, n-heptyl, n-octyl, and the like. An unsaturated alkyl group is one having one or more carbon-carbon double bonds or carbon-carbon triple bonds. Examples of unsaturated alkyl groups include allyl, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the like. The term "lower alkyl" refers to alkyl groups having 1 to 4 (if saturated) or 2 to 4 (if unsaturated) carbon atoms. Exemplary lower alkyl groups include methyl, ethyl, n-propyl, i-propyl, n-butyl, s-butyl, i-butyl, t-butyl and the like. The term "alkenyl" refers to alkyl groups having at least two carbon atoms and at least one carbon-carbon double bond. The term "alkynyl" refers to alkyl groups having at least two carbon atoms and at least one carbon-carbon triple bond.

The term "cycloalkyl", by itself or as part of another substituent, refers to a monocyclic univalent hydrocarbon that is completely saturated or that contains one or more units of unsaturation, but which is not aromatic, that has a single point of attachment to the rest of the molecule. In some embodiments, cycloalkyl groups contain 3 to 8 ring carbon atoms ("$C_3$-$C_8$ cycloalkyl"). Examples of cycloalkyl include cyclopropyl, cyclobutyl, cyclopentyl, cyclohexyl, 1-cyclohexenyl, 3-cyclohexenyl, cycloheptyl, and the like.

The term "alkoxy", by itself or as part of another substituent, refers to the group —O-alkyl.

The term "halogen" or "halo", by itself or as part of another substituent, refers to fluorine, chlorine, bromine or iodine.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 1977, 66:1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement hydrogen, carbon, nitrogen, oxygen, chlorine or fluorine with $^2H$, $^3H$, $^{11}C$, $^{13}C$, $^{14}C$, $^{13}N$, $^{15}N$, $^{17}O$, $^{18}O$, $^{36}Cl$ or $^{18}F$, respectively, are within the scope of this invention. Such compounds are useful, for example, as analytical tools, as probes in biological assays, or as therapeutic agents in accordance with the present invention. Additionally, incorporation of heavier isotopes such as deuterium ($^2$H) can afford certain therapeutic advantages resulting from greater metabolic stability, for example, increase in vivo half-life, or reduced dosage requirements.

Diastereomeric excess is expressed as % de, i.e., for diastereomers X and Y, the diastereomeric excess of X=((x−y)/(x+y))*100, where x and y are the fractions of X and Y, respectively.

Enantiomeric excess is expressed as % ee, i.e., for enantiomers X and Y, the entiomeric excess of X=((x−y)/(x+y))*100, where x and y are the fractions of X and Y, respectively.

Exemplary Embodiments of Chemical Entities

In some embodiments, the present invention provides chemical entities of formula I:

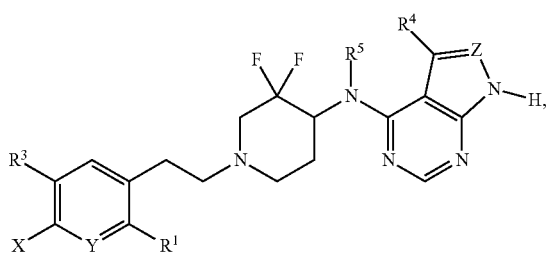

(I)

wherein:
X is —H; halo; $C_1$-$C_6$ alkyl optionally substituted with 1 to 6 fluoro; $C_3$-$C_6$ cycloalkyl; $C_1$-$C_4$ alkoxy optionally substituted with 1 to 6 fluoro; —CN; —NO$_2$; —N(R$^7$)(R$^8$); —SR$^7$; —S(O)$_2$R$^6$; or —CO$_2$R$^7$;
Y is C(R$^2$) or N;
Z is C(H) or N;
R$^1$ is —H, halo, $C_1$-$C_4$ alkyl optionally substituted with 1 to 3 fluoro; $C_3$-$C_6$ cycloalkyl; $C_1$-$C_4$ alkoxy optionally substituted with 1 to 3 fluoro; —CN; —NO$_2$; —N(R$^7$)(R$^8$); —CO$_2$R$^7$; or —C(O)N(R$^7$)(R$^8$);
R$^2$ is —H; halo; $C_1$-$C_4$ alkyl optionally substituted with 1 to 3 fluoro; cyclopropyl; or $C_1$-$C_4$ alkoxy optionally substituted with 1 to 3 fluoro;
R$^3$ is —H, —F, —Cl, —CH$_3$, —CF$_3$ or —OCH$_3$;
R$^4$ is —H, —F; —Cl; $C_1$-$C_3$ alkyl optionally substituted with 1 to 3 fluoro; or cyclopropyl;
R$^5$ is —H or —CH$_3$;
each instance of R$^6$ independently is $C_1$-$C_4$ alkyl optionally substituted with 1 to 3 fluoro;
each instance of R$^7$ independently is $C_1$-$C_4$ alkyl; and
each instance of R$^8$ independently is —H or $C_1$-$C_4$ alkyl.
In some embodiments,
X is —H; —F; —Cl; $C_1$-$C_4$ alkyl; $C_1$-$C_3$ alkyl substituted with 1 to 6 fluoro; cyclopropyl; $C_1$-$C_4$ alkoxy; $C_1$-$C_2$ alkoxy substituted with 1 to 3 fluoro; —CN; —NO$_2$; —N(R$^7$)(R$^8$); —SR$^7$; or —S(O)$_2$R$^6$;
Y is C(R$^2$) or N;
Z is C(H) or N;
R$^1$ is —H; —F; —Cl; $C_1$-$C_4$ alkyl; $C_1$-$C_2$ alkyl substituted with 1 to 3 fluoro; cyclopropyl; $C_1$-$C_4$ alkoxy; $C_1$-$C_2$ alkoxy substituted with 1 to 3 fluoro; —CN; —NO$_2$; —N(R$^7$)(R$^8$); —CO$_2$R$^7$; or —C(O)N(R$^7$)(R$^8$);
R$^2$ is —H; —F; —Cl; $C_1$-$C_4$ alkyl; $C_1$-$C_2$ alkyl substituted with 1 to 3 fluoro; cyclopropyl; $C_1$-$C_4$ alkoxy; $C_1$-$C_2$ alkoxy substituted with 1 to 3 fluoro;
R$^3$ is —H, —F, —Cl, —CH$_3$, —CF$_3$ or —OCH$_3$;
R$^4$ is —H, —F, —Cl, —CH$_3$, —CF$_3$, or cyclopropyl;
R$^5$ is —H or —CH$_3$;
each instance of R$^6$ independently is $C_1$-$C_2$ alkyl optionally substituted with 1 to 3 fluoro;
each instance of R$^7$ independently is $C_1$-$C_2$ alkyl; and
each instance of R$^8$ independently is —H or $C_1$-$C_2$ alkyl.
In some embodiments,
X is —H; —F; —Cl; $C_1$-$C_2$ alkyl optionally substituted with 1 to 3 fluoro; or $C_1$-$C_2$ alkoxy optionally substituted with 1 to 3 fluoro;
Y is C(R$^2$) or N;
Z is C(H) or N;
R$^1$ is —H, halo or —CH$_3$;
R$^2$ is —H, —F, —Cl or —CH$_3$;
R$^3$ is —H, —F, —Cl, —CH$_3$ or —CF$_3$;
R$^4$ is —H, —F, —CH$_3$ or —CF$_3$; and
R$^5$ is —H or —CH$_3$.
In some embodiments,
X is —H, —F, —Cl, —CH$_3$, —CH$_2$F, —CHF$_2$, —CF$_3$, —OCHF$_2$ or —OCF$_3$;
Y is C(R$^2$) or N;
Z is C(H) or N;
R$^1$ is —H or —F;
R$^2$ is —H;
R$^3$ is —H, —F or —CF$_3$;
R$^4$ is —H or —CH$_3$; and
R$^5$ is —H or —CH$_3$.
In some embodiments, X is —H. In some embodiments, X is —F or —Cl. In some embodiments, X is $C_1$-$C_4$ alkyl. In some embodiments, X is —CH$_3$, —CH$_2$CH$_3$, —CH(CH$_3$)$_2$, —CF$_3$, —CHF$_2$, —CH$_2$F, —CF$_2$CF$_3$, —CH(CF$_3$)$_2$ or —CH$_2$CF$_2$CF$_3$. In some embodiments, X is $C_3$-$C_6$ cycloalkyl. In some embodiments, X is cyclopropyl. In some embodiments, X is $C_1$-$C_4$ alkoxy. In some embodiments, X is —OCH$_3$, —OCF$_3$, —OCHF$_2$ or OCFH$_2$. In some embodiments, X is —CN. In some embodiments, X is —SCH$_3$, —SCH$_2$CH$_3$, —SO$_2$CH$_2$CH$_3$, —SO$_2$CH$_3$ or —SO$_2$CF$_3$. In some embodiments, X is —NO$_2$. In some embodiments, X is —N(R$^7$)(R$^8$). In some embodiments, X is —N(CH$_3$)$_2$, —NH(CH$_3$) or —N(CH$_3$)(CH$_2$CH$_3$).

In some embodiments, R$^1$ is —H. In some embodiments, R$^1$ is —F or —Cl. In some embodiments, R$^1$ is $C_1$-$C_4$ alkyl. In some embodiments, R$^1$ is —CH$_3$, —CH$_2$CH$_3$, —CH(CH$_3$)$_2$ or —CF$_3$. In some embodiments, R$^1$ is $C_3$-$C_6$ cycloalkyl. In some embodiments, R$^1$ is cyclopropyl. In some embodiments, R$^1$ is $C_1$-$C_4$ alkoxy. In some embodiments, R$^1$ is —OCH$_3$, —OCF$_3$, —OCHF$_2$ or —OCFH$_2$. In some embodiments, R$^1$ is —CN or —NO$_2$. In some embodiments, R$^1$ is —C(O)N(R$^7$)(R$^8$). In some embodiments, R$^1$ is —C(O)N(CH$_3$)$_2$, —C(O)NH(CH$_3$) or —C(O)N(CH$_3$)(CH$_2$CH$_3$). In some embodiments, R$^1$ is —CO$_2$R$^7$. In some embodiments, R$^1$ is —CO$_2$CH$_3$ or —CO$_2$CH$_2$CH$_3$.

In some embodiments, R$^2$ is —H. In some embodiments, R$^2$ is —F or —Cl. In some embodiments, R$^2$ is $C_1$-$C_4$ alkyl. In some embodiments, R$^2$ is —CH$_3$, —CH$_2$CH$_3$, —CH(CH$_3$)$_2$ or —CF$_3$. In some embodiments, R$^2$ is cyclopropyl. In some embodiments, R$^2$ is $C_1$-$C_4$ alkoxy. In some embodiments, R$^2$ is —OCH$_3$, —OCF$_3$, —OCHF$_2$ or —OCFH$_2$.

In some embodiments, R$^3$ is —H. In some embodiments, R$^3$ is —F or —Cl. In some embodiments, R$^3$ is —CH$_3$, —CF$_3$ or —OCH$_3$.

In some embodiments, R$^4$ is —H. In some embodiments, R$^4$ is —F or —Cl. In some embodiments, R$^4$ is —CH$_3$. In some embodiments, R$^4$ is cyclopropyl.

In some embodiments, R$^5$ is —H. In some embodiments, R$^5$ is —CH$_3$.

In some embodiments, a chemical entity of formula (I) is a chemical entity of formula (I-R*):

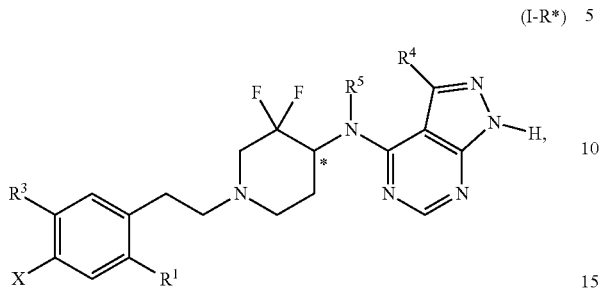

(I-R*)

in which the asterisk (*) denotes absolute stereochemistry at the indicated stereocenter, and wherein each of X, R¹, R³, R⁴ and R⁵ is as described in embodiments of formula (I), supra, or described in embodiments herein, both singly and in combination. The stereochemistry at the indicated stereocenter is that resulting from the synthesis using (R)-(+)-1-phenylethylamine as described in Example 1.G. This convention is maintained throughout the application, not only regarding chemical entities of formula (I) but also in synthetic intermediates.

Designation of the stereocenter as R* indicates that the R* isomer is present in greater amount than the corresponding S* isomer. For example, the R* isomer can be present in an enantiomeric excess of 50%, 60%, 70%, 80%, 85%, 90%, 92%, 94%, 96% or 98% relative to the S* isomer. Similarly, in synthetic intermediates in which more than one stereocenter may be indicated, the R* isomer can be present in a diastereomeric excess of 50%, 60%, 70%, 80%, 85%, 90%, 92%, 94%, 96% or 98% relative to the S* isomer.

In some embodiments, a chemical entity of formula (I) is a chemical entity of formula (I-S*):

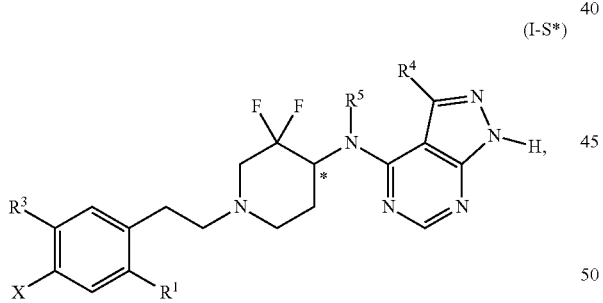

(I-S*)

in which the asterisk (*) denotes absolute stereochemistry at the indicated stereocenter, and wherein each of X, R¹, R³, R⁴ and R⁵ is as described in embodiments of formula (I), supra, or described in embodiments herein, both singly and in combination. The stereochemistry at the indicated stereocenter is that resulting from the synthesis using (S)-(–)-1-phenylethylamine as described in Example 1.H. This convention is maintained throughout the application, not only regarding chemical entities of formula (I) but also in synthetic intermediates.

Designation of the stereocenter as S* indicates that the S* isomer is present in greater amount than the corresponding R* isomer. For example, the S* isomer can be present in an enantiomeric excess of 50%, 60%, 70%, 80%, 85%, 90%, 92%, 94%, 96% or 98% relative to the R* isomer. Similarly, in synthetic intermediates in which more than one stereocenter may be indicated, the S* isomer can be present in a diastereomeric excess of 50%, 60%, 70%, 80%, 85%, 90%, 92%, 94%, 96% or 98% relative to the R* isomer.

Designation of the optical rotation of a chemical entity indicates that the indicated enantiomer is present in greater amount than the opposite enantiomer. For example, the (–) isomer can be present in an enantiomeric excess of 50%, 60%, 70%, 80%, 85%, 90%, 92%, 94%, 96% or 98% relative to the (+) isomer. Similarly, the (+) isomer can be present in an enantiomeric excess of 50%, 60%, 70%, 80%, 85%, 90%, 92%, 94%, 96% or 98% relative to the (–) isomer.

In some embodiments, a chemical entity of formula (I) is a chemical entity of formula (II):

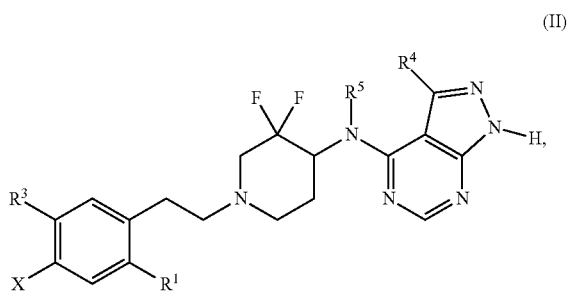

(II)

wherein each of X, R¹, R³, R⁴ and R⁵ is as described in embodiments of formula (I), supra, or described in embodiments herein, both singly and in combination.

In some embodiments of formula (II),
X is —H, —F, —Cl, —CH₃, —CH₂CH₃, —CH(CH₃)₂, —CF₃, —CHF₂, —CH₂F, —CF₂CF₃, —CH(CF₃)₂, —CH₂CF₂CF₃, cyclopropyl, —OCH₃, —OCF₃, —OCHF₂, —OCFH₂, —CN, —NO₂, —N(CH₃)₂, —SCH₃, —SO₂CH₃ or —SO₂CF₃;
R¹ is —H, —F, —Cl, —CH₃, —CH₂CH₃, —CH(CH₃)₂, —CF₃, cyclopropyl, —OCH₃, —OCF₃, —OCHF₂, —OCFH₂, —CN, —NO₂, —CO₂CH₃, —CO₂CH₂CH₃, —C(O)N(CH₃)₂ or —C(O)NH(CH₃);
R³ is —H, —F, —Cl, —CH₃, —CF₃ or —OCH₃;
R⁴ is —H, —F; —Cl; C₁-C₃ alkyl optionally substituted with 1 to 3 fluoro; or cyclopropyl; and
R⁵ is —H or —CH₃.

In some embodiments of formula (II),
X is —H, —F, —Cl, —CH₃, —CH₂F, —CHF₂, —CF₃,— OCHF₂ or —OCF₃;
R¹ is —H or —F;
R³ is —H, —F or —CF₃;
R⁴ is —H or —CH₃; and
R⁵ is —H or —CH₃.

In some embodiments, a chemical entity of formula (I) is a chemical entity of formula (IIa):

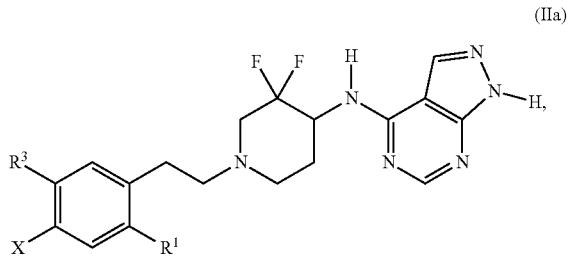

(IIa)

wherein each of X, R¹ and R³ is as described in embodiments of formula (I), supra, or described in embodiments herein, both singly and in combination.

In some embodiments of formula (IIa),

X is —H, —F, —Cl, —CH₃, —CH₂CH₃, —CH(CH₃)₂, —CF₃, —CHF₂, —CH₂F, —CF₂CF₃, —CH(CF₃)₂, —CH₂CF₂CF₃, cyclopropyl, —OCH₃, —OCF₃, —OCHF₂, —OCFH₂, —CN, —NO₂, —N(CH₃)₂, —SCH₃, —SO₂CH₃ or —SO₂CF₃;

R¹ is —H, —F, —Cl, —CH₃, —CH₂CH₃, —CH(CH₃)₂, —CF₃, cyclopropyl, —OCH₃, —OCF₃, —OCHF₂, —OCFH₂, —CN, —NO₂, —CO₂CH₃, —CO₂CH₂CH₃, —C(O)N(CH₃)₂ or —C(O)NH(CH₃); and R³ is —H, —F, —Cl, —CH₃, —CF₃ or —OCH₃.

In some embodiments of formula (IIa),

X is —H, —F, —Cl, —CH₃, —CH₂F, —CHF₂, —CF₃, —OCHF₂ or —OCF₃;

R¹ is —H or —F; and

R³ is —H, —F or —CF₃.

In some embodiments, a chemical entity of formula (I) is a chemical entity of formula (III):

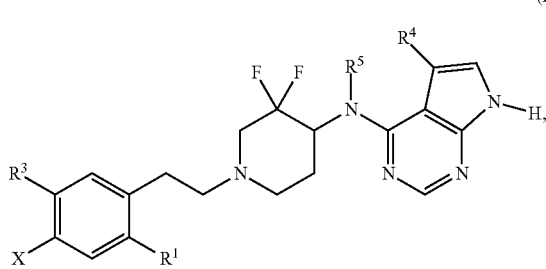

(III)

wherein each of X, R¹, R³, R⁴ and R⁵ is as described in embodiments of formula (I), supra, or described in embodiments herein, both singly and in combination.

In some embodiments of formula (III),

X is —H, —F, —Cl, —CH₃, —CH₂CH₃, —CH(CH₃)₂, —CF₃, —CHF₂, —CH₂F, —CF₂CF₃, —CH(CF₃)₂, —CH₂CF₂CF₃, cyclopropyl, —OCH₃, —OCF₃, —OCHF₂, —OCFH₂, —CN, —NO₂, —N(CH₃)₂, —SCH₃, —SO₂CH₃ or —SO₂CF₃;

R¹ is —H, —F, —Cl, —CH₃, —CH₂CH₃, —CH(CH₃)₂, —CF₃, cyclopropyl, —OCH₃, —OCF₃, —OCHF₂, —OCFH₂, —CN, —NO₂, —CO₂CH₃, —CO₂CH₂CH₃, —C(O)N(CH₃)₂ or —C(O)NH(CH₃);

R³ is —H, —F, —Cl, —CH₃, —CF₃ or —OCH₃;

R⁴ is —H, —F; —Cl; C₁-C₃ alkyl optionally substituted with 1 to 3 fluoro; or cyclopropyl; and R⁵ is —H or —CH₃.

In some embodiments of formula (III),

X is —H, —F, —Cl, —CH₃, —CH₂F, —CHF₂, —CF₃, —OCHF₂ or —OCF₃;

R¹ is —H or —F;

R³ is —H, —F or —CF₃;

R⁴ is —H or —CH₃; and

R⁵ is —H or —CH₃.

In some embodiments, a chemical entity of formula (I) is a chemical entity of formula (IIIa):

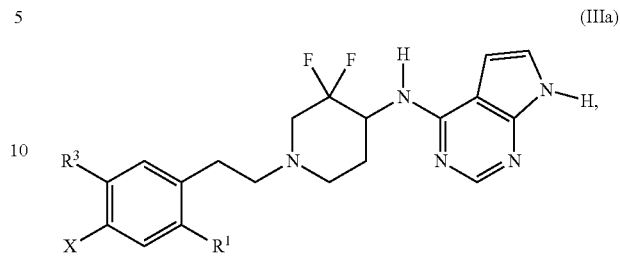

(IIIa)

wherein each of X, R¹ and R³ is as described in embodiments for formula (I), supra, or described in embodiments herein, both singly and in combination.

In some embodiments of formula (IIIa),

X is —H, —F, —Cl, —CH₃, —CH₂CH₃, —CH(CH₃)₂, —CF₃, —CHF₂, —CH₂F, —CF₂CF₃, —CH(CF₃)₂, —CH₂CF₂CF₃, cyclopropyl, —OCH₃, —OCF₃, —OCHF₂, —OCFH₂, —CN, —NO₂, —N(CH₃)₂, —SCH₃, —SO₂CH₃ or —SO₂CF₃;

R¹ is —H, —F, —Cl, —CH₃, —CH₂CH₃, —CH(CH₃)₂, —CF₃, cyclopropyl, —OCH₃, —OCF₃, —OCHF₂, —OCFH₂, —CN, —NO₂, —CO₂CH₃, —CO₂CH₂CH₃, —C(O)N(CH₃)₂ or —C(O)NH(CH₃); and R³ is —H, —F, —Cl, —CH₃, —CF₃ or —OCH₃.

In some embodiments of formula (IIIa),

X is —H, —F, —Cl, —CH₃, —CH₂F, —CHF₂, —CF₃, —OCHF₂ or —OCF₃;

R¹ is —H or —F; and

R³ is —H, —F or —CF₃.

In some embodiments, a chemical entity of formula (I) is a chemical entity of formula (IV):

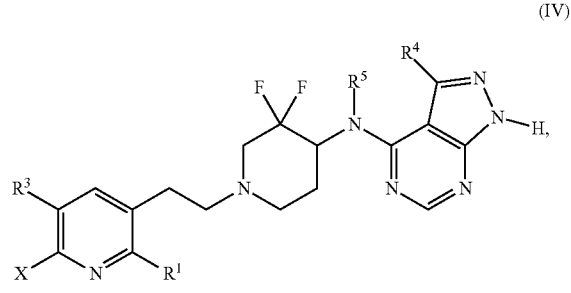

(IV)

wherein each of X, R¹, R³, R⁴ and R⁵ is as described in embodiments of formula (I), supra, or described in embodiments herein, both singly and in combination.

In some embodiments of formula (IV),

X is —H, —F, —Cl, —CH₃, —CH₂CH₃, —CH(CH₃)₂, —CF₃, —CHF₂, —CH₂F, —CF₂CF₃, —CH(CF₃)₂, —CH₂CF₂CF₃, cyclopropyl, —OCH₃, —OCF₃, —OCHF₂, —OCFH₂, —CN, —NO₂, —N(CH₃)₂, —SCH₃, —SO₂CH₃ or —SO₂CF₃;

R¹ is —H, —F, —Cl, —CH₃, —CH₂CH₃, —CH(CH₃)₂, —CF₃, cyclopropyl, —OCH₃, —OCF₃, —OCHF₂, —OCFH₂, —CN, —NO₂, —CO₂CH₃, —CO₂CH₂CH₃, —C(O)N(CH₃)₂ or —C(O)NH(CH₃);

R³ is —H, —F, —Cl, —CH₃, —CF₃ or —OCH₃;

R⁴ is —H, —F; —Cl; C₁-C₃ alkyl optionally substituted with 1 to 3 fluoro; or $R^5$ is —H or —CH$_3$.

In some embodiments of formula (IV),
X is —H, —F, —Cl, —CH$_3$, —CH$_2$F, —CHF$_2$, —CF$_3$, —OCHF$_2$ or —OCF$_3$;
$R^1$ is —H or —F;
$R^3$ is —H, —F or —CF$_3$;
$R^4$ is —H or —CH$_3$; and
$R^5$ is —H or —CH$_3$.

In some embodiments, a chemical entity of formula (I) is a chemical entity of formula (IVa):

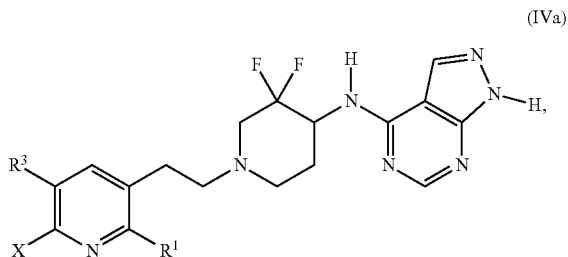

(IVa)

wherein each of X, $R^1$ and $R^3$ is as described in embodiments of formula (I), supra, or described in embodiments herein, both singly and in combination.

In some embodiments of formula (IVa),
X is —H, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH(CF$_3$)$_2$, —CH$_2$CF$_2$CF$_3$, cyclopropyl, —OCH$_3$, —OCF$_3$, —OCHF$_2$, —OCFH$_2$, —CN, —NO$_2$, —N(CH$_3$)$_2$, —SCH$_3$, —SO$_2$CH$_3$ or —SO$_2$CF$_3$;
$R^1$ is —H, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$, —OCFH$_2$, —CN, —NO$_2$, —CO$_2$CH$_3$, —CO$_2$CH$_2$CH$_3$, —C(O)N(CH$_3$)$_2$ or —C(O)NH(CH$_3$); and
$R^3$ is —H, —F, —Cl, —CH$_3$, —CF$_3$ or —OCH$_3$.

In some embodiments of formula (IVa),
X is —H, —F, —Cl, —CH$_3$, —CH$_2$F, —CHF$_2$, —CF$_3$, —OCHF$_2$ or —OCF$_3$;
$R^1$ is —H or —F; and
$R^3$ is —H, —F or —CF$_3$.

In some embodiments, a chemical entity of formula (I) is a chemical entity of formula (V):

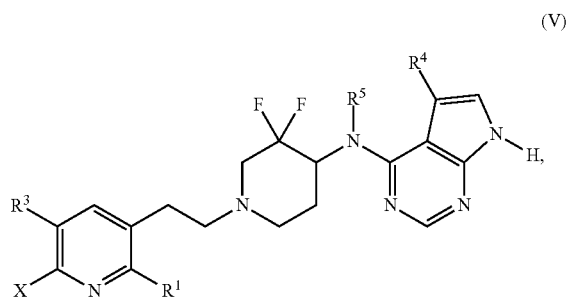

(V)

wherein each of X, $R^1$, $R^3$, $R^4$ and $R^5$ is as described in embodiments of formula (I), supra, or described in embodiments herein, both singly and in combination.

In some embodiments of formula (V),
X is —H, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH(CF$_3$)$_2$, —CH$_2$CF$_2$CF$_3$, cyclopropyl, —OCH$_3$, —OCF$_3$, —OCHF$_2$, —OCFH$_2$, —CN, —NO$_2$, —N(CH$_3$)$_2$, —SCH$_3$, —SO$_2$CH$_3$ or —SO$_2$CF$_3$;
$R^1$ is —H, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$, —OCFH$_2$, —CN, —NO$_2$, —CO$_2$CH$_3$, —CO$_2$CH$_2$CH$_3$, —C(O)N(CH$_3$)$_2$ or —C(O)NH(CH$_3$);
$R^3$ is —H, —F, —Cl, —CH$_3$, —CF$_3$ or —OCH$_3$;
$R^4$ is —H, —F; —Cl; C$_1$-C$_3$ alkyl optionally substituted with 1 to 3 fluoro; or cyclopropyl; and
$R^5$ is —H or —CH$_3$.

In some embodiments of formula (V),
X is —H, —F, —Cl, —CH$_3$, —CH$_2$F, —CHF$_2$, —CF$_3$, —OCHF$_2$ or —OCF$_3$;
$R^1$ is —H or —F;
$R^3$ is —H, —F or —CF$_3$;
$R^4$ is —H or —CH$_3$; and
$R^5$ is —H or —CH$_3$.

In some embodiments, a chemical entity of formula (I) is a chemical entity of formula (Va):

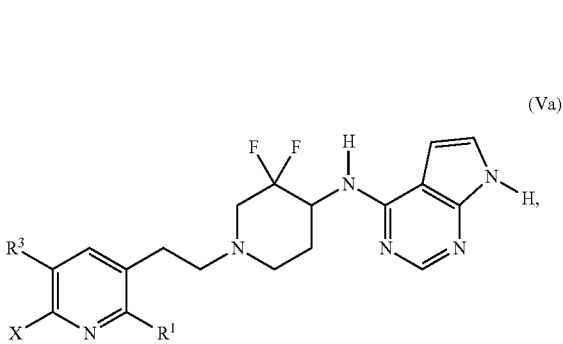

(Va)

wherein each of X, $R^1$ and $R^3$ is as described in embodiments for formula (I), supra, or described in embodiments herein, both singly and in combination.

In some embodiments of formula (Va),
X is —H, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH(CF$_3$)$_2$, —CH$_2$CF$_2$CF$_3$, cyclopropyl, —OCH$_3$, —OCF$_3$, —OCHF$_2$, —OCFH$_2$, —CN, —NO$_2$, —N(CH$_3$)$_2$, —SCH$_3$, —SO$_2$CH$_3$ or —SO$_2$CF$_3$;
$R^1$ is —H, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$, —OCFH$_2$, —CN, —NO$_2$, —CO$_2$CH$_3$, —CO$_2$CH$_2$CH$_3$, —C(O)N(CH$_3$)$_2$ or —C(O)NH(CH$_3$); and
$R^3$ is —H, —F, —Cl, —CH$_3$, —CF$_3$ or —OCH$_3$.

In some embodiments of formula (Va),
X is —H, —F, —Cl, —CH$_3$, —CH$_2$F, —CHF$_2$, —CF$_3$, —OCHF$_2$ or —OCF$_3$;
$R^1$ is —H or —F; and
$R^3$ is —H, —F or —CF$_3$.

Exemplary chemical entities of formula I are shown in Tables 1.0 to 4.C, 1.E1, 1.E2, 2.E1 and 2.E2, below.

TABLE 1.C (racemic)

| compound | X | R¹ | R³ | R⁴ | R⁵ |
|---|---|---|---|---|---|
| C-1.1 | H | H | H | H | H |
| C-1.2 | F | H | H | H | H |
| C-1.3 | Cl | H | H | H | H |
| C-1.4 | $CH_3$ | H | H | H | H |
| C-1.5 | $CF_3$ | H | H | H | H |
| C-1.6 | $CF_2H$ | H | H | H | H |
| C-1.7 | $CH_2F$ | H | H | H | H |
| C-1.8 | $CH_2CH_3$ | H | H | H | H |
| C-1.9 | cyclopropyl | H | H | H | H |
| C-1.10 | $CH_3O$ | H | H | H | H |
| C-1.11 | $CF_3O$ | H | H | H | H |
| C-1.12 | $CHF_2O$ | H | H | H | H |
| C-1.13 | $SCH_3$ | H | H | H | H |
| C-1.14 | CN | H | H | H | H |
| C-1.15 | F | F | H | H | H |
| C-1.16 | Cl | F | H | H | H |
| C-1.17 | $CH_3$ | F | H | H | H |
| C-1.18 | $CF_3$ | F | H | H | H |
| C-1.19 | $CF_2H$ | F | H | H | H |
| C-1.20 | $CH_2F$ | F | H | H | H |
| C-1.21 | $CH_2CH_3$ | F | H | H | H |
| C-1.22 | cyclopropyl | F | H | H | H |
| C-1.23 | F | Cl | H | H | H |
| C-1.24 | Cl | Cl | H | H | H |
| C-1.25 | $CH_3$ | Cl | H | H | H |
| C-1.26 | $CF_3$ | Cl | H | H | H |
| C-1.27 | cyclopropyl | Cl | H | H | H |
| C-1.28 | F | $CH_3$ | H | H | H |
| C-1.29 | Cl | $CH_3$ | H | H | H |
| C-1.30 | $CH_3$ | $CH_3$ | H | H | H |
| C-1.31 | $CF_3$ | $CH_3$ | H | H | H |
| C-1.32 | cyclopropyl | $CH_3$ | H | H | H |
| C-1.33 | $CF_3$ | H | H | H | $CH_3$ |
| C-1.34 | $CF_3$ | H | H | $CH_3$ | H |
| C-1.35 | H | F | F | H | H |
| C-1.36 | H | H | $CF_3$ | H | H |

TABLE 2.C (racemic)

| compound | X | R¹ | R³ | R⁴ | R⁵ |
|---|---|---|---|---|---|
| C-2.1 | H | H | H | H | H |
| C-2.2 | F | H | H | H | H |
| C-2.3 | Cl | H | H | H | H |
| C-2.4 | $CH_3$ | H | H | H | H |
| C-2.5 | $CF_3$ | H | H | H | H |
| C-2.6 | $CF_2H$ | H | H | H | H |
| C-2.7 | $CH_2F$ | H | H | H | H |
| C-2.8 | $CH_2CH_3$ | H | H | H | H |
| C-2.9 | cyclopropyl | H | H | H | H |
| C-2.10 | $CH_3O$ | H | H | H | H |
| C-2.11 | $CF_3O$ | H | H | H | H |
| C-2.12 | $CHF_2O$ | H | H | H | H |
| C-2.13 | $SCH_3$ | H | H | H | H |
| C-2.14 | CN | H | H | H | H |
| C-2.15 | F | F | H | H | H |
| C-2.16 | Cl | F | H | H | H |
| C-2.17 | $CH_3$ | F | H | H | H |
| C-2.18 | $CF_3$ | F | H | H | H |
| C-2.19 | $CF_2H$ | F | H | H | H |
| C-2.20 | $CH_2F$ | F | H | H | H |
| C-2.21 | $CH_2CH_3$ | F | H | H | H |
| C-2.22 | cyclopropyl | F | H | H | H |
| C-2.23 | F | Cl | H | H | H |
| C-2.24 | Cl | Cl | H | H | H |
| C-2.25 | $CH_3$ | Cl | H | H | H |
| C-2.26 | $CF_3$ | Cl | H | H | H |
| C-2.27 | cyclopropyl | Cl | H | H | H |
| C-2.28 | F | $CH_3$ | H | H | H |
| C-2.29 | Cl | $CH_3$ | H | H | H |
| C-2.30 | $CH_3$ | $CH_3$ | H | H | H |
| C-2.31 | $CF_3$ | $CH_3$ | H | H | H |
| C-2.32 | cyclopropyl | $CH_3$ | H | H | H |
| C-2.33 | $CF_3$ | H | H | H | $CH_3$ |
| C-2.34 | $CF_3$ | H | H | $CH_3$ | H |
| C-2.35 | H | F | F | H | H |
| C-2.36 | H | H | $CF_3$ | H | H |

TABLE 3.C (racemic)

| compound | X | R¹ | R³ | R⁴ | R⁵ |
|---|---|---|---|---|---|
| C-3.1 | H | H | H | H | H |
| C-3.2 | F | H | H | H | H |
| C-3.3 | Cl | H | H | H | H |
| C-3.4 | $CH_3$ | H | H | H | H |
| C-3.5 | $CF_3$ | H | H | H | H |
| C-3.6 | $CF_2H$ | H | H | H | H |
| C-3.7 | $CH_2F$ | H | H | H | H |
| C-3.8 | $CH_2CH_3$ | H | H | H | H |

TABLE 3.C-continued

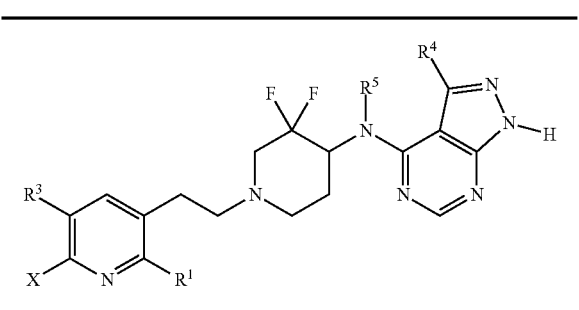

(racemic)

| compound | X | R¹ | R³ | R⁴ | R⁵ |
|---|---|---|---|---|---|
| C-3.9 | cyclopropyl | H | H | H | H |
| C-3.10 | CH₃O | H | H | H | H |
| C-3.11 | CF₃O | H | H | H | H |
| C-3.12 | CHF₂O | H | H | H | H |
| C-3.13 | SCH₃ | H | H | H | H |
| C-3.14 | CN | H | H | H | H |
| C-3.15 | F | F | H | H | H |
| C-3.16 | Cl | F | H | H | H |

TABLE 4.C

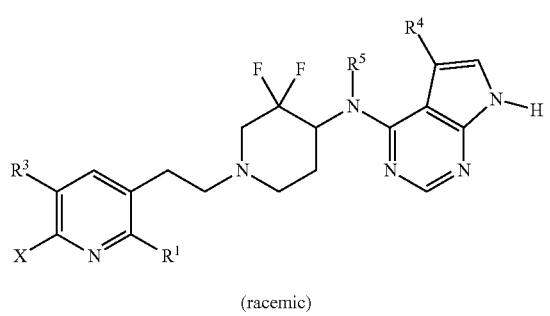

(racemic)

| compound | X | R¹ | R³ | R⁴ | R⁵ |
|---|---|---|---|---|---|
| C-4.1 | H | H | H | H | H |
| C-4.2 | F | H | H | H | H |
| C-4.3 | Cl | H | H | H | H |
| C-4.4 | CH₃ | H | H | H | H |
| C-4.5 | CF₃ | H | H | H | H |
| C-4.6 | CF₂H | H | H | H | H |
| C-4.7 | CH₂F | H | H | H | H |
| C-4.8 | CH₂CH₃ | H | H | H | H |
| C-4.9 | cyclopropyl | H | H | H | H |
| C-4.10 | CH₃O | H | H | H | H |
| C-4.11 | CF₃O | H | H | H | H |
| C-4.12 | CHF₂O | H | H | H | H |
| C-4.13 | SCH₃ | H | H | H | H |
| C-4.14 | CN | H | H | H | H |
| C-4.15 | F | F | H | H | H |
| C-4.16 | Cl | F | H | H | H |

TABLE 1.E1

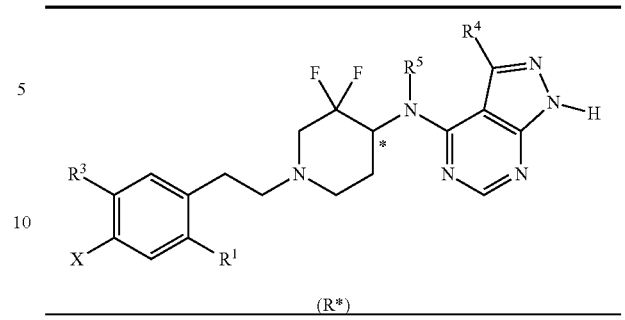

(R*)

| compound | X | R¹ | R³ | R⁴ | R⁵ |
|---|---|---|---|---|---|
| E1-1.1 | H | H | H | H | H |
| E1-1.2 | F | H | H | H | H |
| E1-1.3 | Cl | H | H | H | H |
| E1-1.4 | CH₃ | H | H | H | H |
| E1-1.5 | CF₃ | H | H | H | H |
| E1-1.6 | CF₂H | H | H | H | H |
| E1-1.7 | CH₂F | H | H | H | H |
| E1-1.8 | CH₂CH₃ | H | H | H | H |
| E1-1.9 | cyclopropyl | H | H | H | H |
| E1-1.10 | CH₃O | H | H | H | H |
| E1-1.11 | CF₃O | H | H | H | H |
| E1-1.12 | CHF₂O | H | H | H | H |
| E1-1.13 | SCH₃ | H | H | H | H |
| E1-1.14 | CN | H | H | H | H |
| E1-1.15 | F | F | H | H | H |
| E1-1.16 | Cl | F | H | H | H |
| E1-1.17 | CH₃ | F | H | H | H |
| E1-1.18 | CF₃ | F | H | H | H |
| E1-1.19 | CF₂H | F | H | H | H |
| E1-1.20 | CH₂F | F | H | H | H |
| E1-1.21 | CH₂CH₃ | F | H | H | H |
| E1-1.22 | cyclopropyl | F | H | H | H |
| E1-1.23 | F | Cl | H | H | H |
| E1-1.24 | Cl | Cl | H | H | H |
| E1-1.25 | CH₃ | Cl | H | H | H |
| E1-1.26 | CF₃ | Cl | H | H | H |
| E1-1.27 | cyclopropyl | Cl | H | H | H |
| E1-1.28 | F | CH₃ | H | H | H |
| E1-1.29 | Cl | CH₃ | H | H | H |
| E1-1.30 | CH₃ | CH₃ | H | H | H |
| E1-1.31 | CF₃ | CH₃ | H | H | H |
| E1-1.32 | cyclopropyl | CH₃ | H | H | H |
| E1-1.33 | CF₃ | H | H | H | CH₃ |
| E1-1.34 | CF₃ | H | H | CH₃ | H |
| E1-1.35 | H | F | F | H | H |
| E1-1.36 | H | H | CF₃ | H | H |

TABLE 1.E2

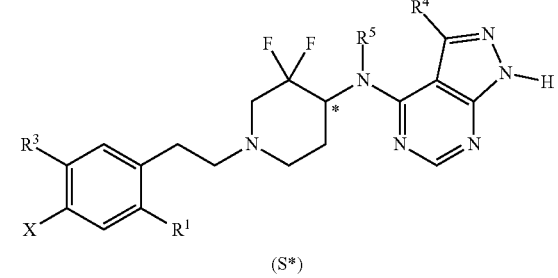

(S*)

| compound | X | R¹ | R³ | R⁴ | R⁵ |
|---|---|---|---|---|---|
| E2-1.1 | H | H | H | H | H |
| E2-1.2 | F | H | H | H | H |
| E2-1.3 | Cl | H | H | H | H |
| E2-1.4 | CH₃ | H | H | H | H |
| E2-1.5 | CF₃ | H | H | H | H |

TABLE 1.E2-continued

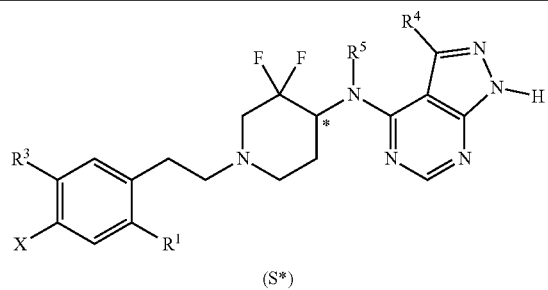

(S*)

| compound | X | R¹ | R³ | R⁴ | R⁵ |
|---|---|---|---|---|---|
| E2-1.6 | CF₂H | H | H | H | H |
| E2-1.7 | CH₂F | H | H | H | H |
| E2-1.8 | CH₂CH₃ | H | H | H | H |
| E2-1.9 | cyclopropyl | H | H | H | H |
| E2-1.10 | CH₃O | H | H | H | H |
| E2-1.11 | CF₃O | H | H | H | H |
| E2-1.12 | CHF₂O | H | H | H | H |
| E2-1.13 | SCH₃ | H | H | H | H |
| E2-1.14 | CN | H | H | H | H |
| E2-1.15 | F | F | H | H | H |
| E2-1.16 | Cl | F | H | H | H |
| E2-1.17 | CH₃ | F | H | H | H |
| E2-1.18 | CF₃ | F | H | H | H |
| E2-1.19 | CF₂H | F | H | H | H |
| E2-1.20 | CH₂F | F | H | H | H |
| E2-1.21 | CH₂CH₃ | F | H | H | H |
| E2-1.22 | cyclopropyl | F | H | H | H |
| E2-1.23 | F | Cl | H | H | H |
| E2-1.24 | Cl | Cl | H | H | H |
| E2-1.25 | CH₃ | Cl | H | H | H |
| E2-1.26 | CF₃ | Cl | H | H | H |
| E2-1.27 | cyclopropyl | Cl | H | H | H |
| E2-1.28 | F | CH₃ | H | H | H |
| E2-1.29 | Cl | CH₃ | H | H | H |
| E2-1.30 | CH₃ | CH₃ | H | H | H |
| E2-1.31 | CF₃ | CH₃ | H | H | H |
| E2-1.32 | cyclopropyl | CH₃ | H | H | H |
| E2-1.33 | CF₃ | H | H | H | CH₃ |
| E2-1.34 | CF₃ | H | H | CH₃ | H |
| E2-1.35 | H | F | F | H | H |
| E2-1.36 | H | H | CF₃ | H | H |

TABLE 2.E1

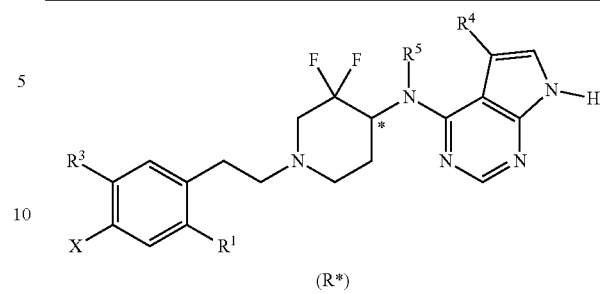

(R*)

| compound | X | R¹ | R³ | R⁴ | R⁵ |
|---|---|---|---|---|---|
| E1-2.1 | H | H | H | H | H |
| E1-2.2 | F | H | H | H | H |
| E1-2.3 | Cl | H | H | H | H |
| E1-2.4 | CH₃ | H | H | H | H |
| E1-2.5 | CF₃ | H | H | H | H |
| E1-2.6 | CF₂H | H | H | H | H |
| E1-2.7 | CH₂F | H | H | H | H |
| E1-2.8 | CH₂CH₃ | H | H | H | H |
| E1-2.9 | cyclopropyl | H | H | H | H |
| E1-2.10 | CH₃O | H | H | H | H |
| E1-2.11 | CF₃O | H | H | H | H |

TABLE 2.E1-continued

| compound | X | R¹ | R³ | R⁴ | R⁵ |
|---|---|---|---|---|---|
| E1-2.12 | CHF₂O | H | H | H | H |
| E1-2.13 | SCH₃ | H | H | H | H |
| E1-2.14 | CN | H | H | H | H |
| E1-2.15 | F | F | H | H | H |
| E1-2.16 | Cl | F | H | H | H |
| E1-2.17 | CH₃ | F | H | H | H |
| E1-2.18 | CF₃ | F | H | H | H |
| E1-2.19 | CF₂H | F | H | H | H |
| E1-2.20 | CH₂F | F | H | H | H |
| E1-2.21 | CH₂CH₃ | F | H | H | H |
| E1-2.22 | cyclopropyl | F | H | H | H |
| E1-2.23 | F | Cl | H | H | H |
| E1-2.24 | Cl | Cl | H | H | H |
| E1-2.25 | CH₃ | Cl | H | H | H |
| E1-2.26 | CF₃ | Cl | H | H | H |
| E1-2.27 | cyclopropyl | Cl | H | H | H |
| E1-2.28 | F | CH₃ | H | H | H |
| E1-2.29 | Cl | CH₃ | H | H | H |
| E1-2.30 | CH₃ | CH₃ | H | H | H |
| E1-2.31 | CF₃ | CH₃ | H | H | H |
| E1-2.32 | cyclopropyl | CH₃ | H | H | H |
| E1-2.33 | CF₃ | H | H | H | CH₃ |
| E1-2.34 | CF₃ | H | H | CH₃ | H |
| E1-2.35 | H | F | F | H | H |
| E1-2.36 | H | H | CF₃ | H | H |

TABLE 2.E2

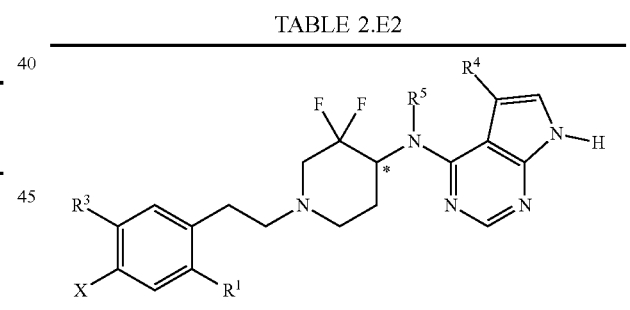

(S*)

| compound | X | R¹ | R³ | R⁴ | R⁵ |
|---|---|---|---|---|---|
| E2-2.1 | H | H | H | H | H |
| E2-2.2 | F | H | H | H | H |
| E2-2.3 | Cl | H | H | H | H |
| E2-2.4 | CH₃ | H | H | H | H |
| E2-2.5 | CF₃ | H | H | H | H |
| E2-2.6 | CF₂H | H | H | H | H |
| E2-2.7 | CH₂F | H | H | H | H |
| E2-2.8 | CH₂CH₃ | H | H | H | H |
| E2-2.9 | cyclopropyl | H | H | H | H |
| E2-2.10 | CH₃O | H | H | H | H |
| E2-2.11 | CF₃O | H | H | H | H |
| E2-2.12 | CHF₂O | H | H | H | H |
| E2-2.13 | SCH₃ | H | H | H | H |
| E2-2.14 | CN | H | H | H | H |
| E2-2.15 | F | F | H | H | H |
| E2-2.16 | Cl | F | H | H | H |
| E2-2.17 | CH₃ | F | H | H | H |

TABLE 2.E2-continued (S*)

| compound | X | R¹ | R³ | R⁴ | R⁵ |
|---|---|---|---|---|---|
| E2-2.18 | $CF_3$ | F | H | H | H |
| E2-2.19 | $CF_2H$ | F | H | H | H |
| E2-2.20 | $CH_2F$ | F | H | H | H |
| E2-2.21 | $CH_2CH_3$ | F | H | H | H |
| E2-2.22 | cyclopropyl | F | H | H | H |
| E2-2.23 | F | Cl | H | H | H |
| E2-2.24 | Cl | Cl | H | H | H |
| E2-2.25 | $CH_3$ | Cl | H | H | H |
| E2-2.26 | $CF_3$ | Cl | H | H | H |
| E2-2.27 | cyclopropyl | Cl | H | H | H |
| E2-2.28 | F | $CH_3$ | H | H | H |
| E2-2.29 | Cl | $CH_3$ | H | H | H |
| E2-2.30 | $CH_3$ | $CH_3$ | H | H | H |
| E2-2.31 | $CF_3$ | $CH_3$ | H | H | H |
| E2-2.32 | cyclopropyl | $CH_3$ | H | H | H |
| E2-2.33 | $CF_3$ | H | H | H | $CH_3$ |
| E2-2.34 | $CF_3$ | H | H | $CH_3$ | H |
| E2-2.35 | H | F | F | H | H |
| E2-2.36 | H | H | $CF_3$ | H | H |

Pharmacology

Glutamate (GLU) is a fundamental excitatory neurotransmitter in the mammalian brain and central nervous system (CNS). The effects of this endogenous neurotransmitter are mediated through binding to and activation of GLU to glutamate receptors (GLURs), which are broadly classified into metabotropic G-protein coupled (mGluRs) and ligand gated ion channels or ionotropic GluRs. The ionotropic GLURs are pharmacologically classified into three main types based on the actions of selective receptor agonists: NMDA (N-methyl D-aspartate selective), KA (kainic acid selective) and AMPA (α-amino-3-hydroxy-5-methyl-4-isoxazolepropionic acid) receptors whose structure and pharmacological function has been recently reviewed in detail (S. F. Traynelis et al. *Pharmacology Reviews*, 2010, 62, 405-496). Electrophysiology studies have demonstrated NMDARs to be cation ion channels that are subject to voltage-dependent channel block by endogenous $Mg^{2+}$. Activation of NMDARs by glutamate in the presence of glycine as a co-agonist results in opening of the receptor ion channel. This in turn allows for the flow of $Na^+$ and $Ca^{2+}$ into the cell generating excitatory postsynaptic potentials (EPSPs) and $Ca^{2+}$ activated second messenger signaling pathways in neurons. By virtue of their permeability to $Ca^{2+}$, activation of NMDA receptors regulates long-term changes in neuronal communication such as learning and memory and synaptic plasticity.

Since the original pharmacological characterization with selective ligands, molecular biology and cloning studies have enabled detailed characterization of NMDARs at the molecular level (Paoletti et al., 2013, *Nat. Rev. Neurosci.* 14:383-400). Thus, NMDARs are heterotetramers comprised of two NR1 subunits and two NR2 subunits. NR1 subunits contain the binding site for the glycine co-agonist while NR2 subunits contain the binding site for glutamate. The existence of multiple splice variants for NR1 and four isoforms of NR2 (NR2A, NR2B, NR2C and NR2D) from different genes results in a diverse molecular array and of NMDARs. The pharmacological and electrophysiological properties of NMDARs vary depending on the particular NR1 isoform and NR2 subtype composition. Furthermore, the NR2 subtype isoforms are differentially expressed across cell types and brain regions. Thus, compounds that interact selectivity with NR2 subunits can exert specific pharmacological effects in particular brain regions and have potential to treat CNS diseases with a high degree of specificity and selectivity (e.g. vz side effects). For example the low expression of the NR2B subtype in the cerebellum relative to other brain structures (Cull-Candy et al., 1998, *Neuropharmacol.* 37:1369-1380) indicated lower motor side effects for this subtype.

NMDA receptor antagonism has been extensively investigated for its potential to treat a variety of CNS diseases including stroke, epilepsy, pain, depression Parkinson's Disease and Alzheimer's disease (Paoletti et al., Nat. Rev. Neurosci 14:383-400; Sancora, 2008, *Nature Rev. Drug Disc.*, 7, 426-437). The NMDA receptor offers a number of pharmacological entry points for developing receptor inhibitors. Direct blockers of the NMDAR ion channel pore represent one family of antagonist compounds for which efficacy could be demonstrated in diverse in vitro and in vivo CNS disease models including, epilepsy, pain and neurodegeneration/stroke. However, compounds from this class, as exemplified by phencyclidine (PCP), MK-801, and ketamine, are generally categorized as unselective across the diversity of NMDA receptor subtypes.

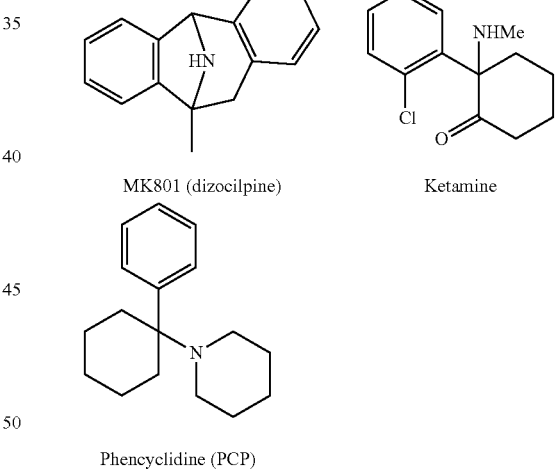

MK801 (dizocilpine)   Ketamine

Phencyclidine (PCP)

In humans unselective, high-affinity NMDAR antagonists have generally been associated with serious clinical side effects including hallucinations, dysphoria and lack of coordination. Nevertheless, ketamine, an intravenous drug originally approved for use in anesthesia (Haas et. al, 1992, *Anesthesia Prog.*, 39, 61-68) has more recently demonstrated clinical efficacy as an antidepressant therapy (Katalinic et al. 2013, Aust. N. Z. *J. Psychiatry*, 47, 710-727). The antidepressant action of acute ketamine therapy has an essentially immediate onset compared to approximately six weeks required for standard serotonin reuptake inhibitor (SSRI) drug therapy. Thus, intravenous administration of the drug has shown rapid onset and prolonged efficacy that can be maintained with continued intermittent administrations (Zarate et al., 2006, *Arch. Gen. Psychiatry* 63, 856-864). Finally, ketamine has been shown to be effective in cases of depression resistant to standard drug therapies (Murrough et al., 2013, *American J. Psychiatry*, 170, 1134-1142) including bipolar depression (Zarate et al. 2012, *Biol. Psychiatry*, 71, 939-946). However, as an intravenous drug with serious side effects (Gianni et. al 1985, *Psychiatric Medicine,* 3, 197-217; Curran et al 2000, *Addiction*, 95, 575-590) and potential chronic toxicity (Hardy et al., 2012, *J. Clin. Oncol.* 30:3611-3617; Noppers et al., 2011, *Pain* 152:2173-2178) ketamine therapy is of limited utility and restricted to acute or intermittent administration. To have broader scope of application and utility as a therapy for depression and other CNS diseases, orally active selective NMDA antagonists with reduced side effects are needed that can be administered chronically.

Ifenprodil, a vasodilator α₁-adrenergic antagonist drug, was determined to have a novel allosteric modulator mechanism of action at the NR2B NMDA receptor subtype (Reynolds et al. 1989, *Mol. Pharmacol.*, 36, 758-765). This new mechanism held promise for a new class of NMDA antagonist drugs having therapeutic efficacy without the limiting side effects of subtype unselective ion channel blockers. Following this discovery, NR2B selective antagonist analogs of ifenprodil (Borza et al., 2006, *Current Topics in Medicinal Chemistry*, 6, 687-695; Layton et al. *Current Topics in Medicinal Chemistry*, 6, 697-709) optimized against the undesirable α₁-adrenergic activity included Ro-25,6981 (Fischer et al. 1997, *J. Pharmacol. Exp. Ther.,* 283, 1285-1292) and CP-101,606 otherwise known as traxoprodil (Chenard et al. 1995, *Journal of Medicinal Chemistry*, 38, 3138-3145; Menniti et al. 1998, *CNS Drug Reviews.,* 4, 307-322). In a clinical study, CP-101,606 evidenced antidepressant activity in humans after intravenous administration with a favorable dissociative side effect profile relative to unselective NMDA antagonists (Preskorn et al. 2008, *Journal of Clinical Psychopharmacology*, 28, 631-637). However, CP-101,606 has suboptimal pharmacokinetic properties and requires limiting intravenous administration. For CP-101,606 a slow intravenous infusion protocol was required for optimal results in the aforementioned antidepressant clinical study (Preskorn et al. 2008, *Journal of Clinical Psychopharmacology*, 28, 631-637).

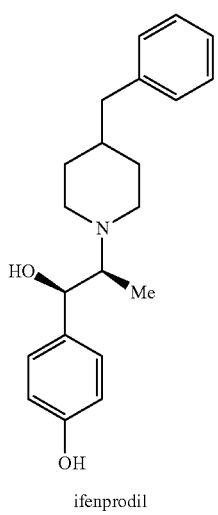

ifenprodil

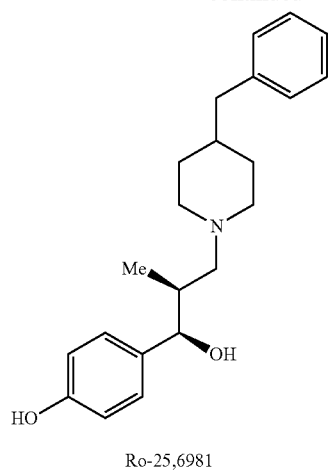

Ro-25,6981

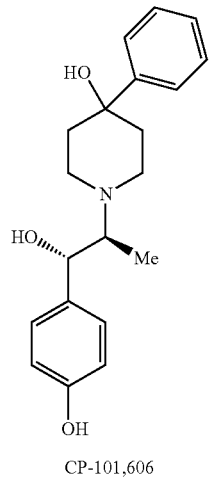

CP-101,606

Other NR2B antagonists which have been described as reviewed by B. Ruppa et al. (K. B. Ruppa et al., *Annual Reports in Medicinal Chemistry* 2012, 47:89-103) include MK0657 (J. A. McCauley et al., 3ʳᵈ *Anglo-Swedish Medicinal Chemistry Symposium*, Åre, Sweden, Mar. 11-14, 2007; L. Mony et al., *British J. of Pharmacology* 2009, 157:1301-1317; see also Intl. Appl. Publ. No. WO 2004/108705; U.S. Pat. No. 7,592,360) and compounds of formula LX (Intl. Appl. Publ. No. WO 2006/113471), below, including the specific analog LX-1 depicted below.

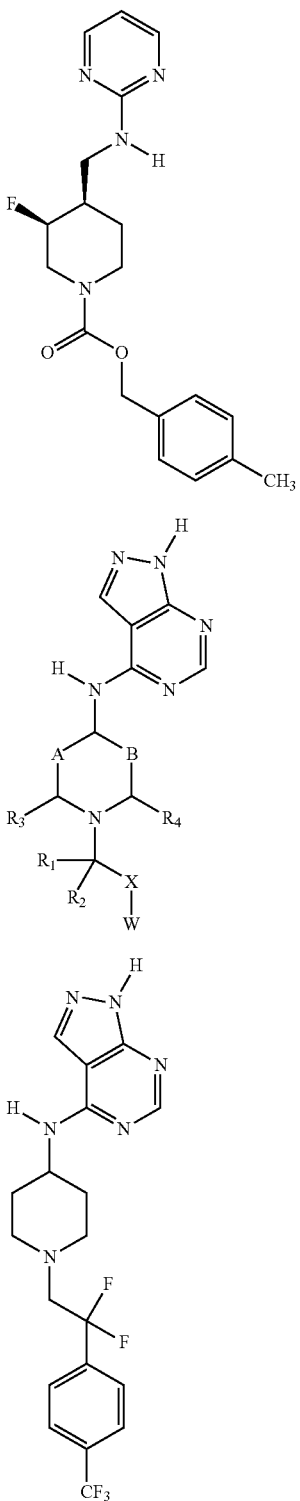

MK0657

LX

LX-1

The difficulties presented by NR2B antagonists having basic amine moieties with regard to overcoming hERG and CYP2D6 safety liabilities while maintaining NR2B in vitro and in vivo potency are well established as noted by Kawai et al. (M. Kawai et al., *Bioorganic and Medicinal Chem. Lett.* 2007, v17:5533-5536) and Brown et al. (Brown et al., *Bioorganic and Medicinal Chem. Lett.* 2011, v21:3399-3403). Compound inhibition of hERG channels and associated QT prolongation in the electrocardiograph (ECG) represents a well recognized serious human cardiovascular safety risk (Hancox et al., *Molecular Pharmacology* 2008, 73:1592-1595). QT prolongation can lead to torsades de pointer (TdP) cardiac arrhythmia which can degenerate into ventricular tachycardia and sudden death.

Compound inhibition of human metabolic cytochrome P-450 enzymes including CYP2D6 represents a risk with regard to human drug safety due to drug-drug interactions (*Drug Metabolism Handbook: Concepts and Applications*, ed. Ala F. Nassar copyright 2009 Wiley & Sons, Hoboken, N.J.). Thus, the clearance of drugs that are substrates of CYP2D6 can be reduced by compounds that inhibit CYP2D6. The result can be toxic or side effect overload due to accumulation of the given CYP2D6 drug substrate. CNS drugs including antidepressant drugs feature prominently among the established CYP2D6 substrates. Therefore, CYP2D6 inhibition is highly undesirable for an NR2B antagonist drug especially given the common application of comedications or polypharmacy in CNS indications including depression. Examples of CY2D6 substrates include antidepressants from the SSRI class such as fluoxetine, paroxetine, and fluvoxamine, duloxetine, an antidepressants from the SSNI class, numerous antipsychotics including haloperidol, risperidone and aripiperazole, numerous beta-blocker antihypertensives including metaprolol, propranolol, timolol and alprenolol and the Alzheimer's disease anticholinesterase inhibitor drug donepezil (Flockhart D A (2007). "Drug Interactions: Cytochrome P450 Drug Interaction Table", Indiana University School of Medicine, accessed at <<http://medicine.iupui.edu/clinpharm/ddis/>> on Jan. 22, 2015).

MK0657 and closely related analogs (Liverton et al., *J. Med. Chem.* 2007, v50:807-819) represent an improved generation of NR2B antagonists with respect to human oral bioavailability. However, drug-related systolic as well as diastolic blood pressure elevation cardiovascular side effects for MK0657 after oral dosing have been described in a published clinical efficacy trial study in patients with Parkinson's Disease (Addy et al., *J. Clin. Pharm.* 2009, v49: 856-864). Similar blood pressure effects were reported to have also been observed after single doses of MK0657 in safety studies with healthy elderly subjects. Compound LX-1 demonstrates oral bioavailability in animals and lacks a phenolic group which can compromise oral bioavailability in humans. However, not inconsistent with other NR2B antagonists having basic amine moieties, compound LX-1, which has a basic piperidine nitrogen atom, notwithstanding the basicity-attenuating vicinal difluoro moiety beta to this nitrogen exhibits human hERG channel inhibition with an $IC_{50}$<10 µM (~4.5 µM), and exhibits human CYP2D6 metabolic enzyme inhibition activity ($IC_{50}$~1.0 µM).

For broad scope of application and safe human use, improved NR2B selective antagonists are needed, as noted in a recent review (K. B. Ruppa et al., *Annual Reports in Medicinal Chemistry* 2012, 47:89-103). There is a need for NR2B antagonist compounds which are improved in one or more aspects exemplified by pharmacokinetic, absorption, metabolism, excretion (ADME, e.g., oral activity), improved efficacy, off-target activity, improved therapeutic safety index relative and compatibility with chronic oral therapy.

Provided chemical entities are antagonists of the NR2B receptor which have technical advantages with regard to one or more pharmaceutical drug properties, such as oral bioavailability, pharmacokinetic parameters, ADME properties (e.g., CYP inhibition), cardiac ion channel (e.g., hERG) activity and other non-NMDA off-target side effect mediating receptors. In some embodiments, the present invention encompasses the discovery that a provided chemical entity can exhibit low human CYP2D6 inhibition and/or low hERG inhibition while exhibiting potent human NR2B receptor inhibition antagonism, and as such is favorable for application in humans. This discovery is particularly surprising inasmuch as the provided chemical entities have a basic piperidine nitrogen analogous to that of LX-1, yet the repositioning of the vicinal difluoro group from beta to the piperidine nitrogen in the side chain to beta to the piperidine nitrogen on the piperidine ring imparts these compounds with the aforementioned technical advantages.

In some embodiments, a provided chemical entity has NR2B functional NMDA receptor selectivity versus NR2A ("NR2B selectivity", determined as the ratio NR2A $IC_{50}$/NR2B $IC_{50}$, in which the $IC_{50}$ values are measured according to the procedure of Example 2.1)≥400. In some embodiments, a provided chemical entity has NR2B selectivity≥350. In some embodiments, a provided chemical entity has NR2B selectivity≥300. In some embodiments, a provided chemical entity has NR2B selectivity≥250. In some embodiments, a provided chemical entity has NR2B selectivity≥200. In some embodiments, a provided chemical entity has NR2B selectivity≥150. In some embodiments, a provided chemical entity has NR2B selectivity≥100. In some embodiments, a provided chemical entity has NR2B selectivity≥50.

In some embodiments, a provided chemical entity has hERG activity (determined as hERG $IC_{50}$ measured according to the procedure of Example 2.2)≥5 μM. In some embodiments, a provided chemical entity has hERG $IC_{50}$≥10 μM. In some embodiments, a provided chemical entity has hERG $IC_{50}$≥15 μM. In some embodiments, a provided chemical entity has hERG $IC_{50}$≥20 μM. In some embodiments, a provided chemical entity has hERG inhibition @10 μM<60%.

In some embodiments, a provided chemical entity has NR2B functional antagonist activity (determined as NR2B $IC_{50}$ measured according to the procedure of Example 2.1) ≤110 nM and hERG activity (determined as hERG $IC_{50}$ measured according to the procedure of Example 2.2)≥5 μM. In some embodiments, a provided chemical entity has NR2B $IC_{50}$≤110 nM and hERG $IC_{50}$≥10 μM. In some embodiments, a provided chemical entity has NR2B $IC_{50}$≤110 nM and hERG $IC_{50}$≥15 μM. In some embodiments, a provided chemical entity has NR2B $IC_{50}$≤110 nM and hERG $IC_{50}$≥20 μM. In some embodiments, a provided chemical entity has NR2B $IC_{50}$≤110 nM and hERG inhibition @10 μM<60%. In some embodiments, a provided chemical entity has NR2B $IC_{50}$≤80 nM and hERG $IC_{50}$≥5 μM. In some embodiments, a provided chemical entity has NR2B $IC_{50}$≤80 nM and hERG $IC_{50}$≥10 μM. In some embodiments, a provided chemical entity has NR2B $IC_{50}$≤80 nM and hERG $IC_{50}$≥15 μM. In some embodiments, a provided chemical entity has NR2B $IC_{50}$≤80 nM and hERG $IC_{50}$≥20 μM. In some embodiments, a provided chemical entity has NR2B $IC_{50}$≤50 nM and hERG $IC_{50}$≥5 μM. In some embodiments, a provided chemical entity has NR2B $IC_{50}$≤50 nM and hERG $IC_{50}$≥10 μM. In some embodiments, a provided chemical entity has NR2B $IC_{50}$≤50 nM and hERG $IC_{50}$≥15 μM. In some embodiments, a provided chemical entity has NR2B $IC_{50}$≤50 nM and hERG $IC_{50}$≥20 μM.

In some embodiments, a provided chemical entity has NR2B functional antagonist activity (determined as NR2B $IC_{50}$ measured according to the procedure of Example 2.1) ≤110 nM and CYP2D6 inhibition (measured as CYP2D6 $IC_{50}$ determined according to the procedure of Example 2.3)≥2 μM. In some embodiments, a provided chemical entity has NR2B $IC_{50}$≤110 nM and CYP2D6 $IC_{50}$≥3 μM. In some embodiments, a provided chemical entity has NR2B $IC_{50}$≤110 nM and CYP2D6 $IC_{50}$≥4 μM. In some embodiments, a provided chemical entity has NR2B $IC_{50}$≤110 nM and CYP2D6 $IC_{50}$≥5 μM. In some embodiments, a provided chemical entity has NR2B $IC_{50}$≤110 nM and CYP2D6 $IC_{50}$≥10 μM. In some embodiments, a provided chemical entity has NR2B $IC_{50}$≤110 nM and CYP2D6 $IC_{50}$≥15 μM. In some embodiments, a provided chemical entity has NR2B $IC_{50}$≤110 nM and CYP2D6 $IC_{50}$≥20 μM. In some embodiments, a provided chemical entity has NR2B $IC_{50}$≤110 nM and CYP2D6 $IC_{50}$≥25 μM. In some embodiments, a provided chemical entity has NR2B $IC_{50}$≤110 nM and CYP2D6 $IC_{50}$≥30 μM. In some embodiments, a provided chemical entity has NR2B $IC_{50}$≤80 nM and CYP2D6 $IC_{50}$≥2 μM. In some embodiments, a provided chemical entity has NR2B $IC_{50}$≤80 nM and CYP2D6 $IC_{50}$≥3 μM. In some embodiments, a provided chemical entity has NR2B $IC_{50}$≤80 nM and CYP2D6 $IC_{50}$≥4 μM. In some embodiments, a provided chemical entity has NR2B $IC_{50}$≤80 nM and CYP2D6 $IC_{50}$≥5 μM. In some embodiments, a provided chemical entity has NR2B $IC_{50}$≤80 nM and CYP2D6 $IC_{50}$≥10 μM. In some embodiments, a provided chemical entity has NR2B $IC_{50}$≤80 nM and CYP2D6 $IC_{50}$≥15 μM. In some embodiments, a provided chemical entity has NR2B $IC_{50}$≤80 nM and CYP2D6 $IC_{50}$≥20 μM. In some embodiments, a provided chemical entity has NR2B $IC_{50}$≤80 nM and CYP2D6 $IC_{50}$≥25 μM. In some embodiments, a provided chemical entity has NR2B $IC_{50}$≤80 nM and CYP2D6 $IC_{50}$≥30 μM. In some embodiments, a provided chemical entity has NR2B $IC_{50}$≤50 nM and CYP2D6 $IC_{50}$≥2 μM. In some embodiments, a provided chemical entity has NR2B $IC_{50}$≤50 nM and CYP2D6 $IC_{50}$≥3 μM. In some embodiments, a provided chemical entity has NR2B $IC_{50}$≤50 nM and CYP2D6 $IC_{50}$≥4 μM. In some embodiments, a provided chemical entity has NR2B $IC_{50}$≤50 nM and CYP2D6 $IC_{50}$≥5 μM. In some embodiments, a provided chemical entity has NR2B $IC_{50}$≤50 nM and CYP2D6 $IC_{50}$≥10 μM. In some embodiments, a provided chemical entity has NR2B $IC_{50}$≤50 nM and CYP2D6 $IC_{50}$≥15 μM. In some embodiments, a provided chemical entity has NR2B $IC_{50}$≤50 nM and CYP2D6 $IC_{50}$≥20 μM. In some embodiments, a provided chemical entity has NR2B $IC_{50}$≤50 nM and CYP2D6 $IC_{50}$≥25 μM. In some embodiments, a provided chemical entity has NR2B $IC_{50}$≤50 nM and CYP2D6 $IC_{50}$≥30 μM.

Uses, Formulation and Administration, and Pharmaceutically Acceptable Compositions In some embodiments, the invention provides a composition comprising a chemical entity of the invention or a pharmaceutically acceptable derivative thereof and a pharmaceutically acceptable carrier, adjuvant, or vehicle. The amount of chemical entity in compositions of this invention is such that is effective to measurably inhibit NR2B, in a biological sample or in a patient. In some embodiments, the amount of chemical entity in compositions of this invention is such that is effective to measurably inhibit NR2B, in a biological sample or in a patient. In some embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the chemical entity with which it is formulated. Pharmaceutically acceptable carriers, adjuvants or vehicles that may be used in the compositions of this invention include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic ester, salt of an ester or other derivative of a chemical entity of this invention (e.g., a prodrug) that, upon administration to a recipient, is capable of providing, either directly or indirectly, a chemical entity of this invention or an inhibitorily active metabolite or residue thereof.

As used herein, the term "inhibitorily active metabolite or residue thereof" means that a metabolite or residue thereof is also an inhibitor of NR2B.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon a variety of factors, including the host treated and the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Chemical Entities and Pharmaceutically Acceptable Compositions

Human therapeutic applications of NR2B receptor antagonists have been summarized in reviews by Traynelis et al. (S. F. Traynelis et al., *Pharmacology Reviews*, 2010, 62:405-496), Beinat et al. (C. Beinat et al., *Current Medicinal Chemistry*, 2010, 17:4166-4190) and Mony et al. (L. Mony et al., *British J. of Pharmacology*, 2009, 157:1301-1317). Antagonism of NR2B can be useful in the treatment of diseases and disorders including depression, pain, Parkinson's disease, Huntington's disease, Alzheimer's disease, cerebral ischaemia, traumatic brain injury, epilepsy and migraine.

The activity of a chemical entity utilized in this invention as an antagonist of NR2B or a treatment for a disease or disorder of the central nervous system (CNS) may be assayed in vitro or in vivo. An in vivo assessment of the efficacy of the compounds of the invention may be made using an animal model of a disease or disorder of the CNS, e.g., a rodent or primate model. Cell-based assays may be performed using, e.g., a cell line isolated from a tissue that expresses NR2B, or a cell line that recombinantly expresses NR2B. Additionally, biochemical or mechanism-based assays, e.g., measuring cAMP or cGMP levels, Northern blot, RT-PCR, etc., may be performed. In vitro assays include assays that determine cell morphology, protein expression, and/or the cytotoxicity, enzyme inhibitory activity, and/or the subsequent functional consequences of treatment of cells with chemical entities of the invention. Alternate in vitro assays quantify the ability of the inhibitor to bind to protein or nucleic acid molecules within the cell. Inhibitor binding may be measured by radiolabelling the inhibitor prior to binding, isolating the inhibitor/target molecule complex and determining the amount of radiolabel bound. Alternatively, inhibitor binding may be determined by running a competition experiment where new inhibitors are incubated with purified proteins or nucleic acids bound to known radioligands. Detailed conditions for assaying a compound utilized in this invention as an antagonist of NR2B are set forth in the Examples below. The aforementioned assays are exemplary and not intended to limit the scope of the invention. A person skilled in the art can appreciate that modifications can be made to conventional assays to develop equivalent assays that obtain the same result.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The chemical entities and compositions, according to the method of the present invention, may be administered using any amount and any route of administration effective for treating or lessening the severity of a CNS disease or disorder.

In some embodiments, the chemical entities and compositions, according to the method of the present invention, may be administered using any amount and any route of administration effective for treating or lessening the severity of a disease or disorder associated with NR2B.

In some embodiments, the chemical entities and compositions, according to the method of the present invention, may be administered using any amount and any route of administration effective for treating or lessening the severity of a CNS disease or disorder.

In some embodiments, the disease or disorder is depression with or without concomitant anxiety disorder, e.g., single episode and recurrent depressive disorder, dysthymic disorder, treatment-resistant depression (TRD, i.e., major depressive disorder that has not responded to other drug therapies).

In some embodiments, the disease or disorder is an acute affective disorder, e.g., selected from bipolar disorders including bipolar I and bipolar II manic disorders.

In some embodiments, the disease or disorder is pain, e.g., selected from pain states arising from a variety of sources including inflammation, nerve damage, diabetic neuropathy and post-herpetic neuralgia. In some embodiments, the disease or disorder is associated with intractable, such as migraine, fibromyalgia, and trigeminal neuralgia.

In some embodiments, the disease or disorder is selected from sleep disorders and their sequelae including insomnia, narcolepsy and idiopathic hypersomnia.

In some embodiments, the disease or disorder is selected from CNS disorders characterized by neuronal hyperexcitablity, such as epilepsy, convulsions and other seizure disorders.

In some embodiments, the disease or disorder is Parkinson's disease.

In some embodiments, the disease or disorder is Huntington's disease.

In some embodiments, the disease or disorder is cognitive dysfunction associated with disorders including schizophrenia, Alzheimer's disease, fronto-temporal dementia, Pick's disease, Lewy body disease, and other senile dementias (e.g., vascular dementia).

In some embodiments, the present invention provides a method of treating a disorder described herein, comprising administering a chemical entity of the invention in conjunction with one or more pharmaceutical agents. Suitable pharmaceutical agents that may be used in combination with the chemical entities of the present invention include selective serotonin reuptake inhibitors (SSRIs), e.g., in the treatment of depression; dopamine replacement therapy regimens and dopamine agonists, e.g., in the treatment of Parkinson's disease; typical antipsychotics; atypical antipsychotics; anticonvulsants; stimulants; Alzheimer's disease therapies; anti-migraine agents; and anxiolytic agents.

Suitable SSRIs include citalopram, dapoxetine, escitalopram, fluoxetine, fluvoxamine, indalpine, paroxetine, sertraline, vilazodone and zimelidine.

Suitable dopamine replacement therapy regimens include replacement of L-DOPA with a DOPA decarboxylase inhibitor such as carbidopa.

Suitable dopamine receptor agonists include aplindore, apomorphine, bromocriptine, cabergoline, ciladopa, dihydroergocryptine, lisuride, pardoprunox, pergolide, piribedil, pramipexole, ropinirole and rotigotine.

Suitable typical antipsychotics include chlorpromazine, thioridazine, mesoridazine, levomepromazine, loxapine, molindone, perphenazine, thiothixene, trifluoperazine, haloperidol, fluphenazine, droperidol, zuclopenthixol, flupentixol and prochlorperazine.

Suitable atypical antipsychotics include amisulpride, aripiprazole, asenapine, blonanserin, clotiapine, clozapine, iloperidone, Ilurasidone, mosapramine, olanzapine, paliperidone, perospirone, quetiapine, remoxipride, risperidone, sertindole, sulpiride, ziprasidone, zotepine, bifeprunox, pimavanserin and vabicaserin.

Suitable anticonvulsants include carbamazepine, lamotrigine, topiramate and divalproex.

Suitable stimulants include Adderall (amphetamine, dextroamphetamine mixed salts), methylphenidate, dextroamphetamine, dexmethylphenidate and lisdexamfetamine.

Suitable Alzheimer's disease therapies include acetylcholinesterase inhibitors such as rivastigmine, donepezil, galanthamine and huperazine; alpha-7 nicotinic agonists such as encenicline; and drugs that reduce Aβ42 such as BACE inhibitors, gamma secretase modulators and beta amyloid peptide antibodies.

Suitable anti-migraine drugs include ergotamine and 5-HT1D agonist triptans such as sumitriptan.

Suitable anxiolytic drugs include benzodiazepine receptor modulators such as diazepam, alprazolam, lorazepam and clonazepam.

Other suitable agents for use in conjunction with a chemical entity of the invention include memantine and modafinil.

The exact amount required will vary from subject to subject, depending on the species, age, and general condition of the subject, the severity of the infection, the particular agent, its mode of administration, and the like. The chemical entities of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the chemical entities and compositions of the present invention will be decided by the attending physician within the scope of sound medical judgment. The specific effective dose level for any particular patient or organism will depend upon a variety of factors including the disorder being treated and the severity of the disorder; the activity of the specific chemical entity employed; the specific composition employed; the age, body weight, general health, sex and diet of the patient; the time of administration, route of administration, and rate of excretion of the specific chemical entity employed; the duration of the treatment; drugs used in combination or coincidental with the specific chemical entity employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the chemical entities of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a chemical entity of the present invention, it is often desirable to slow the absorption of the chemical entity from subcutaneous or intramuscular injection. This may be accomplished by the use of a liquid suspension of crystalline or amorphous material with poor water solubility. The rate of absorption of the chemical entity then depends upon its rate of dissolution that, in turn, may depend upon crystal size and crystalline form. Alternatively, delayed absorption of a parenterally administered chemical entity form is accomplished by dissolving or suspending the chemical entity in an oil vehicle. Injectable depot forms are made by forming microencapsule matrices of the chemical entity in biodegradable polymers such as polylactide-polyglycolide. Depending upon the ratio of chemical entity to polymer and the nature of the particular polymer employed, the rate of chemical entity release can be controlled. Examples of other biodegradable polymers include poly(orthoesters) and poly(anhydrides). Depot injectable formulations are also prepared by entrapping the chemical entity in liposomes or microemulsions that are compatible with body tissues.

Compositions for rectal or vaginal administration are preferably suppositories which can be prepared by mixing the chemical entities of this invention with suitable non-irritating excipients or carriers such as cocoa butter, polyethylene glycol or a suppository wax which are solid at ambient temperature but liquid at body temperature and therefore melt in the rectum or vaginal cavity and release the active chemical entity.

Solid dosage forms for oral administration include capsules, tablets, pills, powders, and granules. In such solid dosage forms, the active chemical entity is mixed with at least one inert, pharmaceutically acceptable carrier such as sodium citrate or dicalcium phosphate and/or a) fillers or extenders such as starches, lactose, sucrose, glucose, mannitol, and silicic acid, b) binders such as carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active chemical entities can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active chemical entity may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a chemical entity of the invention include ointments, pastes, creams, lotions, gels, powders, solutions, sprays, inhalants or patches. The active chemical entity is admixed under sterile conditions with a pharmaceutically acceptable carrier and any needed preservatives or buffers as may be required. Ophthalmic formulation, ear drops, and eye drops are also contemplated as being within the scope of the invention. Additionally, the present invention contemplates the use of transdermal patches, which have the added advantage of providing controlled delivery of a chemical entity to the body. Such dosage forms can be made by dissolving or dispensing the chemical entity in the proper medium. Absorption enhancers can also be used to increase the flux of the chemical entity across the skin. The rate can be controlled by either providing a rate controlling membrane or by dispersing the chemical entity in a polymer matrix or gel.

As used herein, the term "combination," "combined," and related terms refers to the simultaneous or sequential administration of therapeutic agents in accordance with this invention. For example, a chemical entity of the present invention may be administered with another therapeutic agent simultaneously or sequentially in separate unit dosage forms or together in a single unit dosage form. Accordingly, the present invention provides a single unit dosage form comprising a chemical entity of formula (I), an additional therapeutic agent, and a pharmaceutically acceptable carrier, adjuvant, or vehicle.

The amount of both, a provided chemical entity and additional therapeutic agent (in those compositions which comprise an additional therapeutic agent as described above), that may be combined with the carrier materials to produce a single dosage form will vary depending upon the host treated and the particular mode of administration. Preferably, compositions of this invention should be formulated so that a dosage of between 0.01-100 mg/kg body weight/day of a provided chemical entity can be administered.

In those compositions which comprise an additional therapeutic agent, that additional therapeutic agent and the chemical entity of this invention may act synergistically. Therefore, the amount of additional therapeutic agent in such compositions will be less than that required in a monotherapy utilizing only that therapeutic agent. In such compositions a dosage of between 0.01-100 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In some embodiments, the present invention provides a medicament comprising at least one chemical entity of formula (I) and a pharmaceutically acceptable carrier, adjuvant or vehicle.

In some embodiments, the present invention provides the use of a chemical entity of formula (I) in the manufacture of a medicament for the treatment of a CNS disease or disorder.

General Synthetic Methods

Chemical entities of formula I can be synthesized according to Schemes 1-7 and/or using methods known in the art.

Scheme 1

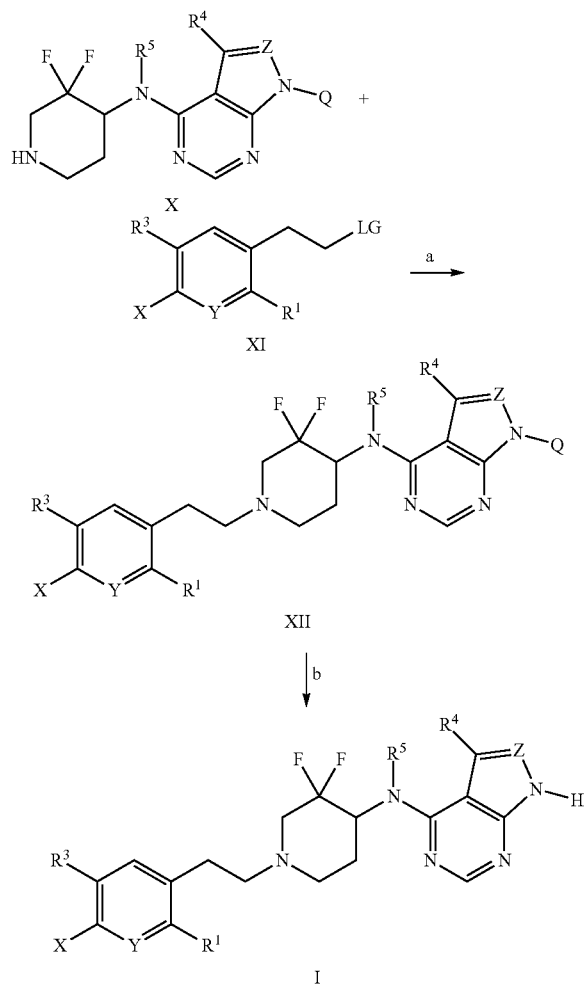

Q = H or protecting group e.g. THF, Ts
LG = a leaving group, eg. iodo or OSO₂CF₃
a. base (e.g., diisopropylethylamine), aprotic organic solvent (e.g. dichloromethane, toluene) b. conditions suitable for removal of Q protecting group (e.g., HCl solution for Q = tetrahydropyranyl, or aq. NaOH solution/heat for Q = tosyl)

In the method depicted in Scheme 1, in a first step, compounds of formula XII can be prepared by piperidine nitrogen alkylation of intermediates of general formula X, wherein Q is hydrogen or a suitable protecting group (e.g., THP (2-tetrahydropyranyl)) and $R^4$ and $R^5$ are as defined above, with intermediates of general formula XI. The LG group in alkylating intermediates of general formula XI represents an anionic leaving group such as halogen (chlorine, bromine or iodine) or a sulfonate group such as mesylate, tosylate, triflate ($OSO_2CF_3$) or nonaflate ($OSO_2CF_2CF_2CF_3$). The alkylation reaction can be conducted in a suitable aprotic solvent (e.g., $CH_2Cl_2$, toluene, THF, DMF, DMSO, $CH_3CN$) or mixed solvents at temperatures from 0° C. to 100° C. (e.g., 20-80° C.) in the presence of a suitable base (e.g., triethylamine, diisopropylethylamine). In the case where intermediates of formula X are unprotected (i.e., Q=H), the alkylation products of formula XII are compounds of formula I. Intermediates of formula XII in which Q is a protecting group can be converted to compounds of formula I using methods known in the art (e.g., when Q=2-tetrahydropyranyl using aqueous HCl in a suitable organic solvent at ambient temperature, and when Q=tosyl using aqueous NaOH in a suitable organic solvent with heating).

An alternative method of synthesizing compounds of formula I is depicted in Scheme 2.

Scheme 2

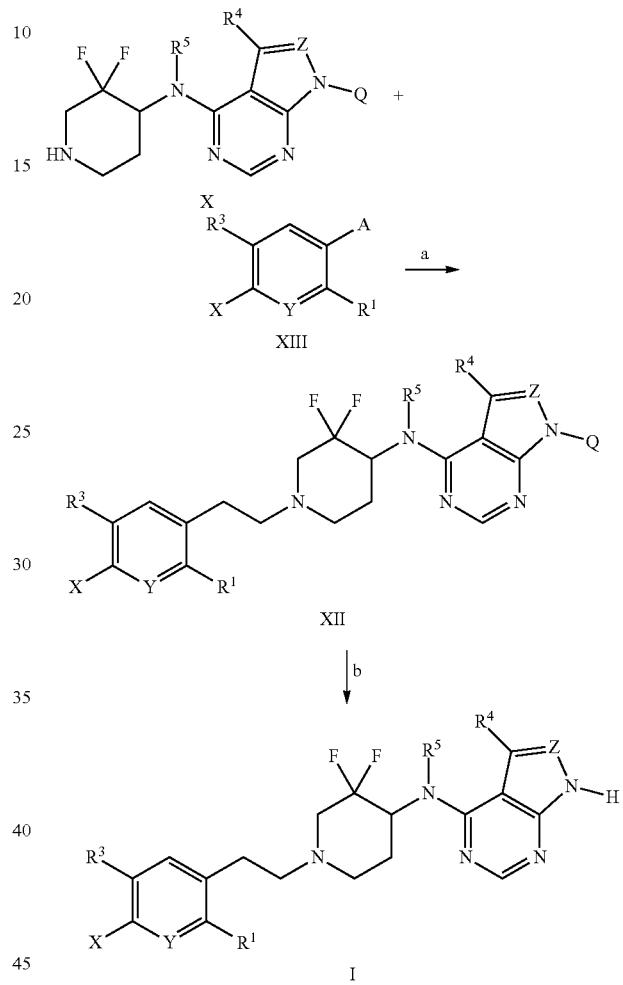

Q = H or protecting group e.g. THP, Ts
A = CH₂CHO, or CH═CH(OAlkyl)
a. reductive amination reaction conditions e.g., NaBH₃CN or NaBH(OAc)₃, organic solvent e.g., MeOH, protic (HOAc) or Lewis acid (ZnCl₂) b. conditions suitable for removal of Q protecting group (e.g., HCl solution for Q = tetrahydropyranyl, or aq. NaOH solution/heat for Q = tosyl)

In a first step, reductive amination of intermediates of formula X with intermediates of formula XIII that are either aldehydes (i.e., A=CH₂CHO) or vinylether aldehyde equivalents (i.e., A=CH═CH(O-alkyl)) yields compounds of formula XII. The reductive amination reaction can be conducted under conditions known in the art. Standard suitable reductive aminations that can be used involve in situ reduction of the imine intermediate formed from the condensation of X and XIII. The reductive amination reaction can be conducted with a suitable hydride reagent such as sodium triacetoxyborohydride (STAB) or sodium cyanoborohydride in a suitable organic solvent(s) in the presence of a suitable acid at temperatures between 0 and 80° C. Suitable organic solvents include protic (e.g., MeOH) and aprotic solvents (e.g. THF) and suitable acids include protic (e.g., HOAc)

and Lewis acids (e.g., ZnCl$_2$, Ti(OiPr)$_4$). In the case where intermediates of formula X are unprotected (i.e., Q=H), the reductive amination products of formula XII are compounds of formula I. Reductive amination intermediate products of formula XII in which Q is a protecting group can be converted to compounds of formula I using methods known in the art (e.g., when Q=tosyl using aqueous NaOH in a suitable organic solvent with heating).

An alternative method of synthesizing compounds of formula I is depicted in Scheme 3.

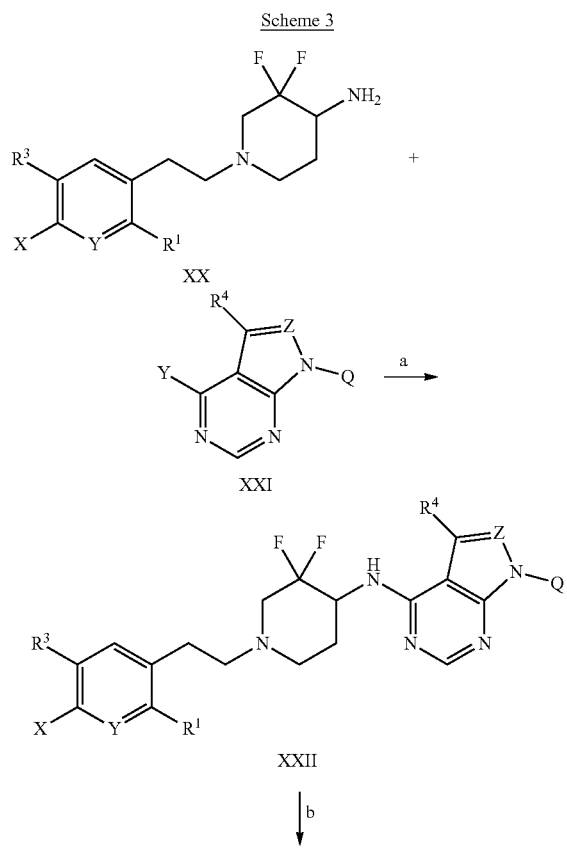

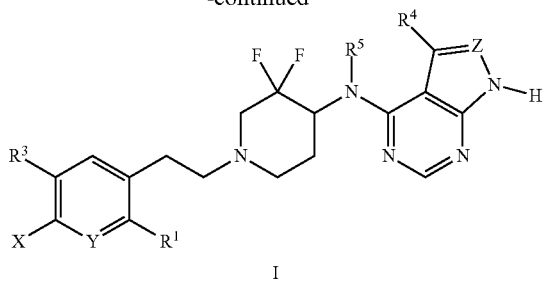

Y = Cl, Br
Q = H or protecting group e.g. THP, Ts
a. base or Buchwald reaction mediated amine coupling reaction conditions b. conditions suitable for removal of Q protecting group (e.g., HCl solution for Q = tetrahydropyranyl, or aq. NaOH solution/heat for Q = tosyl)

In a first step, intermediate 4-aminopiperidines of formula XX can be coupled with intermediates of formula XXI under suitable conditions to give compounds of formula XXII. In some cases, suitable conditions include conditions known for base nucleophilic aromatic substitution reaction on compounds of formula XXI wherein Y=Cl (e.g., using diisopropylethylamine in a protic or aprotic organic solvent such as n-BuOH, DMF, DMSO at elevated temperatures, e.g., 80-120° C.). In some cases, suitable conditions include known for Buchwald palladium catalyzed coupling reaction on compounds of formula XXI wherein Y=Cl or Br (see, e.g., Buchwald, S.; Muci, A. *Top. Curr. Chem.* 2002; 219, 133-209). Buchwald couplings can be conducted in suitable organic solvents (e.g., t-butanol, toluene, DMF, DMSO, CH$_3$CN) in the presence of a suitable palladium catalyst and phosphine ligand system (e.g., Brettphos/Brettphos precatalyst, BINAP/Pd$_2$(dba)$_3$) at elevated temperatures such as from 70° C. to 150° C. in the presence of a suitable base (e.g., Cs$_2$CO$_3$). Intermediates of formula XXII in which Q is a protecting group can be converted to compounds of formula I using methods known in the art (e.g., when Q=2-tetrahydropyranyl using aqueous HCl in a suitable organic solvent at ambient temperature, and when Q=tosyl using aqueous NaOH in a suitable organic solvent with heating).

Intermediates of general formula XI and aldehyde intermediates of general formula XIIIa can be synthesized according to Scheme 4 and/or using methods known in the art.

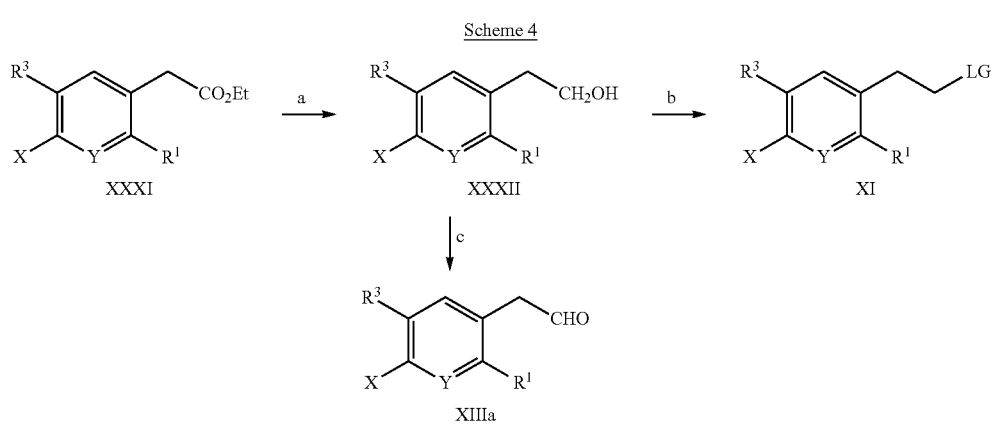

a. LiAlH$_4$, THF, 0° C. to room temperature b. Tf$_2$O, Et$_2$O, DIPEA 0° C. c. DMSO, oxalyl chloride, Et$_3$N, CH$_2$Cl$_2$ -70° C. to room temperature Starting ethyl arylacetates of formula XXXI can be purchased or synthesized using methods known in the art, e.g., by nucleophilic aromatic substitution reaction of diethyl malonate with suitable aryl fluorides followed by functional group conversions known in the art. Methods known in the art (e.g., using LiAlH$_4$ in THF) can be used to afford reduction of the ester group in compounds of formula XXXI to yield corresponding alchohols of formula XXXII. The alcohol group in compounds of general formula XXXII can be converted to a suitable leaving group (e.g., iodide or trifluoromethanesulfonate) using methods known in the art. For example treatment with triflic anhydride in ether solvent with N,N-diisopropylethyl amine at 0° C. can be used to prepare trifluoromethane sulfonates of formula XI (LG=OSO$_2$CF$_3$). Aldehydes of formula XIIIa can be prepared from alchohol intermediates of formula XXXII using oxidation methods well established in the art (e.g., via Swern oxidation, DMSO-oxalyl chloride).

Intermediates of general formula X can be synthesized according to Scheme 5 from known intermediates of formulas L and XXI according to methods known in the art.

Scheme 5

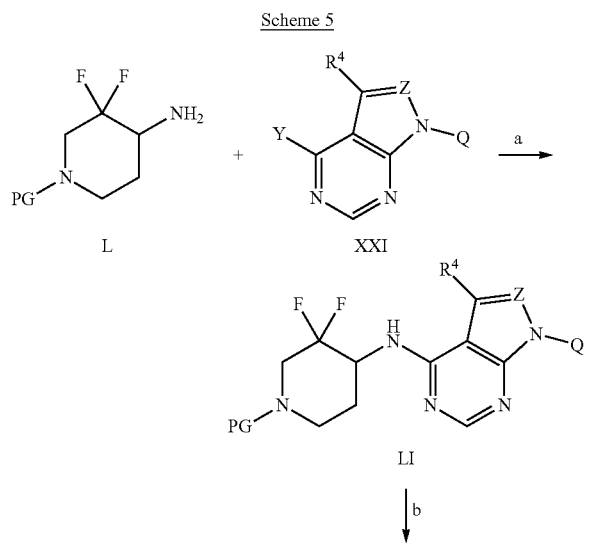

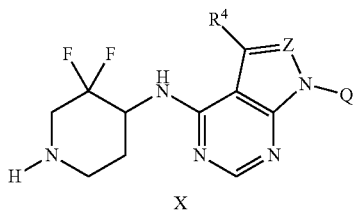

PG = protecting group e.g. Boc, Cbz
a. base or Buchwald reaction mediated amine coupling reaction conditions b. Cbz removal, e.g., by catalytic hydrogenation H$_2$/ Pd—C /EtOH or Boc removal, e.g., using HCl—MeOH In a first step, starting 4-amino-N-benzyloxycarbonyl or 4-amino-N-t-butyloxycarbonyl protected piperidines of formula L can be coupled with intermediates of formula XXI under suitable known conditions to give compounds of formula LI. In some cases, suitable conditions include conditions known for base nucleophilic aromatic substitution reaction on compounds of formula XXI wherein Y=Cl (e.g., using diisopropylethylamine in a protic or aprotic organic solvent such as n-BuOH, DMF, DMSO at elevated temperatures, e.g., 80-120° C.). In some cases, suitable conditions include known for Buchwald palladium catalyzed coupling reaction on compounds of formula XXI wherein Y=Cl or Br (Buchwald, S.; Muci, A. *Top. Curr. Chem.* 2002; 219, 133-209). Buchwald couplings can be conducted in suitable organic solvents (e.g., t-butanol, toluene, DMF, DMSO, CH$_3$CN) in the presence of a suitable palladium catalyst and phosphine ligand system (e.g., Brettphos/Brettphos precatalyst, BINAP/Pd$_2$(dba)$_3$) at elevated temperatures such as from 70° C. to 150° C. in the presence of a suitable base (e.g., Cs$_2$CO$_3$). In final step, the Cbz or Boc protecting groups of the coupling products of formula LI can be removed under standard conditions well known in the art (e.g., catalytic hydrogenation for Cbz, HCl-MeOH for Boc) to give intermediates of general formula X.

Scheme 6

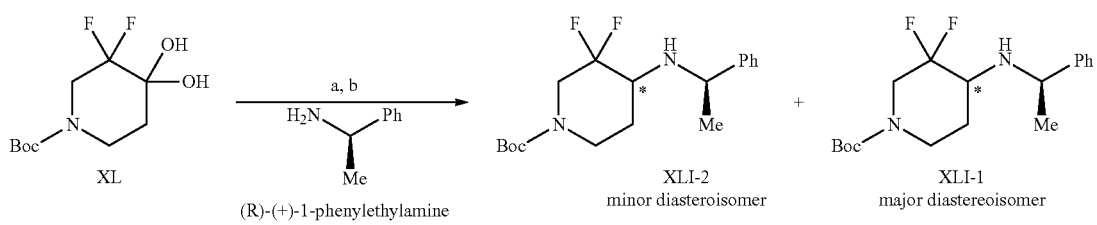

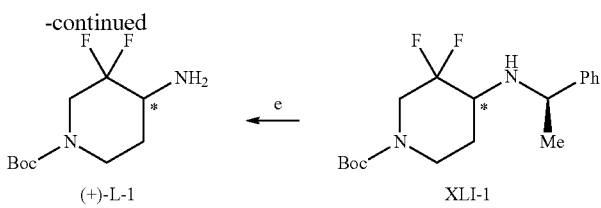

a. toluene, reflux b. NaBH(OAc)₃, dichloroethane, rt c. p-TsOH, EtOH, tosylate salt formation
d. tosylate salt formation in EtOH, salt recrystallization from acetone-ethanol e. free base formation from pure salt diastereomer, Pd/C, H₂, MeOH Racemic 4-amino-N-t-butyloxycarbonyl protected piperidine of formula L can be prepared as previously described (Baumann, K. et. al. U.S. Patent Appl. Publ. No. 2011/0201605). Herein is described the enantioselective synthesis of the tert-butyl 4-amino-3,3-difluoropiperidine-1-carboxylate enantiomers (+)-L-1 (as depicted in Scheme 6) and (−)-L-1. In a first step, enantiomerically pure (either (R)-(+) or (S)-(−)) 1-phenylethylamine is condensed with tert-butyl 3,3-difluoro-4,4-dihydroxypiperidine-1-carboxylate, XL (synthesis of XL: Madaiah M. et. Al. *Tetrahedron Lett.* 2013, 54, 1424-27). After solvent removal and exchange with dichloroethane the resulting imine is subsequently reduced with excess sodium acetoxyborohydride under heating from 40° C. to 60° C. A mixture of diastereomers is obtained in which the major diastereomer is formed in several fold excess relative to the minor diastereomer (by ¹H-NMR analysis). As depicted in Scheme 6, using (R)-1-phenylethylamine, the major form (R*) is denoted as formula XLI-1 and the minor form (S*) as XLI-2. The mixture can be separated by formation of the tosylate salt followed by crystallization from acetone-ethanol to give a single diastereomer (e.g., XLI-1 as depicted in Scheme 6, denoted R* throughout) of high diastereomeric purity. Catalytic hydrogenation of the free base of pure diastereomer then allows isolation of the high purity enantiomers L-1 (as depicted in Scheme 6, denoted R* throughout) and L-2 (denoted S* throughout, prepared by analogous methods using (S)-1-phenylethylamine in place of (R)-1-phenylethylamine).

Intermediates of general formula XXI wherein $R^4$ is $C_1$-$C_3$ alkyl or cyclopropyl can be synthesized according to Scheme 7 and/or using methods known in the art.

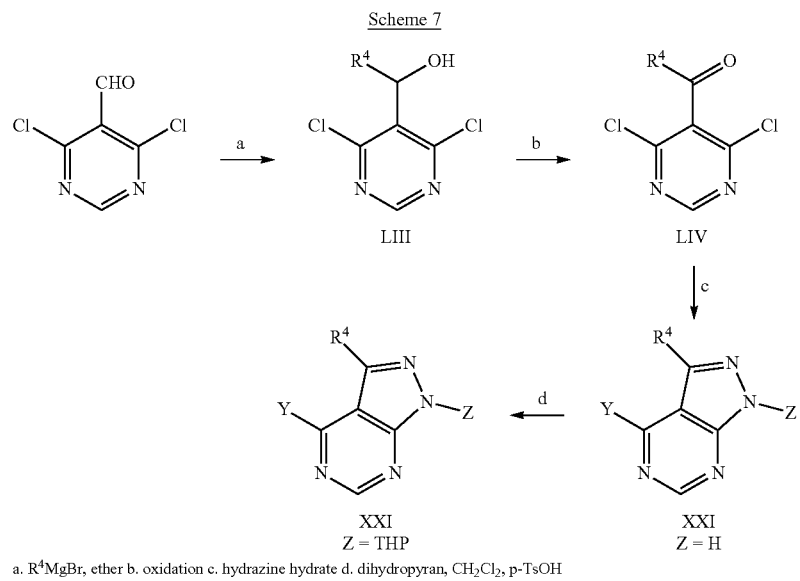

a. R⁴MgBr, ether b. oxidation c. hydrazine hydrate d. dihydropyran, CH₂Cl₂, p-TsOH In a first step, 4,6-dichloropyrimidine-5-carboxaldehyde is reacted with a Grignard reagent, e.g., $R^4$MgBr, as would be derived from the corresponding bromide $R^4$Br using conditions known in the art, to give alcohols of general formula LIII. Oxidation of intermediates of formula LIII under conditions known in the art for preparing ketones from benzylic secondary alcohols, e.g., using Dess Martin reagent, MnO₂ or CrO₃, gives intermediates of formula LIV. Treatment of intermediates of formula LIV with hydrazine gives compounds of general formula XXI wherein $R^4$ is $C_1$-$C_3$ alkyl or cyclopropyl and Z is hydrogen. The latter can be treated with dihydropyran in an aprotic organic solvent (e.g., CH₂Cl₂) with an acid catalyst (e.g., p-toluenesulfonic acid) to give compounds of general formula XXI wherein $R^4$ is $C_1$-$C_3$ alkyl or cyclopropyl and Z is a tetrahydropyranyl protecting group.

EXAMPLES

Example 1. Chemical Entities

As depicted in the Examples below, in certain exemplary embodiments, chemical entities are prepared according to the following procedures. It will be appreciated that, although the general methods depict the synthesis of certain chemical entities of the present invention, the following methods, and other methods known to persons skilled in the art, can be applied to all chemical entities and subclasses and species of each of these chemical entities, as described herein.

Temperatures are given in degrees centigrade. If not mentioned otherwise, all evaporations are performed under reduced pressure, preferably between 15 mm Hg and 100 mm Hg. The structures of intermediates and final products are confirmed by standard analytical methods, for example, mass spectrometry and NMR spectroscopy.

Enantiomeric purity determinations by chiral HPLC were performed using Diacel ChiralPAK® AD—H HPLC columns (4.6×150 mm, 5 µm).

ABBREVIATIONS

AcOH acetic acid
aq aqueous
Bn benzyl
Boc t-butoxycarbonyl
Cbz benzyloxycarbonyl
DAST diethylaminosulfur trifluoride
DCM dichloromethane
DCE 1,2-dichloroethane
DIBAL diisobutylaluminum hydride
DIPEA N,N-diisopropylethylamine
DMF N,N-dimethylformamide
DMSO dimethyl sulfoxide
Et ethyl
Et$_2$O diethyl ether ("ether")
EtOAc ethyl acetate
EtOH ethanol
eq equivalents
h hours
HPLC high performance liquid chromatography
LC liquid chromatography
LHDMS lithium hexamethyldisilazide
Me methyl
min minutes
MS mass spectrometry
MS (ESI) mass spectrometry electrospray ionization
NMP N-methyl-2-pyrrolidone
NMR nuclear magnetic resonance
rt room temperature
Tf triflate
Tf$_2$O triflic anhydride
TFAA trifluoroacetic anhydride
THF tetrahydrofuran
THP tetrahyropyranyl
TLC thin layer chromatography
TMSCI trimethylsilyl chloride
Ts p-toluenesulfonyl
TsCl p-toluenesulfonyl chloride Example 1.A.
4-chloro-1H-pyrazolo[3,4-d]pyrimidine

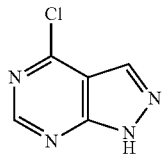

To a suspension of allopurinol (2.0 g, 15 mmol) in toluene (20 mL) was added POCl$_3$ (7 mL, 74 mmol) and DIPEA (6 mL, 32 mmol). The mixture was heated to 85° C. with stirring for 2 hrs. The mixture was allowed to cool, concentrated to half of the volume and poured into 2M K$_2$HPO$_4$ (200 mL). The mixture was stirred overnight at room temperature and filtered. The filter mass was washed with EtOAc, and the filtrate was extracted with EtOAc. The combined organic phases were washed with brine, dried over Na$_2$SO$_4$ and concentrated to afford the title compound as pale orange powder (1.6 g, 70%). MS (ESI) calcd for C$_5$H$_3$ClN$_4$: 154.0; found: 155 [M+H]. $^1$H NMR (400 MHz, d6-DMSO) δ 14.47 (brs, 1H), 8.82 (s, 1H), 8.43 (s, 1H).

Example 1.B. 4-chloro-1-(tetrahydro-2H-pyran-2-yl)-1H-pyrazolo[3,4-d]pyrimidine

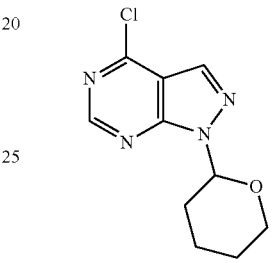

To a solution of 4-chloro-1H-pyrazolo[3,4-d]pyrimidine (35 g, 226 mmol) in THF (1 L) was added dihydropyran (31 mL, 340 mmol) and p-TsOH.H$_2$O (4.3 g, 22.6 mmol). The solution was heated to reflux. After stirring for 1 h, another batch of dihydropyran (16 mL, 175 mmol) was added. After stirred for additional 1 h, the solution was concentrated and purified by column chromatography over silica gel (DCM/EtOAc: 2%~10%) to afford the title compound as a white powder (50 g, 90%). MS (ESI) calcd for C$_{10}$H$_{11}$ClN$_4$O: 238; found: 239 [M+H]. $^1$H NMR (400 MHz, CDCl$_3$) δ 8.80 (s, 1H), 8.20 (s, 1H), 6.11-5.99 (m, 1H), 4.16-4.05 (m, 1H), 3.85-3.74 (m, 1H), 2.69-2.57 (m, 1H), 2.24-2.11 (m, 1H), 2.05-1.94 (m, 1H), 1.87-1.71 (m, 2H), 1.71-1.59 (m, 1H).

Example 1.C. 4-chloro-1-tosyl-1H-pyrazolo[3,4-d]pyrimidine

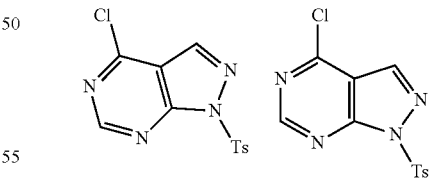

To a stirred solution of 4-chloro-1H-pyrazolo[3,4-d]pyrimidine (155 mg, 1 mmol) in dry THF (5 mL) was added NaH (60% dispersion in mineral oil, 80 mg, 2 mmol) at 0° C. under nitrogen atmosphere. After stirring for 5 min at low temperature, TsCl (250 mg, 1.3 mmol) was added. The mixture was stirred for 15 min at room temperature, and the starting material was consumed. The reaction was quenched with ice water under ice water bath cooling, and then diluted with ethyl acetate. The organic phase was washed with brine, dried over Na$_2$SO$_4$ and concentrated under reduced pressure. The residue was purified by column chromatography over silica gel (DCM/hexane=2/1) to afford the title compound as a white powder (227 mg, 73%). MS (ESI) calcd for $C_{12}H_9ClN_4O_2S$: 308.0; found: 309.0 [M+H]. $^1$H NMR (400 MHz, CDCl$_3$) δ 8.98 (s, 1H), 8.30 (s, 1H), 8.09 (d, J=8.0 Hz, 2H), 7.34 (d, J=8.0 Hz, 2H), 2.41 (s, 3H).

Example 1.D. 4-chloro-1-tosyl-1H-pyrolo[3,4-d]pyrimidine

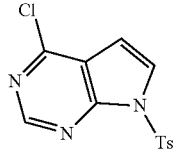 [SMILES: Cc1ccc(S(=O)(=O)n2ccc3c(Cl)ncnc32)cc1]

To a stirred solution of TsCl (1.35 g, 7.0 mmol) and 4-chloro-7H-pyrrolo[2,3-d]pyrimidine (1.0 g, 6.4 mmol) in acetone (10 mL) was added 2.0 M aqueous NaOH (8 mL, 16 mmol) at 0° C. The mixture was stirred at ambient temperature for 6 hours yielding a suspension. The solid product was collected by filtration and washed with acetone/water to afford the title compound as a white solid (0.9 g, 45%). MS (ESI) calcd for $C_{13}H_{10}ClN_3O_2S$: 307.0; found: 308.1 [M+H]. $^1$H NMR (400 MHz, CDCl$_3$) δ 8.77 (s, 1H), 8.09 (d, J=8.0 Hz, 2H), 7.78 (d, J=4.0 Hz, 1H), 7.33 (d, J=8.0 Hz, 2H), 6.71 (d, J=4.0 Hz, 1H), 2.41 (s, 3H).

Example 1.E. tert-butyl 3,3-difluoro-4,4-dihydroxypiperidine-1-carboxylate

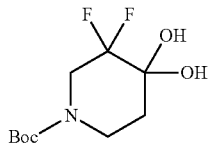 [SMILES: CC(C)(C)OC(=O)N1CCC(O)(O)C(F)(F)C1]

Step 1. ethyl 3-(((1H-benzo[d][1,2,3]triazol-1-yl)methyl)(benzyl)amino)propanoate

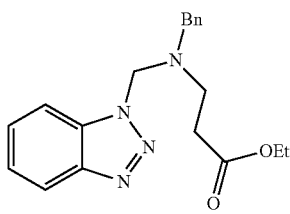 [SMILES: CCOC(=O)CCN(Cc1ccccc1)Cn1nnc2ccccc21]

To a solution of 1H-benzo[d][1,2,3]triazole (575 g, 4.82 mol) in MeOH (3.20 L) at 0° C. were added ethyl 3-(benzylamino)propanoate (1,000 g, 4.82 mol) and aqueous formaldehyde solution (37%, 470 mL, 5.79 mol). The reaction mixture was allowed to warm to room temperature and stirred overnight. The solvent was evaporated to give the title compound as a yellow oil (1678.0 g) which was used in the next step without further purification. MS (ESI) calcd for $C_{19}H_{22}N_4O_2$: 338.2; found: 339.2 [M+H]. $^1$H NMR (400 MHz, CDCl$_3$) δ 7.43-7.35 (m, 9H), 5.47 (s, 2H), 4.10 (q, J=7.2 Hz, 2H), 3.76 (s, 2H), 3.07 (t, J=6.8 Hz, 2H), 2.59 (t, J=6.8 Hz, 2H), 1.22 (t, J=7.2 Hz, 3H).

Step 2. ethyl 3-(benzyl(3-ethoxy-3-oxopropyl)amino)-2,2-difluoropropanoate

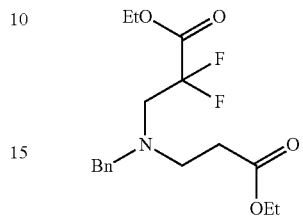

To a stirred suspension of activated zinc dust (618 g, 9.45 mol) in dry THF (9.0 L) under nitrogen was added trimethylsilyl chloride (539 g, 4.96 mol). After 30 min, ethyl 2-bromo-2,2-difluoroacetate (1055 g, 5.20 mol) was added slowly, maintaining the temperature below 30° C. A solution of ethyl 3-(((1H-benzo[d][1,2,3]triazol-1-yl)methyl)(benzyl)amino)-propanoate (1600 g, 4.78 mol) in dry THF (4.0 L) was added. The temperature of the exothermic reaction was maintained between 20 and 25° C. during the addition. The reaction mixture was stirred at room temperature overnight, poured over saturated aqueous sodium bicarbonate (1.0 L) and filtered through celite. The filtrate was extracted with EtOAc (3×3.0 L). The combined organic layers were washed with water (10.0 L), HCl (10 L, 0.5 M) and saturated aqueous sodium chloride solution (10.0 L) and dried over Na$_2$SO$_4$. The solvent was evaporated to give the title compound as a reddish liquid (1516 g) which was used in the next step without further purification. MS (ESI) calcd for $C_{17}H_{23}F_2NO_4$: 343.2; found: 344.1 [M+H]. $^1$H NMR (400 MHz, CDCl$_3$) δ 7.47-7.25 (s, 5H), 4.28 (q, J=7.2 Hz, 2H), 4.10 (q, J=7.2 Hz, 2H), 3.76 (s, 2H), 3.17 (t, J=13.2 Hz, 2H), 2.91 (t, J=7.6 Hz, 2H), 2.43 (t, J=7.6 Hz, 2H), 1.32 (t, J=7.2 Hz, 3H), 1.22 (t, J=7.2 Hz, 3H).

Step 3. ethyl 1-benzyl-5,5-difluoro-4-oxopiperidine-3-carboxylate

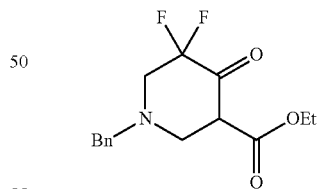

To a solution of ethyl 3-(benzyl(3-ethoxy-3-oxopropyl)amino)-2,2-difluoropropanoate (2.25 kg, 6.55 mol) in dry THF (11.5 L) at 0° C. was added lithium hexamethyldisilazide in THF (11.0 kg, 20%, 13.1 mol) dropwise, maintaining the temperature below 3° C. The reaction mixture was stirred for 3 hours. After completion of the reaction, the reaction mixture was extracted three times with saturated sodium chloride solution and the aqueous layer was back extracted once with EtOAc. The combined organic phases were dried over sodium sulfate and concentrated in vacuo to give the title compound as a reddish oil (2066 g). This crude product was used in the next step without further purification. MS (ESI) calcd for $C_{15}H_{17}F_2NO_3$: 297.1; found: 298.1 [M+H]. $^1$H NMR (400 MHz, CDCl$_3$) δ 7.32-7.28 (m, 5H), 4.06 (q, J=7.2 Hz, 2H), 3.76-3.72 (m, 1H), 3.65 (s, 2H), 3.30 (s, 2H), 2.82 (t, J=12.4 Hz, 2H), 1.17 (t, J=7.2 Hz, 2H).

Step 4. 1-benzyl-3,3-difluoropiperidine-4,4-diol

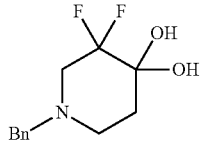

A solution of ethyl 1-benzyl-5,5-difluoro-4-oxopiperidine-3-carboxylate (4.9 kg, 16.5 mol) in HCl (17.0 L, 3N) was heated to reflux for 14 hours. Saturated aqueous sodium bicarbonate was added slowly to adjust the pH to 8 and the precipitated product was isolated by filtration. The filter cake was washed with water and dried to give the title compound as a white solid (2.7 Kg, 70% overall yield over 4 steps). $^1$H NMR (400 MHz, d6-DMSO) δ 7.35-7.25 (m, 5H), 6.13 (s, 2H), 3.55 (s, 2H), 2.65-2.60 (m, 2H), 2.43 (brs, 2H), 1.71 (brs, 2H).

Step 5. tert-butyl 3,3-difluoro-4,4-dihydroxypiperidine-1-carboxylate

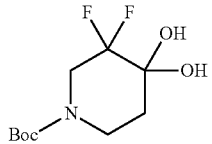

A suspension of 1-benzyl-3,3-difluoropiperidine-4,4-diol (6.3 g 26 mmol), di-tert-butyl dicarbonate (6.3 g, 29 mmol) and palladium on carbon (10%, 900 mg) in ethanol (100 mL) was hydrogenated at room temperature overnight. The mixture was filtered through celite and the filter pad was washed with MeOH. The combined filtrates were concentrated in vacuo to yield the title compound as a light yellow oil (6.7 g, 100%). MS (ESI) calcd for $C_{10}H_{17}F_2NO_4$: 253.1; found: 253.1 [M+H]. $^1$H NMR (400 MHz, CDCl$_3$) δ 3.72 (t, J=11.6 Hz, 2H), 3.56-3.46 (m, 2H), 1.83-1.77 (m, 2H), 1.46 (s, 9H).

Example 1.F. (±)-tert-butyl 4-amino-3,3-difluoropiperidine-1-carboxylate

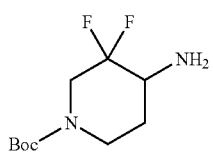 [SMILES: CC(C)(C)OC(=O)N1CCC(N)C(F)(F)C1]

Step 1. (±)-tert-butyl 4-(benzylamino)-3,3-difluoropiperidine-1-carboxylate

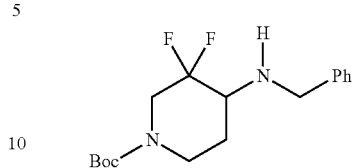

A mixture of tert-butyl 3,3-difluoro-4,4-dihydroxypiperidine-1-carboxylate (8.3 g, 33 mmol) and benzylamine (4.7 ml, 43 mmol) in dry toluene (150 ml) was heated to reflux over 24 hours with removal of condensed water via dean stark apparatus. The toluene solvent was distilled off, ethanol (55 mL) and NaBH$_4$ (4.2 g, 110 mmol) were added and the reaction mixture was stirred at 55° C. for 2 hours. Additional NaBH$_4$ (4.2 g, 110 mmol) was added and the mixture was stirred for another hour at 55° C. and a final portion of NaBH$_4$ (4.2 g, 110 mmol) was added. After 2 hours the reaction mixture was concentrated, 2N Na$_2$CO$_3$ solution was added and the aqueous phase was extracted with ethyl acetate. The combined organic phases were dried and concentrated. The residue was purified by flash chromatography ((hexane/EtOAc=4/1) to give the title compound as a colorless oil (7.5 g, 70%) which was used directly without further purification.

Step 2. (±)-tert-butyl 4-amino-3,3-difluoropiperidine-1-carboxylate

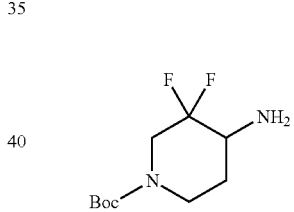

A suspension of tert-butyl 4-(benzylamino)-3,3-difluoropiperidine-1-carboxylate (7.5 g, 23 mmol) and palladium on carbon (10%, 750 mg) in MeOH (80 mL) was hydrogenated at room temperature for 36 hours. The mixture was filtered through celite and the filter pad was washed with MeOH. The combined filtrates were evaporated to yield the title compound as a light yellow oil (4.52 g, 83%). $^1$H NMR (400 MHz, CDCl$_3$) δ 4.38-3.86 (m, 2H), 3.18-2.86 (m, 3H), 1.95-1.85 (m, 1H), 1.55-1.49 (m, 1H), 1.46 (s, 9H).

Example 1.G. (+)-(R*)-tert-butyl 4-amino-3,3-difluoropiperidine-1-carboxylate

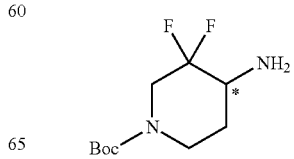

Step 1. (R*)-tert-butyl 3,3-difluoro-4-((R)-1-phenyl-ethylamino)piperidine-1-carboxylate

A mixture of tert-butyl 3,3-difluoro-4,4-dihydroxypiperidine-1-carboxylate (5.89 g, 23.0 mmol) and (R)-(+)-1-phenylethylamine (3.66 g, 30.3 mmol) in dry toluene (80 mL) was heated to reflux with dean stark apparatus mediated removal of condensation water. After stirring at reflux for 24 hours, the reaction mixture was concentrated and the concentrate was taken up in dichloroethane (100 mL) and methanol (10 mL). NaBH(OAc)$_3$ (15.0 g, 70.7 mmol) was added and the reaction mixture was stirred at 50° C. for 12 hours. An additional portion of NaBH(OAc)$_3$ (7.5 g, 35.0 mmol) was then added, and the reaction mixture was stirred for another 8 hours at 50° C. The mixture was concentrated, and 2N aqueous Na$_2$CO$_3$ solution was added. The aqueous phase was extracted with ethyl acetate. The combined organic phases were dried over sodium sulfate and concentrated under reduced pressure. The concentrate was purified by flash chromatography (hexane/EtOA c=5/1) to yield the title compound as a colorless oil (3.1 g, 47%). The oil was comprised of a ca. 7/1 mixture of the major to minor diastereoisomers by $^1$H-NMR analysis. To form the tosylate salt, a portion of the diastereomeric mixture (413 mg, 1.21 mmol) was dissolved in an ethanol (6 mL) and p-TsOH.H$_2$O (232 mg, 1.21 mmol) was added. The mixture was stirred at 60° C. for 1 hour and concentrated to give the crude tosylate salt. The salt was recrystallized twice from acetone-ethanol to give a white solid product comprising a ca. 19:1 mixture of major:minor tosylate salt diastereoisomers. To liberate the free base the solid was treated with sat. NaHCO$_3$ solution and the mixture was extracted with ethyl acetate. The combined organic extracts were dried over sodium sulfate, and concentrated to give the title compound free base as a colorless oil (203 mg, 47%). $^1$H NMR (400 MHz, CDCl$_3$) δ 7.38-7.32 (m, 4H), 7.30-7.24 (m, 1H), 4.18-4.04 (m, 1H), 3.96-3.70 (m, 1H), 3.17-2.96 (m, 1H), 2.90-2.62 (m, 2H), 1.81-1.64 (m, 1H), 1.65-1.57 (m, 2H), 1.35 (d, J=6.4 Hz, 3H).

Step 2. (+)-(R*)-tert-butyl 4-amino-3,3-difluoropiperidine-1-carboxylate

A stirred suspension of the above major diastereomer, (R*)-tert-butyl 3,3-difluoro-4-((R)-1-phenylethylamino)piperidine-1-carboxylate (126 mg, 0.37 mmol), and palladium on carbon (10%, 30 mg) in MeOH (8 mL) was hydrogenated at room temperature for 13 hours. The mixture was filtered through celite and the filter pad was extracted with MeOH. The solvent from the combined filtrates was evaporated to yield the title compound as a light yellow oil (85 mg, 100%). MS (ESI) calcd for C$_{10}$H$_{18}$F$_2$N$_2$O$_2$: 236.1; found: 181.2 [M+H]. $^1$H NMR (400 MHz, CDCl$_3$) δ 4.36-3.88 (m, 2H), 3.20-2.90 (m, 3H), 1.96-1.87 (m, 1H), 1.58-1.49 (m, 1H), 1.46 (s, 9H). [α]$_D^{20}$=+18.0° (c=10 mg/mL, ethanol).

Example 1.H. (−)-(S*)-tert-butyl 4-amino-3,3-difluoropiperidine-1-carboxylate

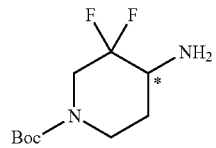

Step 1. (S*)-tert-butyl 3,3-difluoro-4-((S)-1-phenyl-ethylamino)piperidine-1-carboxylate

A mixture of tert-butyl 3,3-difluoro-4,4-dihydroxypiperidine-1-carboxylate (52.0 g, 0.21 mol) and (S)-(−)-1-phenylethanamine (29.9 g, 0.25 mol) in toluene (500 mL) was heated to reflux with dean stark apparatus mediated removal of condensation water. After heating at reflux for 24 hr, the reaction mixture was concentrated and the concentrate was redissolved in dichloroethane (500 mL). NaBH(OAc)$_3$ (100 g) was added in portions and the mixture was stirred for 12 hr at 50° C. Another batch of NaBH(OAc)$_3$ (100 g) was added and the mixture thus obtained was stirred for an additional 8 hr. The mixture was concentrated and the concentrate was partitioned between 2.0 M aqueous Na$_2$CO$_3$ and EtOAc. The aqueous phase was extracted with EtOAc and the combined organic phases were washed with brine, dried over Na$_2$SO$_4$ and concentrated. The residue was purified by column chromatography over silica gel ((hexane/EtOAc=5/1) to afford a ca. 7/1 mixture of product diastereomers by $^1$H-NMR analysis as a colorless oil (22.0 g, 31%). A mixture of this product oil (22.0 g, 65 mmol) and TsOH.H$_2$O (12.4 g, 65 mmol) in ethanol (250 mL) was stirred for 1 h at 60° C. and concentrated to give the crude tosylate salt as a white solid. The crude tosylate salt was recrystallized twice from acetone-ethanol (150 mL/15 mL) to afford a white solid (11.2 g) that was found to comprise an enriched ca. 19:1 mixture of major:minor tosylate salt diastereoisomers by $^1$H-NMR analysis. This salt was then treated with 1 M aqueous NaOH, and extracted with DCM. The combined organic phases were washed with brine, dried over Na$_2$SO$_4$ and concentrated to afford the title compound free base as a colorless oil (7.9 g, 36%) $^1$H NMR (400 MHz, CDCl$_3$) δ 7.35-7.30 (m, 4H), 7.28-7.23 (m, 1H), 4.16 (q, J=6.4 Hz, 1H), 3.88-3.78 (m, 1H), 3.08-2.98 (m, 1H), 2.81-2.65 (m, 2H), 1.72-1.69 (m, 1H), 1.60-1.58 (m, 2H), 1.44 (s, 9H), 1.32 (d, J=6.4 Hz, 3H).

Step 2. (−)-(S*)-tert-butyl 4-amino-3,3-difluoropiperidine-1-carboxylate

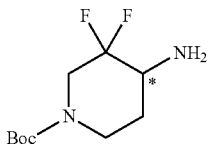 [SMILES: CC(C)(C)OC(=O)N1CCC(N)C(F)(F)C1]

A suspension of (S*)-tert-butyl 3,3-difluoro-4-((S)-1-phenylethylamino)piperidine-1-carboxylate (7.9 g, 23.5 mmol) and palladium on carbon (10%) (800 mg) in MeOH (100 mL) was hydrogenated at room temperature for 13 hr. The mixture was filtered through celite and the filter pad was washed with MeOH. The solvent was evaporated to yield the title compound as a light yellow oil (5.1 g, 100%). MS (ESI) calcd for $C_{10}H_{18}F_2N_2O_2$: 236.1; found: 237.1 [M+H]. NMR (400 MHz, CDCl$_3$) δ 4.38-3.88 (m, 2H), 3.18-2.88 (m, 3H), 1.96-1.88 (m, 1H), 1.58-1.49 (m, 1H), 1.46 (s, 1H), 1.38 (brs, 2H). $[\alpha]_D^{20}$=−19.5 (c=10 mg/mL, ethanol).

Example 1.1a. (±)-N-(3,3-difluoropiperidin-4-yl)-1H-pyrazolo[3,4-d]pyrimidin-4-amine dihydrochloride

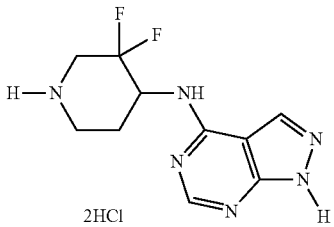 [SMILES: FC1(F)CNCCC1Nc1ncnc2[nH]ncc12]

Step 1. (±)-tert-butyl 3,3-difluoro-4-(1-(tetrahydro-2H-pyran-2-yl)-1H-pyrazolo[3,4-d]pyrimidin-4-ylamino)piperidine-1-carboxylate

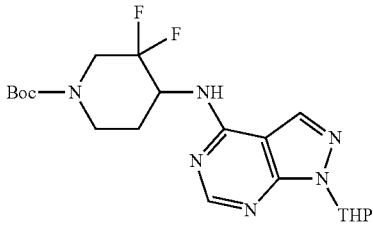

To a stirred suspension of (±)-tert-butyl 4-amino-3,3-difluoropiperidine-1-carboxylate (552 mg, 2.34 mmol) in isopropanol (10 mL) was added 4-chloro-1-(tetrahydro-2H-pyran-2-yl)-1H-pyrazolo[3,4-d]pyrimidine (584 mg, 2.46 mmol). The mixture was heated to 90° C. under nitrogen with stirring overnight. The resulting reaction mixture was allowed to cool to room temperature and concentrated in vacuo. The residue was purified by column chromatography over silica gel (ethyl acetate/hexane=1/1) to afford the title compound as a white powder (210 mg, 62%). NMR (400 MHz, CDCl$_3$) δ 8.44 (s, 1H), 8.00 (s, 1H), 5.98-5.95 (m, 1H), 5.54-5.48 (m, 1H), 5.03-4.88 (m, 1H), 4.66-4.20 (m, 2H), 4.15-4.10 (m, 1H), 3.82-3.76 (m, 1H), 3.22-2.88 (m, 2H), 2.64-2.52 (m, 1H), 2.18-2.08 (m, 2H), 1.96-1.92 (m, 1H), 1.81-1.72 (m, 3H), 1.64-1.58 (2H), 1.49 (s, 9H).

Step 2. (±)-N-(3,3-difluoropiperidin-4-yl)-1H-pyrazolo[3,4-d]pyrimidin-4-amine dihydrochloride

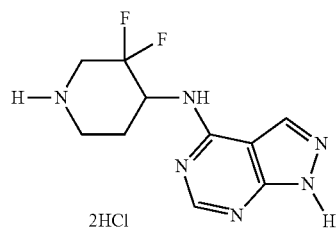 [SMILES: FC1(F)CNCCC1Nc1ncnc2[nH]ncc12]

To a stirred suspension of (±)-tert-butyl 3,3-difluoro-4-(1-(tetrahydro-2H-pyran-2-yl)-1H-pyrazolo[3,4-d]pyrimidin-4-ylamino)piperidine-1-carboxylate (890 mg, 2.03 mmol) in DCM (15 mL) was added 2.0M HCl in ether (15 mL). The solution was then stirred at ambient temperature for 12 hours. The resulting reaction mixture was concentrated under reduced pressure to afford the title compound as a white powder (600 mg, 91%). $^1$H NMR (400 MHz, DMSO-d$_6$) δ 8.27 (s, 1H), 8.18-8.17 (m, 1H), 8.10 (brs, 1H), 5.01-4.78 (m, 1H), 4.53-4.46 (m, 1H), 4.22-4.15 (m, 1H), 3.17-3.10 (m, 1H), 2.97-2.81 (m, 2H), 2.72-2.61 (m, 1H), 1.86-1.64 (m, 2H).

Example 1.1. (±)-N-(3,3-difluoropiperidin-4-yl)-1H-pyrazolo[3,4-d]pyrimidin-4-amine

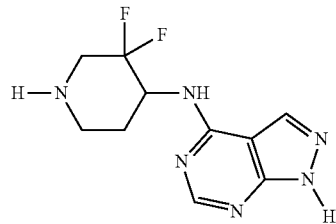 [SMILES: FC1(F)CNCCC1Nc1ncnc2[nH]ncc12]

To a stirred suspension of (±)-N-(3,3-difluoropiperidin-4-yl)-1H-pyrazolo[3,4-d]pyrimidin-4-amine dihydrochloride (600 mg) in methanol (10 mL) was added K$_2$CO$_3$ (2.0 g) at room temperature. After stirring for 30 min at room temperature, the supernatant was collected and concentrated under reduced pressure to afford the title compound free base as a pale brown solid (515 mg), which was directly used into the next step without further purification.

Example 1.Ja. (S*)-N-(3,3-difluoropiperidin-4-yl)-1H-pyrazolo[3,4-d]pyrimidin-4-amine dihydrochloride

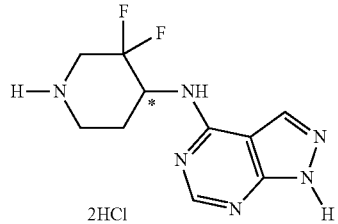 [SMILES: FC1(F)CNCCC1Nc1ncnc2[nH]ncc12]

Step 1. (S*)-tert-butyl 3,3-difluoro-4-(1-(tetrahydro-2H-pyran-2-yl)-1H-pyrazolo-[3,4-d]-pyrimidin-4-ylamino)piperidine-1-carboxylate

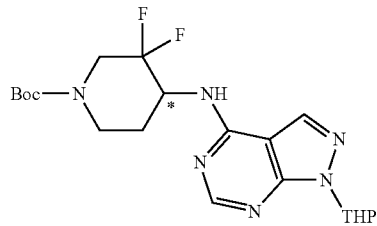

To a stirred suspension of (−)-(S*)-tert-butyl 4-amino-3,3-difluoropiperidine-1-carboxylate (5.10 g, 21.6 mmol) in n-BuOH (70 mL) was added 4-chloro-1-(tetrahydro-2H-pyran-2-yl)-1H-pyrazolo [3,4-d]pyrimidine (6.21 g, 25.9 mmol). The mixture was heated to 100° C. with stirring under nitrogen overnight. The reaction mixture was allowed to cool to room temperature and concentrated in vacuo. The residue was purified by column chromatography over silica gel (ethyl acetate/hexane=1/1) to afford the title compound as a white powder (7.50 g, 79%). $^1$H NMR (400 MHz, CDCl$_3$) δ 8.44 (s, 1H), 7.99 (s, 1H), 5.99-5.95 (m, 1H), 5.50-5.43 (m, 1H), 5.03-4.90 (m, 1H), 4.63-4.30 (m, 2H), 4.15-4.08 (m, 1H), 3.82-3.76 (m, 1H), 3.20-2.92 (m, 2H), 2.62-2.53 (m, 1H), 2.19-2.08 (m, 2H), 1.96-1.92 (m, 1H), 1.83-1.70 (m, 3H), 1.64-1.56 (m, 2H), 1.49 (s, 9H).

Step 2. (S*)-N-(3,3-difluoropiperidin-4-yl)-1H-pyrazolo[3,4-d]pyrimidin-4-amine dihydrochloride

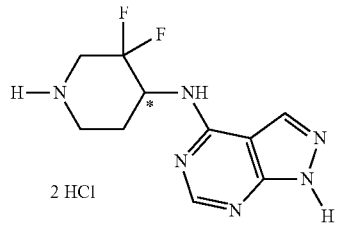 [SMILES: FC1(F)CNCCC1Nc1ncnc2[nH]ncc12]

To a stirred suspension of (S*)-tert-butyl 3,3-difluoro-4-(1-(tetrahydro-2H-pyran-2-yl)-1H-pyrazolo[3,4-d]pyrimidin-4-ylamino)piperidine-1-carboxylate (7.50 g, 17.1 mmol) in dichloromethane (30 mL) was added HCl in Et$_2$O (30 mL). The solution was then stirred at ambient temperature for 2 days. The resulting reaction mixture was concentrated under reduced pressure to afford the title compound as a white powder which was used without further purification (5.2 g, 93%).

Example 1.J. (S*)-N-(3,3-difluoropiperidin-4-yl)-1H-pyrazolo[3,4-d]pyrimidin-4-amine The title compound was made in an analogous manner to (±)-N-(3,3-difluoropiperidin-4-yl)-1H-pyrazolo[3,4-d]pyrimidin-4-amine as described in Example 1.1, except that (S*)-N-(3,3-difluoropiperidin-4-yl)-1H-pyrazolo[3,4-d]pyrimidin-4-amine dihydrochloride was used in place of (±)-N-(3,3-difluoropiperidin-4-yl)-1H-pyrazolo[3,4-d]pyrimidin-4-amine dihydrochloride.

Example 1.Ka. (R*)-N-(3,3-difluoropiperidin-4-yl)-1H-pyrazolo[3,4-d]pyrimidin-4-amine dihydrochloride The title compound was made in an analogous manner to (S*)-N-(3,3-difluoropiperidin-4-yl)-1H-pyrazolo[3,4-d]pyrimidin-4-amine dihydrochloride as described in Example 1.Ja, except that (+)-(R*)-tert-butyl 4-amino-3,3-difluoropiperidine-1-carboxylate was used in place of (−)-(S*)-tert-butyl 4-amino-3,3-difluoropiperidine-1-carboxylate.

Example 1.K. (R*)-N-(3,3-difluoropiperidin-4-yl)-1H-pyrazolo[3,4-d]pyrimidin-4-amine The title compound was made in an analogous manner to (±)-N-(3,3-difluoropiperidin-4-yl)-1H-pyrazolo[3,4-d]pyrimidin-4-amine as described in Example 1.1, except that (R*)-N-(3,3-difluoropiperidin-4-yl)-1H-pyrazolo[3,4-d]pyrimidin-4-amine dihydrochloride was used in place of (±)-N-(3,3-difluoropiperidin-4-yl)-1H-pyrazolo[3,4-d]pyrimidin-4-amine dihydrochloride.

Example 1.1. (+)-(R*)-N-(3,3-difluoro-1-(4-(trifluoromethyl)phenethyl)piperidin-4-yl)-1H-pyrazolo[3,4-d]pyrimidin-4-amine (E1-1.5)

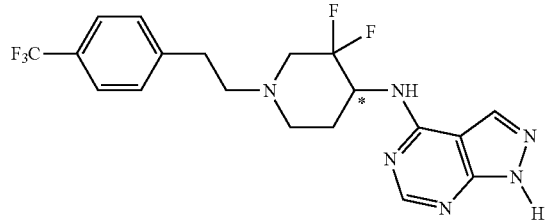 [SMILES: FC(F)(F)c1ccc(CCN2CCC(Nc3ncnc4[nH]ncc34)C(F)(F)C2)cc1]

Step 1. 2-(4-(trifluoromethyl)phenyl)ethanol

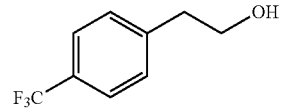

To a stirred mixture of LiAlH₄ (950 mg, 0.25 mmol) in dry ether (40 mL) was added dropwise methyl 2-(4-(trifluoromethyl)phenyl)acetate (5.40 g 0.25 mol) in dry ether (10 mL) under ice-water bath cooling. The reaction mixture was stirred at ambient temperature for 2 hours and cautiously quenched by slow addition of water under ice-water bath cooling. The mixture was diluted with ethyl acetate and filtered through a pad of celite. After the filter mass was rinsed with ethyl acetate for several times, the organic phases were combined, washed with brine, dried over Na₂SO₄ and concentrated. The residue was purified by column chromatography over silica gel (ethyl acetate/hexane=1/10) to afford the title compound as a colorless oil (4.50 g, 96%). ¹H NMR (400 MHz, CDCl₃) δ 7.57 (d, J=8.0 Hz, 2H), 7.35 (d, J=8.0 Hz, 2H), 3.90 (t, J=6.4 Hz, 2H), 2.93 (t, J=6.4 Hz, 2H).

Step 2. 4-(trifluoromethyl)phenethyl trifluoromethanesulfonate

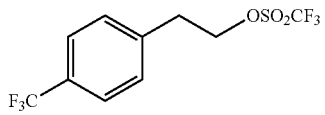

To a stirred solution of 2-(4-(trifluoromethyl)phenyl)ethanol (1.01 g, 5.26 mmol) and DIPEA (1.03 g, 7.89 mmol) in dry ether (10 mL) was added dropwise Tf₂O (1.07 mL, 6.31 mmol) at 0° C. After stirring at room temperature for 1 h, the white suspension was filtered through celite, and the filter mass was rinsed with ether. The combined filtrates were concentrated and purified by column chromatography over silica gel (100% hexane) to afford the title compound as a colorless oil (1.51 g, 88%). ¹H NMR (400 MHz, CDCl₃) δ 7.62 (d, J=8.0 Hz, 2H), 7.36 (d, J=8.0 Hz, 2H), 4.72 (t, J=6.4 Hz, 2H), 3.20 (t, J=6.4 Hz, 2H).

Step 3. (R*)-tert-butyl 3,3-difluoro-4-(1-tosyl-1H-pyrazolo[3,4-d]pyrimidin-4-ylamino)-piperidine-1-carboxylate

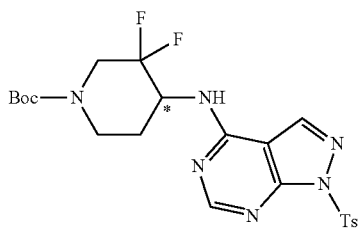 [SMILES: Cc1ccc(S(=O)(=O)n2ncc3c(NC4CCN(C(=O)OC(C)(C)C)CC4(F)F)ncnc32)cc1]

To a stirred suspension of (R*)-tert-butyl 4-amino-3,3-difluoropiperidine-1-carboxylate (500 mg, 2.12 mmol) in n-BuOH (5 mL) was added 4-chloro-1-tosyl-1H-pyrazolo-[3,4-d]-pyrimidine (685 mg, 2.22 mmol). The resulting mixture was heated to 100° C. under nitrogen. After stirred overnight, the resulting reaction mixture was cooled to room temperature and concentrated in vacuo. The residue was purified by column chromatography over silica gel (ethyl acetate/hexane=1/1) to afford the title compound as a white powder (900 mg, 83%). MS (ESI) calcd for C₂₂H₂₆F₂N₆O₄S: 508.2; found: 509.2 [M+H]. ¹H NMR (400 MHz, CDCl₃) δ 8.58 (s, 1H), 8.14 (s, 1H), 8.07 (d, J=8.0 Hz, 2H), 7.31 (d, J=8.0 Hz, 2H), 5.70-5.67 (m, 1H), 4.99-4.88 (m, 1H), 4.66-4.18 (m, 2H), 3.20-2.83 (m, 2H), 2.39 (s, 3H), 2.15-2.08 (m, 1H), 1.81-1.69 (m, 1H), 1.48 (s, 9H).

Step 4. (R*)-N-(3,3-difluoropiperidin-4-yl)-1-tosyl-1H-pyrazolo[3,4-d]pyrimidin-4-amine

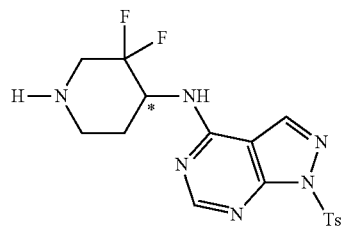 [SMILES: Cc1ccc(S(=O)(=O)n2ncc3c(NC4CCNCC4(F)F)ncnc32)cc1]

To a stirred suspension of (R*)-tert-butyl 3,3-difluoro-4-(1-tosyl-1H-pyrazolo-[3,4-d]pyrimidin-4-ylamino)piperidine-1-carboxylate (130 mg, 0.26 mmol) in dichloromethane (1 mL) was added TFA (0.2 mL). The solution was stirred at ambient temperature for 2 hours. The resulting reaction mixture was concentrated under reduced pressure, and then diluted with ethyl acetate. The mixture was washed with sat. NaHCO₃, water, brine, dried over Na₂SO₄ and concentrated under reduced pressure to afford the title compound as a white powder (90 mg, 91%) which was used in the next step without further purification. MS (ESI) calcd for C₁₇H₁₈F₂N₆O₂S: 408.1; found: 409.3 [M+H]. ¹H NMR (400 MHz, CD₃OD) δ 8.33 (s, 1H), 8.30 (s, 1H), 7.86 (s, J=8.0 Hz, 2H), 7.28 (d, J=8.0 Hz, 2H), 4.95-4.86 (m, 1H), 3.18-3.10 (m, 1H), 3.01-2.97 (m, 1H), 2.89-2.78 (m, 1H), 2.70-2.63 (m, 1H), 2.29 (s, 3H), 1.92-1.87 (m, 1H), 1.79-1.70 (m, 1H).

Step 5. (R*)-N-(3,3-difluoro-1-(4-(trifluoromethyl)phenethyl)piperidin-4-yl)-1-tosyl-1H-pyrazolo[3,4-d]pyrimidin-4-amine

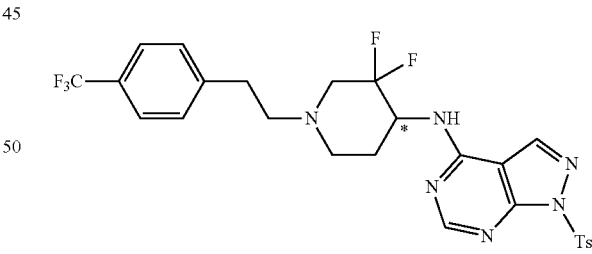

A mixture of 4-(trifluoromethyl)phenethyl trifluoromethanesulfonate (71 mg, 0.22 mmol), (R*)-N-(3,3-difluoropiperidin-4-yl)-1-tosyl-1H-pyrazolo[3,4-d]-pyrimidin-4-amine (75 mg, 0.18 mmol) and DIPEA (50 mg, 0.37 mmol) in dichloromethane (5 mL) was stirred at 40° C. for 24 hrs then concentrated to dryness. The residue was purified by column chromatography over silica gel (hexane/EtOAc=1/2) to afford the title compound as a white powder (91 mg, 84%). MS (ESI) calcd for C₂₆H₂₅F₅N₆O₂S: 580.2; found: 581.3 [M+H]. ¹H NMR (400 MHz, CDCl₃) δ 8.59 (s, 1H), 8.12 (s, 1H), 8.07 (d, J=8.0 Hz, 2H), 7.55 (d, J=8.0 Hz, 2H), 7.33-7.30 (m, 4H), 5.60-5.55 (m, 1H), 4.90-4.69 (m, 1H), 3.35-3.28 (m, 1H), 3.04-3.01 (m, 1H), 2.88 (t, J=7.6 Hz, 2H), 2.79-2.69 (m, 2H), 2.54-2.44 (m, 1H), 2.39 (s, 3H), 2.36-2.33 (m, 1H), 2.16-2.10 (m, 1H), 1.85-1.75 (m, 1H).

Step 6. (+)-(R*)-N-(3,3-difluoro-1-(4-(trifluoromethyl)phenethyl)piperidin-4-yl)-1H-pyrazolo[3,4-d]pyrimidin-4-amine

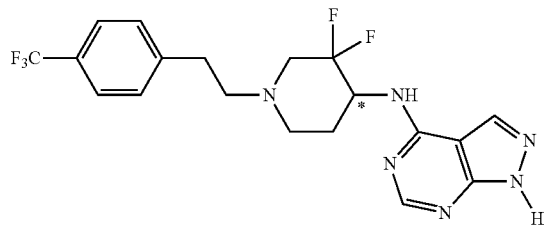

To a stirred solution of (R*)-N-(3,3-difluoro-1-(4-(trifluoromethyl)phenethyl)-piperidin-4-yl)-1-tosyl-1H-pyrazolo[3,4-d]pyrimidin-4-amine (67 mg, 0.115 mmol) in methanol (2 mL) was added 1N HCl in ether (2 mL, 2 mmol) at room temperature. After stirred overnight, the white suspension was concentrated to dryness. The residue was dissolved in water, and neutralized by addition of 1M aqueous NaOH. The aqueous phase was extracted with EtOAc. The combined organic phases were washed with brine, dried over $Na_2SO_4$ and concentrated. The residue was purified by column chromatography over silica gel (DCM/MeOH=30/1) to afford the title compound as a white powder (42 mg, 85%), >97% ee (Column: CHIRALPAKAD-H 4.6*150 mm, 5 um; Mobile Phase: A: Hexanes B: isopropyl Alcohol=70:30; t=7.535). $[\alpha]_D^{20}$=+37° (10 mg/mL, methanol) MS (ESI) calcd for $C_{19}H_{19}F_5N_6$: 426.2; found: 427.2 [M+H]. $^1$H NMR (400 MHz, $CD_3OD$) δ 8.28 (s, 1H), 8.26 (s, 1H), 7.59 (d, J=8.0 Hz, 2H), 7.47 (d, J=8.0 Hz, 2H), 4.99-4.83 (m, 1H), 3.41-3.35 (m, 1H), 3.13-3.08 (m, 1H), 2.98-2.89 (m, 2H), 2.84-2.73 (m, 2H), 2.62-2.52 (m, 1H), 2.46-2.39 (m, 1H), 2.07-1.92 (m, 2H).

Example 1.1a. (+)-(R*)-N-(3,3-difluoro-1-(4-(trifluoromethyl)phenethyl)piperidin-4-yl)-1H-pyrazolo[3,4-d]pyrimidin-4-amine hydrochloride (E1-1.5a)

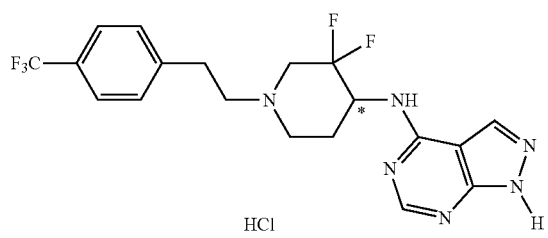 [SMILES: FC(F)(F)c1ccc(CCN2CCC(Nc3ncnc4[nH]ncc34)C(F)(F)C2)cc1 ; Cl]

To a stirred solution of (+)-(R*)-N-(3,3-difluoro-1-(4-(trifluoromethyl)phenethyl)-piperidin-4-yl)-1H-pyrazolo[3,4-d]pyrimidin-4-amine (3.51 g, 8.21 mmol) in MeOH (15 mL) was added HCl in methanol (2.0 M, 4.1 mL, 8.2 mmol). The reaction mixture was stirred at room temperature for 15 min. The solvent was evaporated to afford the title compound as a white powder (3.71 g, 98%). $[\alpha]_D^{20}$=+38° (10 mg/mL, methanol). MS (ESI) calcd for $C_{19}H_{19}F_5N_6$: 426.2; found: 427.4 [M+H]. $^1$H NMR (400 MHz, $CD_3OD$) δ 8.45 (brs, 2H), 7.67 (d, J=8.0 Hz, 2H), 7.54 (d, J=8.0 Hz, 2H), 5.33-5.25 (m, 1H), 3.97-3.93 (m, 1H), 3.64-3.61 (m, 1H), 3.51-3.36 (m, 1H), 3.32-3.23 (m, 2H), 3.21-3.08 (m, 3H), 2.35-2.18 (m, 2H).

Example 1.2. (−)-(S*)-N-(3,3-difluoro-1-(4-(trifluoromethyl)phenethyl)piperidin-4-yl)-1H-pyrazolo[3,4-d]pyrimidin-4-amine (E2-1.5)

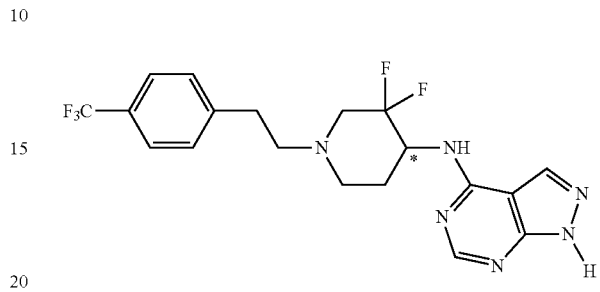

Step 1. (−)-(S*)-N-(3,3-difluoro-1-(4-(trifluoromethyl)phenethyl)piperidin-4-yl)-1H-pyrazolo[3,4-d]pyrimidin-4-amine

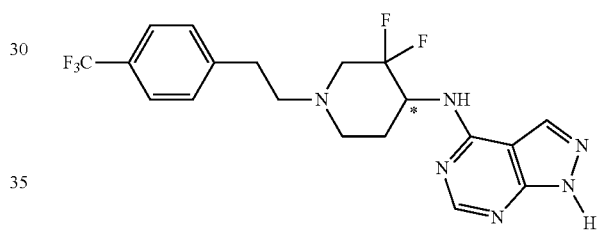

To a solution of 2-(4-(trifluoromethyl)phenyl)acetaldehyde (4.52 g, 23.9 mmol) and (S*)-N-(3,3-difluoropiperidin-4-yl)-1H-pyrazolo[3,4-d]pyrimidin-4-amine dihydrochloride (5.20 g, 15.9 mmol) in MeOH (100 mL) was added triethylamine (6.6 mL, 48 mmol) and a catalytic amount of AcOH. After stirring at room temperature for 30 min, $NaBH_3CN$ (2.0 g, 32 mmol) was added and the reaction mixture was stirred for an additional 15 min. The reaction mixture was concentrated, and taken up in EtOAc. The organic phase was washed with brine, dried over $Na_2SO_4$ and concentrated. The residue was purified by column chromatography over silica gel (DCM/MeOH=25/1) to afford the title compound as a white solid (4.38 g, 67%), 99.6% ee (Column: CHIRALPAKAD-H4.6*150 mm, 5 um; Mobile Phase: A: Hexanes B: Isopropyl Alcohol=70:30; t=9.935). $[\alpha]_D^{20}$=−43° (10 mg/mL, methanol) MS (ESI) calcd for $C_{19}H_{19}F_5N_6$:426.2; found: 427.1 [M+H]. $^1$H NMR (400 MHz, $CD_3OD$) δ 8.28 (s, 1H), 8.26 (s, 1H), 7.60 (d, J=8.0 Hz, 2H), 7.48 (d, J=8.0 Hz, 2H), 4.96-4.84 (m, 1H), 3.41-3.33 (m, 1H), 3.13-3.07 (m, 1H), 2.98-2.94 (m, 2H), 2.84-2.76 (m, 2H), 2.65-2.52 (m, 1H), 2.48-2.39 (m, 1H), 2.08-1.95 (m, 2H).

Example 1.2a. (−)-(S*)-N-(3,3-difluoro-1-(4-(trifluoromethyl)phenethyl)piperidin-4-yl)-1H-pyrazolo[3,4-d]pyrimidin-4-amine hydrochloride (E2-1.5a)

To a stirred solution of N-(3,3-difluoro-1-(4-(trifluoromethyl)phenethyl)piperidin-4-yl)-1H-pyrazolo[3,4-d]pyrimidin-4-amine (2.02 g, 4.74 mmol) in MeOH (30 mL) were added HCl solution in methanol (2.0 M, 2.37 mL, 4.74 mmol). The reaction solution was stirred at room temperature for 15 min. The solvent was evaporated to afford the title compound as a white powder (2.11 g, 98%). $[\alpha]_D^{20}=-44°$ (10 mg/mL, methanol). MS (ESI) calcd for $C_{19}H_{19}F_5N_6$: 426.2; found: 427.2 [M+H].

Example 1.3. (±)-N-(3,3-difluoro-1-phenethylpiperidin-4-yl)-1H-pyrazolo[3,4-d]pyrimidin-4-amine (C-1.1)

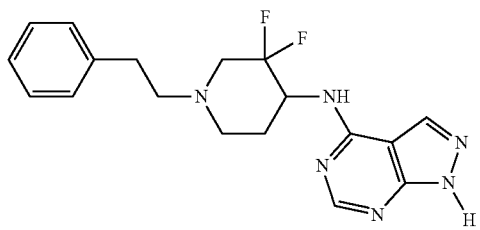 [SMILES: FC1(F)CN(CCc2ccccc2)CCC1Nc1ncnc2[nH]ncc12]

To a stirred solution of 2-phenylacetaldehyde (150 mg, 1.25 mmol) in MeOH (4 mL) was added (±)-N-(3,3-difluoropiperidin-4-yl)-1H-pyrazolo[3,4-d]pyrimidin-4-amine (330 mg, 1.30 mmol) and 2 drops of AcOH. The mixture was stirred for 15 min at rt. and then NaBH$_3$CN (160 mg, 2.5 mmol) was added. The resulting mixture was stirred for additional 15 min at r.t., then concentrated and extracted with EtOAc. The combined organic phases were washed with H$_2$O and brine, dried over anhydrous Na$_2$SO$_4$ and concentrated. The concentrate was purified by column chromatography over silica gel (DCM/MeOH=10/1) to afford the title compound as a white powder (276 mg, 62%). MS (ESI) calcd for $C_{18}H_{20}F_2N_6$: 358.2; found: 359.3 [M+H]. $^1$H NMR (400 MHz, CD$_3$OD) δ 8.28 (s, 1H), 8.26 (s, 1H), 7.33-7.24 (m, 4H), 7.23-7.17 (m, 1H), 3.43-3.34 (m, 1H), 3.13-3.10 (m, 1H), 2.89-2.71 (m, 4H), 2.62-2.52 (m, 1H), 2.46-2.40 (m, 1H), 2.05-1.95 (m, 2H).

Example 1.3a. (±)-N-(3,3-difluoro-1-phenethylpiperidin-4-yl)-1H-pyrazolo[3,4-d]pyrimidin-4-amine hydrochloride (C-1.1a)

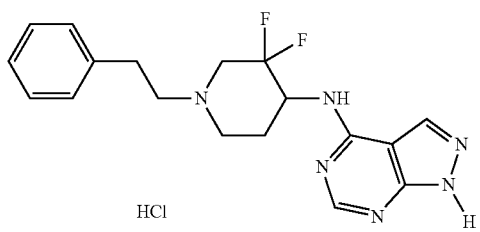 [SMILES: FC1(F)CN(CCc2ccccc2)CCC1Nc1ncnc2[nH]ncc12 ; Cl]

To a stirred solution of N-(3,3-difluoro-1-phenethylpiperidin-4-yl)-1H-pyrazolo-[3,4-d]pyrimidin-4-amine (272 mg, 0.76 mmol) in MeOH (6 mL) was added HCl/MeOH (0.4 mL, 2 N, 0.76 mmol) at r.t. After stirring for 10 min, the mixture was concentrated to afford the product as a white solid (261 mg, 96%). MS (ESI) calcd for $C_{18}H_{20}F_2N_6$: 358.2; found: 359.3 [M+H] $^1$H NMR (400 MHz, CD$_3$OD) δ 8.51 (brs, 2H), 7.41-7.33 (m, 4H), 7.33-7.28 (m, 1H), 5.42 (brs, 1H), 4.21-4.15 (m, 1H), 3.90-3.67 (m, 2H), 3.50-3.46 (m, 2H), 3.41-3.38 (m, 1H), 3.22-3.05 (m, 2H), 2.50-2.26 (m, 2H).

Example 1.4. (±)-N-(3,3-difluoro-1-(4-(trifluoromethyl)phenethyl)piperidin-4-yl)-7H-pyrrolo-[2,3-d]pyrimidin-4-amine (C-2.5)

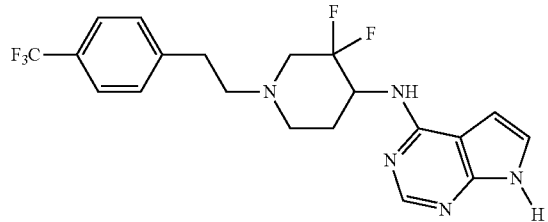

Step 1. (±)-N-(3,3-difluoro-1-(4-(trifluoromethyl)phenethyl)piperidin-4-yl)-7-tosyl-7H-pyrrolo[2,3-d]pyrimidin-4-amine

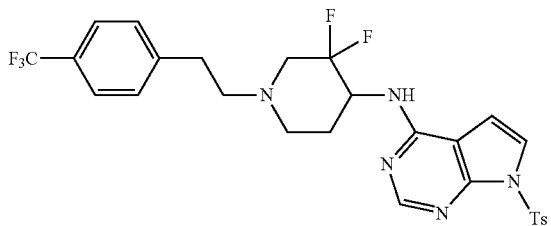 [SMILES: Cc1ccc(S(=O)(=O)n2ccc3c(NC4CCN(CCc5ccc(C(F)(F)F)cc5)CC4(F)F)ncnc32)cc1]

A mixture of 3,3-difluoro-1-(4-(trifluoromethyl)phenethyl)piperidin-4-amine (111 mg, 0.36 mmol), 4-chloro-7-tosyl-7H-pyrrolo[2,3-d]pyrimidine (111 mg, 0.36 mmol) and DIPEA (0.16 mL, 0.9 mmol) in NMP (1.4 mL) was heated to 120° C. under N$_2$. After stirring overnight at 120° C., the mixture was diluted with EtOAc, and washed with water. The organic phase was dried over Na$_2$SO$_4$, and concentrated. The residue was purified by column chromatography over silica gel (hexane/ethyl acetate=3/1) to afford the title compound as a pale yellow solid (150 mg, 72%).

Step 2. (±)-N-(3,3-difluoro-1-(4-(trifluoromethyl)phenethyl)piperidin-4-yl)-7H-pyrrolo-[2,3-d]pyrimidin-4-amine

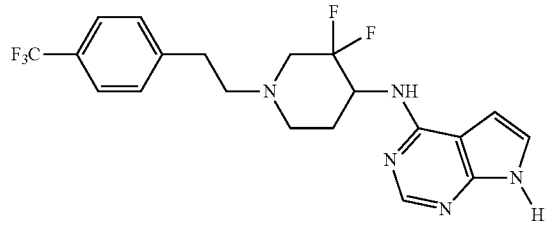 [SMILES: FC(F)(F)c1ccc(CCN2CCC(Nc3ncnc4[nH]ccc34)C(F)(F)C2)cc1]

To a stirred solution of N-(3,3-difluoro-1-(4-(trifluoromethyl)phenethyl)piperidin-4-yl)-7-tosyl-7H-pyrrolo[2,3-d]pyrimidin-4-amine (110 mg, 0.189 mmol) in MeOH (2.5 mL) was added the 50% aqueous NaOH (3 mL). The mixture thus obtained was stirred at 60° C. for 3 hours. The mixture was neutralized with 1 N HCl, and extracted with ethyl acetate. The organic phases were washed with water, brine, dried over Na$_2$SO$_4$ and concentrated. The residue was purified by silica gel column chromatography (DCM/MeOH=30/1) to afford the title compound as a yellow solid (65 mg, 80%). MS (ESI) calcd for C$_{20}$H$_{20}$F$_5$N$_5$: 425.2; found: 426.5 [M+H]. $^1$H NMR (400 MHz, CDCl$_3$) δ 10.27 (brs, 1H), 8.36 (s, 1H), 7.56 (d, J=8.0 Hz, 2H), 7.34 (d, J=8.0 Hz, 2H), 7.12 (d, J=3.6 Hz, 1H), 6.45 (d, J=3.6 Hz, 1H), 5.39-5.26 (m, 1H), 4.93-4.77 (m, 1H), 3.37-3.30 (m, 1H), 3.06-3.03 (m, 1H), 2.90-2.87 (m, 2H), 2.81-2.69 (m, 2H), 2.59-2.48 (m, 1H), 2.44-2.38 (m, 1H), 2.25-2.17 (m, 1H), 1.90-1.79 (m, 1H).

Example 1.4a. (±)-N-(3,3-difluoro-1-(4-(trifluoromethyl)phenethyl)piperidin-4-yl)-7H-pyrrolo[2,3-d]pyrimidin-4-amine hydrochloride (C-2.5a)

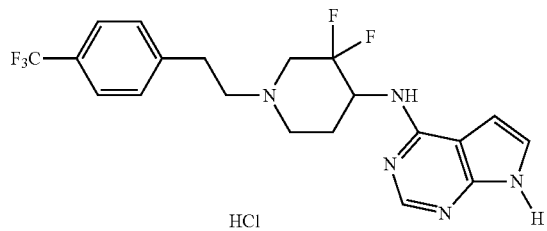 [SMILES: FC(F)(F)c1ccc(CCN2CCC(Nc3ncnc4[nH]ccc34)C(F)(F)C2)cc1 ; Cl]

To a stirred solution of N-(3,3-difluoro-1-(4-(trifluoromethyl)phenethyl)piperidin-4-yl)-7H-pyrrolo[2,3-d]pyrimidin-4-amine (45 mg, 0.11 mmol) in MeOH (1.5 mL) was added 2.0 M HCl/ether (50 µL, 0.11 mmol) at rt. After stirred for 10 min, the mixture was concentrated to afford the title compound as a white solid (47 mg, 98%). MS (ESI) calcd for C$_{20}$H$_{20}$F$_5$N$_5$: 425.2; found: 426.5 [M+H]. $^1$H NMR (400 MHz, CD$_3$OD) δ 8.51 (s, 1H), 7.71 (d, J=8.0 Hz, 2H), 7.58 (d, J=8.0 Hz, 2H), 7.43 (d, J=3.6 Hz, 1H), 7.07 (d, J=3.6 Hz, 1H), 5.47-5.30 (m, 1H), 4.34-4.27 (m, 1H), 3.96-3.85 (m, 2H), 3.67-3.49 (m, 3H), 3.29-3.22 (m, 2H), 2.55-2.46 (m, 2H).

Example 1.5. (±)-N-(3,3-difluoro-1-(4-(trifluoromethyl)phenethyl)piperidin-4-yl)-1H-pyrazolo[3,4-b]pyridin-4-amine (C-1.33)

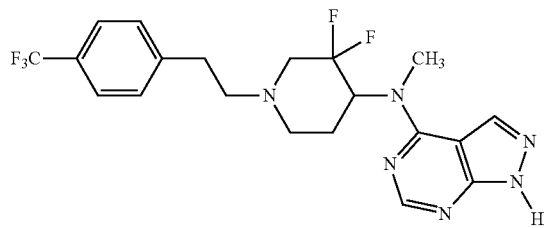 [SMILES: CN(c1ncnc2[nH]ncc12)C1CCN(CCc2ccc(C(F)(F)F)cc2)CC1(F)F]

Step 1. (±)-3,3-difluoro-1-(4-(trifluoromethyl)phenethyl)piperidine-4,4-diol

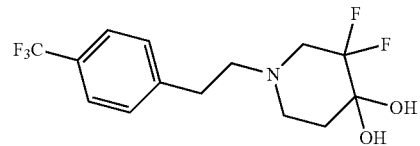 [SMILES: OC1(O)CCN(CCc2ccc(C(F)(F)F)cc2)CC1(F)F]

To a stirred mixture of 1-(2-bromoethyl)-4-(trifluoromethyl)benzene (1.0 g, 4.0 mmol) and 3,3-difluoropiperidine-4,4-diol (500 mg, 3.3 mmol) in n-BuOH was added DIPEA (1.3 mL, 7.9 mmol). The mixture was heated to 110° C. and stirred for 30 min. The mixture was concentrated under vacuum, and purified by column chromatography over silica gel (hexane/ethyl acetate=1/1) to afford the title product as a an oil (380 mg, 35%). $^1$H NMR (400 MHz, CDCl$_3$) δ 7.55 (t, J=8.4 Hz, 2H), 7.32 (t, J=8.4 Hz, 2H), 3.12-3.04 (m, 1H), 2.94-2.80 (m, 5H), 2.77-2.63 (m, 3H), 2.01-1.96 (m, 1H).

Step 2. (±)-N-benzyl-3,3-difluoro-1-(4-(trifluoromethyl)phenethyl)piperidin-4-amine

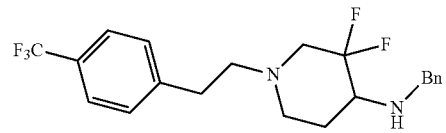 [SMILES: FC(F)(F)c1ccc(CCN2CCC(NCc3ccccc3)C(F)(F)C2)cc1]

To a stirred mixture of 3,3-difluoro-1-(4-(trifluoromethyl)phenethyl)piperidine-4,4-diol (450 mg, 1.9 mmol) in toluene (10 mL) was added benzylamine (0.27 mL, 2.48 mmol). The mixture was heated to 135° C. and the water was removed by Dean-Stark apparatus. After heating at reflux overnight, the mixture was concentrated in vacuo. The residue was taken up in ethanol (10 mL) and NaBH$_4$ (300 mg, 7.9 mmol) was added. The resulting mixture was stirred overnight at 50° C. The mixture was concentrated under vacuum, and 2N aqueous Na$_2$CO$_3$ was added. The aqueous phase was extracted with ethyl acetate. The combined organic phases were washed with brine, dried over Na$_2$SO$_4$ and concentrated in vacuo. The residue was purified by column chromatography over silica gel (hexane/ethyl acetate=1/1) to afford the title compound as an oil (410 mg, 53%).

Step 3. (±)-N-benzyl-3,3-difluoro-N-methyl-1-(4-(trifluoromethyl)phenethyl)piperidin-4-amine

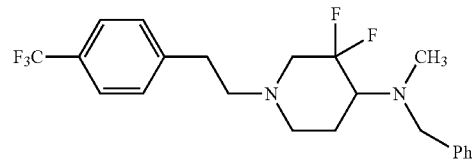 [SMILES: CN(Cc1ccccc1)C1CCN(CCc2ccc(C(F)(F)F)cc2)CC1(F)F]

A mixture of N-benzyl-3,3-difluoro-1-(4-(trifluoromethyl)phenethyl)piperidin-4-amine (100 mg, 0.25 mmol) and 37% aqueous formaldehyde (0.08 mL, 0.754 mmol) in 1,2-dichloroethane (3 mL) was stirred for 30 min at room temperature. Solid NaBH(AcO)₃ (213 mg, 1.0 mmol) was added and the resulting mixture was stirred for additional 12 hrs. The reaction mixture was concentrated, and the residue was partitioned into 2N aqueous Na₂CO₃ and EtOAc. The organic phase was washed with brine, dried over Na₂SO₄ and concentrated. The residue was purified by column chromatography over silica gel (hexane/EtOAc=3/1) to afford the title compound as a colorless oil (85 mg, 65%). ¹H NMR (400 MHz, CDCl₃) δ 7.57 (d, J=8.0 Hz, 2H), 7.36-7.24 (m, 7H), 3.93-3.84 (m, 2H), 3.23-3.16 (m, 1H), 3.09-3.07 (m, 1H), 2.87 (t, J=7.6 Hz, 2H), 2.83-2.78 (m, 1H), 2.74-2.62 (m, 2H), 2.48 (s, 3H), 2.32-2.25 (m, 1H), 2.22-2.16 (m, 1H), 2.14-2.03 (m, 1H), 1.87-1.84 (m, 1H).

Step 4. (±)-3,3-difluoro-N-methyl-1-(4-(trifluoromethyl)phenethyl)piperidin-4-amine

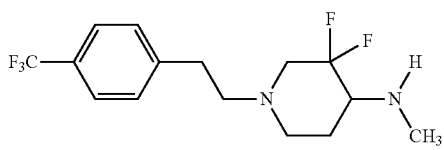

A suspension of (±)-N-benzyl-3,3-difluoro-N-methyl-1-(4-(trifluoromethyl)-phenethyl)-piperidin-4-amine (260 mg, 0.63 mmol) and palladium on carbon (10%, 30 mg) in MeOH (8 mL) was hydrogenated at room temperature for 13 hours. The mixture was filtered through celite, and the filter pad was extracted with MeOH. The combined filtrates were concentrated to yield the title compound as a light yellow oil (190 mg, 100%). ¹H NMR (400 MHz, CDCl₃) δ 7.54 (d, J=8.0 Hz, 2H), 7.31 (d, J=8.0 Hz, 2H), 3.15-3.07 (m, 1H), 2.87-2.83 (m, 3H), 2.78-2.71 (m, 1H), 2.69-2.63 (m, 2H) 2.54 (s, 3H), 2.49-2.37 (m, 1H), 2.29-2.24 (m, 1H), 2.02-1.95 (m, 1H), 1.66-1.59 (m, 1H).

Step 5. (±)-N-(3,3-difluoro-1-(4-(trifluoromethyl)phenethyl)piperidin-4-yl)-N-methyl-1-(tetrahydro-2H-pyran-2-yl)-1H-pyrazolo[3,4-d]pyrimidin-4-amine

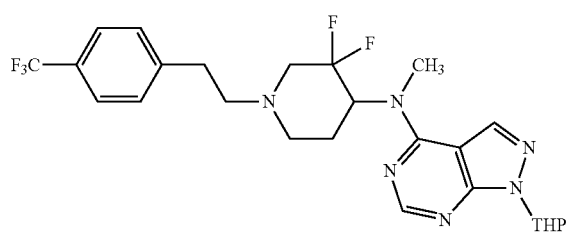

A mixture of (±)-3,3-difluoro-N-methyl-1-(4-(trifluoromethyl)phenethyl)piperidin-4-amine (190 mg, 0.59 mmol), 4-chloro-1-(tetrahydro-2H-pyran-2-yl)-1H-pyrazolo[3,4-d]pyrimidine (154 mg, 0.649 mmol) and DIPEA (0.2 mL, 1.2 mmol) in n-BuOH (3 mL) was heated to 120° C. After stirring overnight at 120° C., the orange solution was concentrated. The concentrate was purified by column chromatography over silica gel (hexane/ethyl acetate=1/1) to afford the title compound as a gray powder (200 mg, 65%). MS (ESI) calcd for C₂₅H₂₉F₅N₆O: 524.2; found: 525.3 [M+H].

Step 6. (±)-N-(3,3-difluoro-1-(4-(trifluoromethyl)phenethyl)piperidin-4-yl)-1H-pyrazolo-[3,4-b]pyridin-4-amine

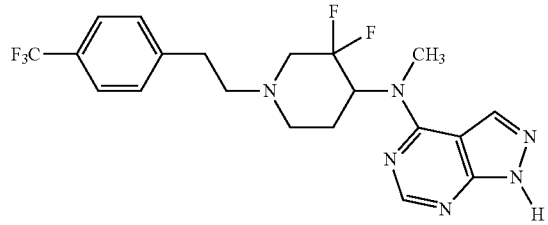 [SMILES: CN(c1ncnc2[nH]ncc12)C1CCN(CCc2ccc(C(F)(F)F)cc2)CC1(F)F]

To a stirred solution of (±)-N-(3,3-difluoro-1-(4-(trifluoromethyl)phenethyl)piperidin-4-yl)-N-methyl-1-(tetrahydro-2H-pyran-2-yl)-1H-pyrazolo[3,4-d]pyrimidin-4-amine (200 mg, 0.38 mmol) in MeOH (4.0 mL) was added HCl/Et₂O (2 M, 4 mL) at rt. After stirring overnight, the mixture was concentrated. The concentrate was neutralized with 1 N NaOH, and extracted with ethyl acetate. The combined organic phases were washed with brine, dried Na₂SO₄, and concentrated to afford the title compound as an off-white powder (138 mg, 83%). MS (ESI) calcd for C₂₀H₂₁F₅N₆: 440.2; found: 441.5 [M+H]. ¹H NMR (400 MHz, CD₃OD) δ 9.04 (s, 1H), 8.69 (s, 1H), 7.70 (d, J=8.0 Hz, 2H), 7.59 (d, J=8.0 Hz, 2H), 6.47-6.37 (m, 1H), 4.34-4.28 (m, 1H), 4.05-3.94 (m, 2H), 3.71 (s, 3H), 3.66-3.61 (m, 3H), 3.32-3.23 (m, 1H), 2.85-2.75 (m, 1H), 2.49-2.42 (m, 1H).

Example 1.5a. (±)-N-(3,3-difluoro-1-(4-(trifluoromethyl)phenethyl)piperidin-4-yl)-N-methyl-1H-pyrazolo[3,4-d]pyrimidin-4-amine hydrochloride (C-1.33a)

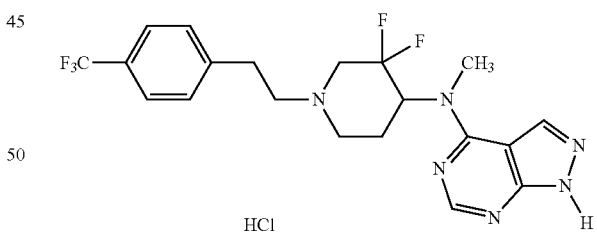

To a stirred solution of (±)-N-(3,3-difluoro-1-(4-(trifluoromethyl)phenethyl)piperidin-4-yl)-1H-pyrazolo[3,4-b]pyridin-4-amine (138 mg, 0.32 mmol) in MeOH (2 mL) was added HCl/ether (0.16 mL, 2 N, 0.32 mmol) at room temperature. After stirred for 10 min, the mixture was concentrated to afford the product as a white solid (146 mg, 98%). MS (ESI) calcd for C₂₀H₂₁F₅N₆: 440.2; found: 441.5 [M+H]. ¹H NMR (400 MHz, CD₃OD) δ 9.04 (s, 1H), 8.69 (s, 1H), 7.70 (d, J=8.0 Hz, 2H), 7.59 (d, J=8.0 Hz, 2H), 6.47-6.37 (m, 1H), 4.34-4.28 (m, 1H), 4.05-3.94 (m, 2H), 3.71 (s, 3H), 3.66-3.62 (m, 3H), 3.31-3.27 (m, 1H), 2.85-2.75 (m, 1H), 2.46-2.42 (m, 1H).

Example 1.6. (R*)-N-(1-(4-chlorophenethyl)-3,3-difluoropiperidin-4-yl)-1H-pyrazolo[3,4-d]-pyrimidin-4-amine (E1-1.3)

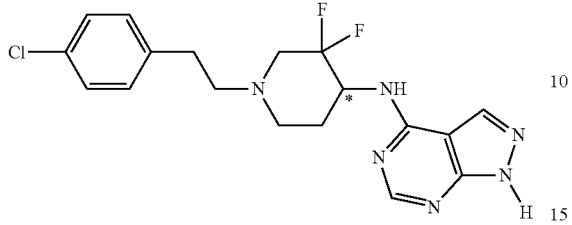

To a solution of 2-(4-chlorophenyl)acetaldehyde (50 mg, 0.3 mmol) and (R*)-N-(3,3-difluoropiperidin-4-yl)-1H-pyrazolo[3,4-d]pyrimidin-4-amine (90 mg, 0.27 mmol) in MeOH (2 mL) was added 4 drops of AcOH. The resulting mixture was stirred for 30 min at room temperature, followed by addition of NaBH$_3$CN (38 mg, 0.6 mmol). The mixture thus obtained was stirred for an additional 15 min at room temperature. The reaction mixture was concentrated. The concentrate was taken up in EtOAc and filtered. The filtrate was concentrated under reduced pressure and purified by column chromatography over silica gel (dichloromethane/MeOH=25/1) to afford the product as a yellow solid (80 mg, 74%). MS (ESI) calcd for C$_{18}$H$_{19}$ClF$_2$N$_6$: 392.1; found: 393.2 [M+H]. $^1$H NMR (400 MHz, CD$_3$OD) δ 8.28 (s, 1H), 8.26 (s, 1H), 7.30 (d, J=8.8 Hz, 2H), 7.26 (d, J=8.8 Hz, 2H), 4.98-4.91 (m, 1H), 3.38-3.34 (m, 1H), 3.11-3.08 (m, 1H), 2.87-2.83 (m, 2H), 2.79-2.71 (m, 2H), 2.61-2.51 (m, 1H), 2.45-2.39 (m, 1H), 2.07-1.92 (m, 2H).

Example 1.6a. (R*)-N-(1-(4-chlorophenethyl)-3,3-difluoropiperidin-4-yl)-1H-pyrazolo[3,4-d]-pyrimidin-4-amine hydrochloride (E1-1.3a)

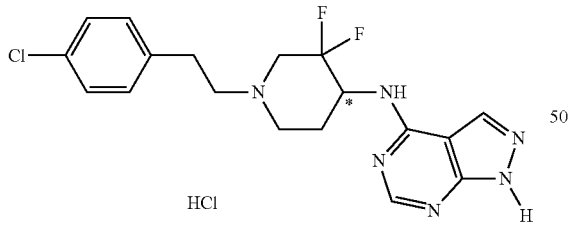

To a solution of (R*)-N-(1-(4-chlorophenethyl)-3,3-difluoropiperidin-4-yl)-1H-pyrazolo-[3,4-d]pyrimidin-4-amine (71 mg, 0.18 mmol) in MeOH (1.0 mL) was added HCl/MeOH (90 μL, 2 N, 0.18 mmol) at rt. After stirred for 10 min, the mixture was concentrated to afford the product as white solid (78 mg, 98%). MS (ESI) calcd for C$_{18}$H$_{19}$ClF$_2$N$_6$: 392.1; found: 393.2 [M+H]. $^1$H NMR (400 MHz, CD$_3$OD) δ 8.56 (s, 1H), 8.54 (s, 1H), 7.39 (d, J=8.8 Hz, 2H), 7.34 (d, J=8.8 Hz, 2H), 5.50-5.36 (m, 1H), 4.19-4.09 (m, 1H), 3.80-3.61 (m, 2H), 3.43-3.41 (m, 2H), 3.16-3.08 (m, 2H), 2.46-2.26 (m, 2H).

Example 1.7. (S*)-N-(1-(4-chlorophenethyl)-3,3-difluoropiperidin-4-yl)-1H-pyrazolo[3,4-d]pyrimidin-4-amine (E2-1.3)

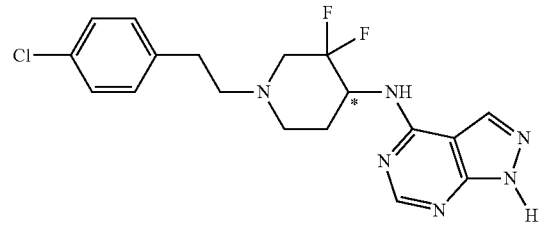 [SMILES: FC1(F)CN(CCc2ccc(Cl)cc2)CCC1Nc1ncnc2[nH]ncc12]

To a stirred solution of 2-(4-chlorophenyl)acetaldehyde (50 mg, 0.3 mmol) and (S*)-N-(3,3-difluoropiperidin-4-yl)-1H-pyrazolo[3,4-d]pyrimidin-4-amine (100 mg, 0.3 mmol) in MeOH (2 mL) was added 4 drops of AcOH. The resulting mixture was stirred for 30 min at room temperature and NaBH$_3$CN (38 mg, 0.6 mmol) was added. The mixture was stirred for 15 min at room temperature and concentrated in vacuo. The concentrate was taken up in EtOAc and the mixture was filtered. The filtrate was concentrated under reduced pressure and the concentrate was purified by column chromatography over silica gel (dichloromethane/MeOH=25/1) to afford the title compound as a yellow solid (76 mg, 65%). MS (ESI) calcd for C$_{18}$H$_{19}$ClF$_2$N$_6$: 392.1; found: 393.2 [M+H]. $^1$H NMR (400 MHz, CD$_3$OD) δ 8.26 (s, 1H), 8.25-8.22 (m, 1H), 7.30 (d, J=8.8 Hz, 2H), 7.26 (d, J=8.8 Hz, 2H), 4.96-4.88 (m, 1H), 3.37-3.33 (m, 1H), 3.11-3.08 (m, 1H), 2.87-2.82 (m, 2H), 2.77-2.72 (m, 2H), 2.62-2.51 (m, 1H), 2.45-2.39 (m, 1H), 2.10-1.95 (m, 2H).

Example 1.7a. (S*)-N-(1-(4-chlorophenethyl)-3,3-difluoropiperidin-4-yl)-1H-pyrazolo[3,4-d]-pyrimidin-4-amine hydrochloride (E2-1.3a)

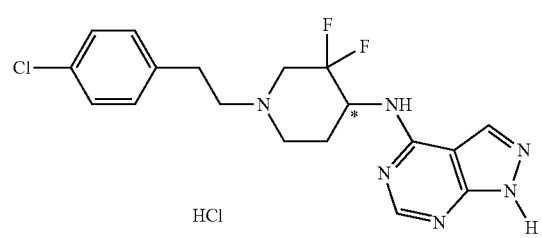 [SMILES: FC1(F)CN(CCc2ccc(Cl)cc2)CCC1Nc1ncnc2[nH]ncc12 ; Cl]

To a solution of (S*)-N-(1-(4-chlorophenethyl)-3,3-difluoropiperidin-4-yl)-1H-pyrazolo-[3,4-d]-pyrimidin-4-amine (73 mg, 0.18 mmol) in MeOH (0.9 mL) was added HCl/MeOH (90 μL, 2 N, 0.18 mmol) at rt. After stirred for 10 min, the mixture was concentrated to afford the product as a white solid (78 mg, 99%). MS (ESI) calcd for C$_{18}$H$_{19}$ClF$_2$N$_6$: 392.1; found: 393.2 [M+H].

Example 1.8. (±)-N-(3,3-difluoro-1-(4-fluorophen-ethyl)piperidin-4-yl)-1H-pyrazolo[3,4-d]-pyrimidin-4-amine (C-1.2)

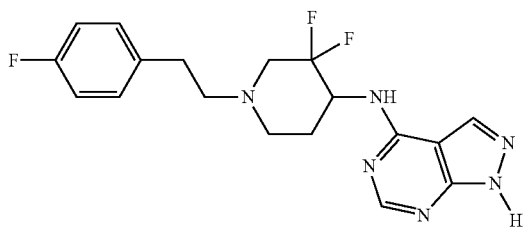 [SMILES: Fc1ccc(CCN2CCC(Nc3ncnc4[nH]ncc34)C(F)(F)C2)cc1]

Step 1. 2-(4-fluorophenyl)acetaldehyde

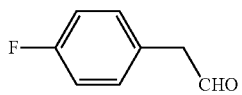

To a stirred solution of the 2-(4-fluorophenyl) ethanol (200 mg, 1.43 mmol) in MeCN (4 mL) was added 2-iodoxybenzoic acid (1.2 g, 4.3 mmol). The resulting mixture was heated to 80° C. After stirred for 2 hrs, the mixture was cooled to room temperature, and filtered through a pad of celite. The filtrate was concentrated to afford the title compound as a pale yellow oil (197 mg, 100%) which was used in the next step without further purification. $^1$H NMR (400 MHz, CDCl$_3$) δ 9.77 (t, J=2.0 Hz, 1H), 7.22-7.14 (m, 2H), 7.10-7.01 (m, 2H), 3.70 (t, J=2.0 Hz, 2H).

Step 2. (±)-N-(3,3-difluoro-1-(4-fluorophenethyl)piperidin-4-yl)-1H-pyrazolo[3,4-d]-pyrimidin-4-amine

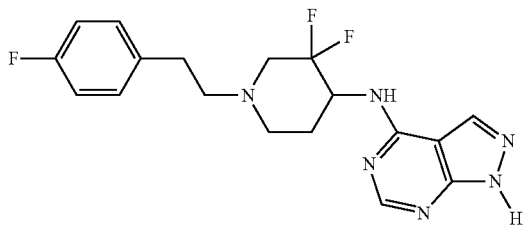 [SMILES: Fc1ccc(CCN2CCC(Nc3ncnc4[nH]ncc34)C(F)(F)C2)cc1]

To a stirred solution of 2-(4-fluorophenyl)acetaldehyde (197 mg, 1.43 mmol) in MeOH (4 mL) were added (±)-N-(3,3-difluoropiperidin-4-yl)-1H-pyrazolo[3,4-d]pyrimidin-4-amine (363 mg, 1.43 mmol) and 2 drops of AcOH. The resulting mixture was stirred at r.t. for 30 min, followed by addition of NaBH$_3$CN (180 mg, 2.86 mmol). The mixture was stirred for additional 15 min, concentrated and taken up in EtOAc. The organic phase was washed with water, brine, dried over anhydrous Na$_2$SO$_4$ and concentrated. The residue was purified by column chromatography over silica gel (DCM/MeOH=30/1) to afford the title compound as a white powder (296 mg, 55%). MS (ESI) calcd for C$_{18}$H$_{19}$F$_3$N$_6$: 376.2; found: 377.2 [M+H]. $^1$H NMR (400 MHz, CD$_3$OD) δ 8.28 (s, 1H), 8.26 (s, 1H), 7.29-7.26 (m, 2H), 7.04-6.99 (m, 2H), 4.95-4.92 (m, 1H), 3.38-3.33 (m, 1H), 3.15-3.08 (m, 1H), 2.86-2.79 (m, 2H), 2.78-2.68 (m, 2H), 2.63-2.49 (m, 1H), 2.46-2.36 (m, 1H), 2.06-1.93 (m, 2H).

Example 1.8a. (±)-N-(3,3-difluoro-1-(4-fluorophen-ethyl)piperidin-4-yl)-1H-pyrazolo[3,4-d]-pyrimidin-4-amine hydrochloride (C-1.2a)

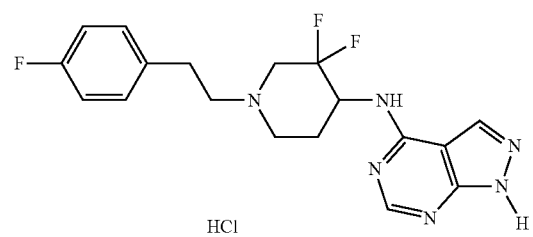 [SMILES: Fc1ccc(CCN2CCC(Nc3ncnc4[nH]ncc34)C(F)(F)C2)cc1 ; Cl]

To a stirred solution of (±)-N-(3,3-difluoro-1-(4-fluorophenethyl)piperidin-4-yl)-1H-pyrazolo-[3,4-d]pyrimidin-4-amine (150 mg, 0.4 mmol) in MeOH (3 mL) was added HCl/MeOH (0.2 mL, 2 N, 0.4 mmol) at r.t. After stirred for 10 min, the mixture was concentrated to afford the title compound as a white solid (164 mg, 99%). MS (ESI) calcd for C$_{18}$H$_{19}$F$_3$N$_6$: 376.2; found: 377.2 [M+H]. $^1$H NMR (400 MHz, CD$_3$OD) δ 8.45 (s, 2H), 7.38-7.34 (m, 2H), 7.13-7.07 (m, 2H), 5.41-5.31 (m, 1H), 4.06-4.03 (m, 1H), 3.74-3.71 (m, 1H), 3.64-3.47 (m, 1H), 3.39-3.35 (m, 1H), 3.28-3.25 (m, 1H), 3.16-3.06 (m, 2H), 2.44-2.18 (m, 2H).

Example 1.9. (±)-N-(1-(3,4-difluorophenethyl)-3,3-difluoropiperidin-4-yl)-1H-pyrazolo-[3,4-d]-pyrimidin-4-amine (C-1.15)

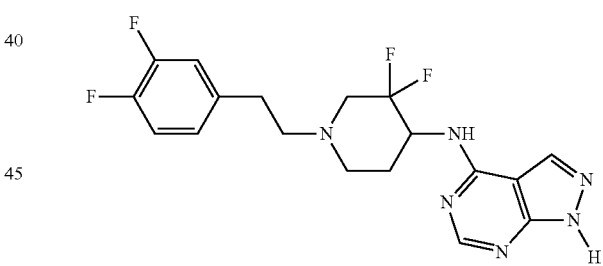

Step 1. Ethyl 2-(3,4-difluorophenyl)acetate

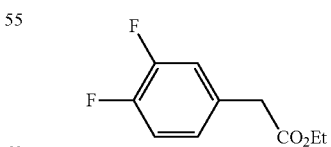

To a stirred solution of 2-(3,4-difluorophenyl)acetic acid (500 mg, 3.62 mmol) in EtOH (10 mL) was added SOCl$_2$ (0.1 ml, 1.1 mmol) dropwise at 0-5° C. After completion of the addition, the reaction was heated to reflux for 1 hr. The mixture was concentrated and diluted with EtOAc. The EtOAc layer was washed with sat. NaHCO$_3$, brine, dried over Na₂SO₄ and concentrated. The residue was purified by column chromatography over silica gel (Hex/EtOAc=3/1) to afford the title compound as a colorless oil (551 mg, 96%). ¹H NMR (400 MHz, CDCl₃) δ 7.24-7.21 (m, 1H), 6.87-6.77 (m, 2H), 4.17 (q, J=7.2 Hz, 2H), 3.62 (s, 2H), 1.26 (t, J=7.2 Hz, 3H).

Step 2. 2-(3,4-difluorophenyl)ethanol

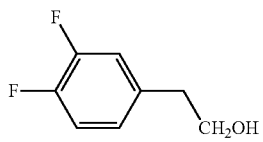

To a stirred solution of ethyl 2-(3,4-difluorophenyl)acetate (450 mg, 2.25 mmol) in ethanol (9 mL) was added NaBH₄ (255 mg, 6.75 mmol) slowly at room temperature. The resulting mixture was stirred for 30 min, then quenched with 1N aqueous HCl under ice-water bath cooling and concentrated under vacuum. The residue was partitioned into EtOAc and water. The EtOAc layer was washed with water, brine, dried over Na₂SO₄ and concentrated. The residue was purified by column chromatography over silica gel (Hex/EtOAc=3/1) to afford the title compound as a colorless oil (221 mg, 62%). ¹H NMR (400 MHz, CDCl₃) δ 7.24-7.18 (m, 1H), 6.85-6.77 (m, 2H), 3.87-3.81 (m, 2H), 2.88 (t, J=6.8 Hz, 2H), 1.48-1.43 (m, 1H).

Step 3. 2-(3,4-difluorophenyl)acetaldehyde

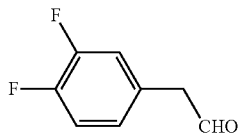 [SMILES: O=CCc1ccc(F)c(F)c1]

To a stirred solution of 2-(3,4-difluorophenyl)ethanol (220 mg, 1.27 mmol) in MeCN (6 mL) was added 2-iodoxybenzoic acid (1.06 g, 3.8 mmol). The mixture was heated at 80° C. with stirring for 2 hrs. The mixture was cooled to room temperature, and filtered through a pad of celite. The filtrate was concentrated to afford the product as a pale yellow oil (156 mg, 72%) which was used directly without further purification. ¹H NMR (400 MHz, CDCl₃) δ 9.78 (s, 1H), 7.22-7.16 (m, 1H), 6.94-6.87 (m, 2H), 3.75 (s, 2H).

Step 4. (±)-N-(1-(3,4-difluorophenethyl)-3,3-difluoropiperidin-4-yl)-1H-pyrazolo-[3,4-d]-pyrimidin-4-amine To a stirred solution of 2-(3,4-difluorophenyl)acetaldehyde (150 mg, 0.96 mmol) in MeOH (3 mL) were added (±)-N-(3,3-difluoropiperidin-4-yl)-1H-pyrazolo[3,4-d]pyrimidin-4-amine (244 mg, 0.96 mmol) and 4 drops AcOH, and the resulting mixture was stirred at r.t. After stirred for 30 min, NaBH₃CN (121 mg, 1.92 mmol) was added into the reaction mixture, and the mixture thus obtained was stirred for additional 15 min. The mixture was concentrated and extracted with EtOAc. The organic phase was washed with water, brine, dried over anhydrous Na₂SO₄ and concentrated. The residue was purified by column chromatography over silica gel (DCM/MeOH=20/1) to afford the title compound as a white powder (233 mg, 62%). MS (ESI) calcd for C₁₈H₁₈F₄N₆: 394.2; found: 395.2 [M+H]. ¹H NMR (400 MHz, CD₃OD) δ 8.28 (s, 1H), 8.25 (s, 1H), 7.38-7.32 (m, 1H), 6.95-6.89 (m, 2H), 3.16-3.09 (m, 1H), 2.92-2.83 (m, 2H), 2.79-2.70 (m, 2H), 2.64-2.51 (m, 1H), 2.47-2.37 (m, 1H), 2.07-1.93 (m, 2H).

Example 1.9a. (±)-N-(1-(3,4-difluorophenethyl)-3,3-difluoropiperidin-4-yl)-1H-pyrazolo-[3,4-d]-pyrimidin-4-amine hydrochloride (C-1.15a)

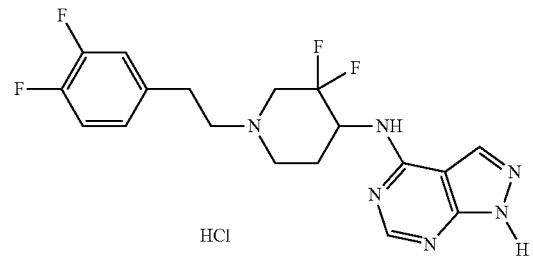 [SMILES: Fc1ccc(CCN2CCC(Nc3ncnc4[nH]ncc34)C(F)(F)C2)cc1F ; Cl]

To a solution of (±)-N-(1-(3,4-difluorophenethyl)-3,3-difluoropiperidin-4-yl)-1H-pyrazolo-[3,4-d]pyrimidin-4-amine (150 mg, 0.38 mmol) in MeOH (4 mL) was added HCl/MeOH (0.19 mL, 2 N, 0.38 mmol) at r.t. After stirring for 10 min, the mixture was concentrated to afford the title compound as an off-white solid (158 mg, 96%). MS (ESI) calcd for C₁₈H₁₈F₄N₆: 394.2; found: 395.2 [M+H]. ¹H NMR (400 MHz, CD₃OD) δ 8.48 (brs, 2H), 7.45-7.39 (m, 1H), 7.04-6.96 (m, 2H), 5.38-5.24 (m, 1H), 4.03-3.95 (m, 1H), 3.67-3.60 (m, 1H), 3.54-3.40 (m, 1H), 3.30-3.26 (m, 2H), 3.21-3.05 (m, 3H), 2.36-2.19 (m, 2H).

Example 1.10. (±)-N-(3,3-difluoro-1-(4-(trifluoromethyl)phenethyl)piperidin-4-yl)-3-methyl-1H-pyrazolo[3,4-d]pyrimidin-4-amine (C-1.34)

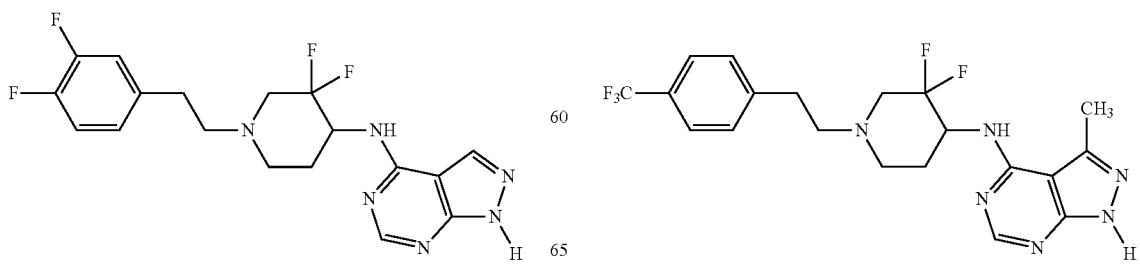

Step 1. (±)-tert-butyl 3,3-difluoro-4-(3-methyl-1-(tetrahydro-2H-pyran-2-yl)-1H-pyrazolo-[3,4-d]pyrimidin-4-ylamino)piperidine-1-carboxylate

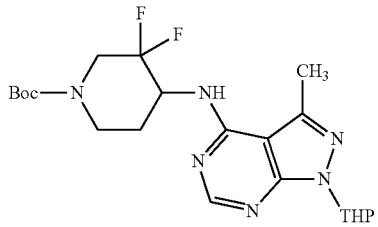

A mixture of (±)-tert-butyl 4-amino-3,3-difluoropiperidine-1-carboxylate (350 mg, 1.48 mmol), 4-chloro-3-methyl-1-(tetrahydro-2H-pyran-2-yl)-1H-pyrazolo[3,4-d]pyrimidine (393 mg, 1.55 mmol) and DIPEA (0.55 ml, 2.96 mmol) in n-BuOH (5 mL) was heated to 120° C. After stirring overnight at 120° C., the orange solution was concentrated. The residue was purified by column chromatography over silica gel (hexane/ethyl acetate=1:1) to afford the title compound as a gray powder (311 mg, 46%). $^1$H NMR (400 MHz, CDCl$_3$) δ 8.38 (s, 1H), 5.91-5.86 (m, 1H), 5.39-5.29 (m, 1H), 5.05-4.89 (m, 1H), 4.53-4.24 (m, 1H), 4.35-4.29 (m, 1H), 4.14-4.10 (m, 1H), 3.80-3.74 (m, 1H), 3.24-2.86 (m, 2H), 2.64 (s, 3H), 2.61-2.48 (m, 1H), 2.20-2.08 (m, 2H), 1.92-1.87 (m, 1H), 1.82-1.69 (m, 3H), 1.60-1.58 (m, 2H), 1.49 (s, 9H).

Step 2. (±)-N-(3,3-difluoropiperidin-4-yl)-3-methyl-1H-pyrazolo[3,4-d]pyrimidin-4-amine dihydrochloride

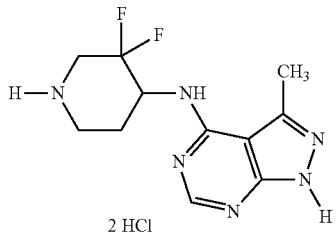 [SMILES: Cc1n[nH]c2ncnc(NC3CCNCC3(F)F)c12]

To a stirred solution of (±)-3,3-difluoro-4-[3-methyl-1-(tetrahydro-pyran-2-yl)-1H-pyrazolo[3,4-d]pyrimidin-4-ylamino]-piperidine-1-carboxylic acid tert-butyl ester (311 mg, 0.68 mmol) in MeOH (4.0 mL) was added HCl/Et$_2$O (2 M, 4 mL) at room temperature. After stirring overnight, the mixture was concentrated to afford the title compound as an off-white powder (230 mg, 99%) which was used directly without further purification.

Step 3. (±)-N-(3,3-difluoro-1-(4-(trifluoromethyl)phenethyl)piperidin-4-yl)-3-methyl-1H-pyrazolo[3,4-d]pyrimidin-4-amine

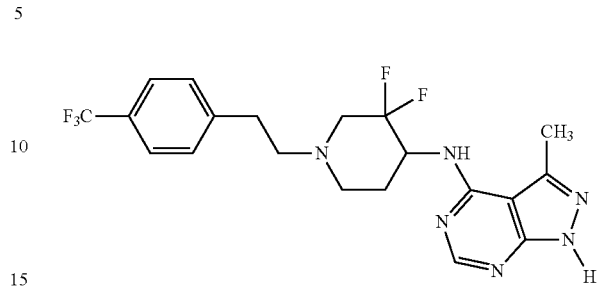

A mixture of 1-(2-bromoethyl)-4-(trifluoromethyl)benzene (380 mg, 1.5 mmol), (±)-N-(3,3-difluoropiperidin-4-yl)-3-methyl-1H-pyrazolo[3,4-d]pyrimidin-4-amine dihydrochloride (230 mg, 0.7 mmol) and DIPEA (0.6 mL, 3.44 mmol) in n-BuOH (4 mL) was heated to 120° C. After stirring overnight at 120° C., the mixture was concentrated. The concentrate was purified by column chromatography over silica gel (DCM/MeOH=20/1) to afford the title compound as a gray powder (105 mg, 34%). MS (ESI) calcd for C$_{20}$H$_{21}$F$_5$N$_6$:440.2; found: 441.4 [M+H]. $^1$H NMR (400 MHz, CD$_3$OD) δ 8.26 (s, 1H), 7.60 (d, J=8.0 Hz, 2H), 7.48 (d, J=8.0 Hz, 2H), 5.02-4.91 (m, 1H), 3.41-3.35 (m, 1H), 3.11-3.09 (m, 1H), 2.97-2.91 (m, 2H), 2.84-2.76 (m, 2H), 2.68 (s, 3H), 2.62-2.52 (m, 1H), 2.46-2.40 (m, 1H), 2.11-1.98 (m, 2H).

Example 1.10a. (±)-N-(3,3-difluoro-1-(4-(trifluoromethyl)phenethyl)piperidin-4-yl)-3-methyl-1H-pyrazolo[3,4-d]pyrimidin-4-amine hydrochloride (C-1.34a)

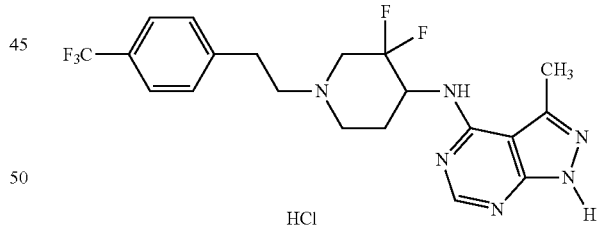

To a stirred solution of (±)-N-(3,3-difluoro-1-(4-(trifluoromethyl)phenethyl)piperidin-4-yl)-3-methyl-1H-pyrazolo[3,4-d]pyrimidin-4-amine (95 mg, 0.216 mmol) in MeOH (3 mL) was added HCl/ether (0.11 mL, 2.0 M, 0.22 mmol) at room temperature. After stirring for 10 min, the mixture was concentrated to afford the title compound as a white solid (102 mg, 100%). MS (ESI) calcd for C$_{20}$H$_{21}$F$_5$N$_6$: 440.2; found: 441.4 [M+H]. $^1$H NMR (400 MHz, CD$_3$OD) δ 8.52 (s, 1H), 7.58 (d, J=8.0 Hz, 2H), 7.46 (d, J=8.0 Hz, 2H), 5.67-5.55 (m, 1H), 4.17-4.12 (m, 1H), 3.80-3.68 (m, 2H), 3.47-3.43 (m, 2H), 3.41-3.34 (m, 1H), 3.17-3.12 (m, 2H), 2.77 (s, 3H), 2.60-2.49 (m, 1H), 2.34-2.30 (m, 1H).

Example 1.11. (±)-N-(1-(2,5-difluorophenethyl)-3,3-difluoropiperidin-4-yl)-1H-pyrazolo[3,4-d]-pyrimidin-4-amine (C-1.35)

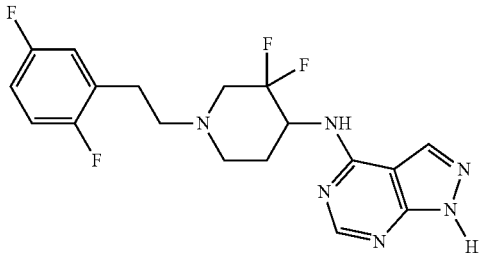 [SMILES: Fc1ccc(F)c(CCN2CCC(Nc3ncnc4[nH]ncc34)C(F)(F)C2)c1]

Step 1. Ethyl 2-(2,5-difluorophenyl)acetate

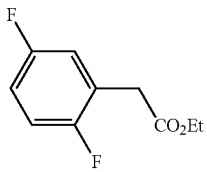 [SMILES: CCOC(=O)Cc1cc(F)ccc1F]

To a stirred solution of 2-(2,5-difluorophenyl)acetic acid (5.0 g, 29 mmol) in ethanol (100 mL) was added concentrated $H_2SO_4$ (5.0 mL) and the mixture was heated at reflux overnight. The mixture was cooled to rt and concentrated to remove the solvent. The concentrate was partitioned into EtOAc and water. The organic phase was washed with saturated $NaHCO_3$, brine, dried over $Na_2SO_4$ and concentrated to afford the title compound as a pale yellow liquid (3.0 g, 86%). $^1$H NMR (400 MHz, $CDCl_3$) δ 7.05-6.90 (m, 3H), 4.18 (q, J=7.2 Hz, 2H), 3.64 (s, 2H), 1.26 (t, J=7.2, 3H).

Step 2. 2-(2,5-difluorophenyl)ethanol

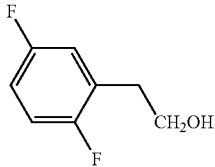 [SMILES: OCCc1cc(F)ccc1F]

To a solution of ethyl 2-(2,5-difluorophenyl)acetate (2.64 g, 13.2 mmol) in ethanol (50 mL) was added $NaBH_4$ (1.0 g, 26 mmol). The mixture was stirred at room temperature and gradually a clear solution was obtained. After stirring for an additional 30 min, the reaction mixture was quenched with 1.0N aqueous HCl under ice-water bath cooling. The mixture was concentrated and the concentrate was partitioned into the EtOAc/water. The organic phase was washed with saturated $NaHCO_3$, brine, dried over $Na_2SO_4$ and concentrated. The residue was purified by column chromatography over silica gel (hexane/EtOAc=20/1) to afford the title compound as a colorless oil (1.6 g, 80%). $^1$H NMR (400 MHz, $CDCl_3$) δ 7.02-6.94 (m, 2H), 6.92-6.85 (m, 1H), 3.88 (q, J=6.4 Hz, 2H), 2.90 (t, J=6.4 Hz, 2H).

Step 3. 2-(2,5-difluorophenyl)acetaldehyde

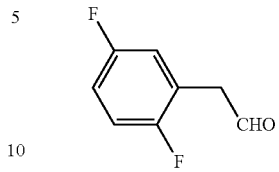

To a stirred solution of 2-(2,5-difluorophenyl)ethanol (200 mg, 1.26 mmol) in MeCN (5 mL) was added 2-iodoxybenzoic acid (1.0 g, 3.80 mmol). The resulting suspension was heated to reflux for 1 h. The mixture was cooled to room temperature and filtered. The filtrate was concentrated to give the crude title compound which was used in the next step without further purification (160 mg, 81%). $^1$H NMR (400 MHz, $CDCl_3$) δ 9.76 (s, 1H), 7.10-7.03 (m, 1H), 7.05-6.95 (m, 1H), 6.95-6.89 (m, 1H), 3.74 (s, 2H).

Step 4. (±)-N-(1-(2,5-difluorophenethyl)-3,3-difluoropiperidin-4-yl)-1H-pyrazolo[3,4-d]pyrimidin-4-amine

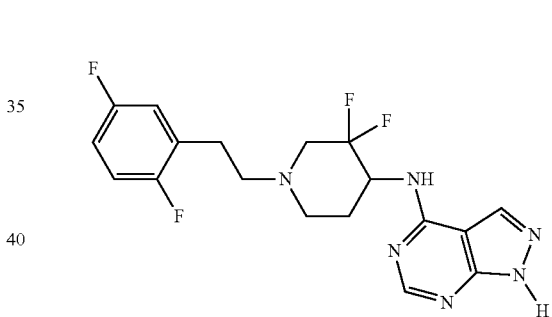

To a stirred solution of 2-(2,5-difluorophenyl)acetaldehyde (160 mg, 1.02 mmol) and (±)-N-(3,3-difluoropiperidin-4-yl)-1H-pyrazolo[3,4-d]pyrimidin-4-amine (260 mg, 1.02 mmol) in methanol (3 mL) was added a catalytic amount HOAc. After stirring for 30 min at room temperature, $NaBH(OAc)_3$ (130 mg, 2.05 mmol) was slowly added into the reaction mixture. The mixture was concentrated and then treated with saturated aqueous $NaHCO_3$. The aqueous phase was extracted with ethyl acetate. The combined organic phases were washed with brine, dried over $Na_2SO_4$ and concentrated. The residue was purified by column chromatography over silica gel (DCM/EtOAc=1/2) to afford the title compound as a white powder (182 mg, 45%). MS (ESI) calcd for $C_{18}H_{18}F_4N_6$: 394.2; found: 395.2 [M+H]. $^1$H NMR (400 MHz, $CD_3OD$) δ 8.26 (s, 1H), 8.25-8.22 (m, 1H), 7.14-7.02 (m, 2H), 6.99-6.91 (m, 1H), 4.96-4.90 (m, 1H), 3.36-3.32 (m, 1H), 3.12-3.05 (m, 1H), 2.94-2.82 (m, 2H), 2.81-2.70 (m, 2H), 2.63-2.48 (m, 1H), 2.44-2.34 (m, 1H), 2.06-1.90 (m, 2H).

Example 1.11a. (±)-N-(1-(2,5-difluorophenethyl)-3,3-difluoropiperidin-4-yl)-1H-pyrazolo[3,4-d]-pyrimidin-4-amine hydrochloride (C-1.35a)

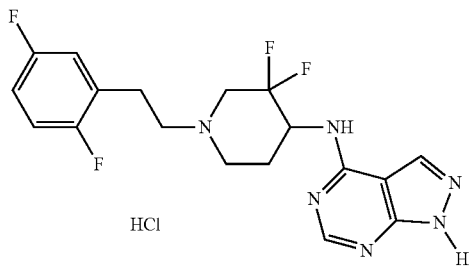 [SMILES: Fc1ccc(F)c(CCN2CCC(Nc3ncnc4[nH]ncc34)C(F)(F)C2)c1 ; Cl]

To a stirred solution of (±)-N-(1-(2,5-difluorophenethyl)-3,3-difluoropiperidin-4-yl)-1H-pyrazolo-[3,4-d]pyrimidin-4-amine (182 mg, 0.46 mmol) in methanol (3 mL) was added 2.0M HCl solution in methanol (0.23 mL, 0.46 mmol) at room temperature. The resulting clear solution was stirred for 30 min and concentrated to afford the title compound as a white powder (198 mg, 100%). MS (ESI) calcd for $C_{18}H_{18}F_4N_6$: 394.2; found: 395.2 [M+H]. $^1$H NMR (400 MHz, $CD_3OD$) δ 8.70-8.60 (m, 1H), 8.58 (s, 1H), 7.22-7.136 (m, 2H), 7.10-7.04 (m, 1H), 5.50-5.36 (m, 1H), 4.18-4.03 (m, 1H), 3.81-3.78 (m, 1H), 3.72-3.58 (m, 1H), 3.45-3.37 (m, 2H), 3.19-3.11 (m, 2H), 2.45-2.26 (m, 2H).

Example 1.12. (R*)-N-(1-(4-(difluoromethyl)phenethyl)-3,3-difluoropiperidin-4-yl)-1H-pyrazolo-[3,4-d]pyrimidin-4-amine (E1-1.6)

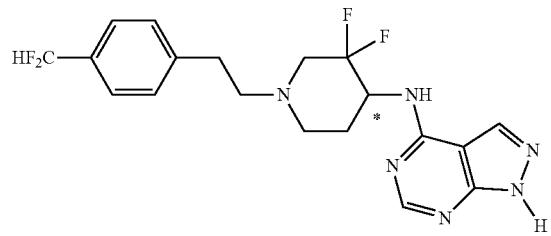

Step 1. methyl 2-(4-(difluoromethyl)phenyl)acetate

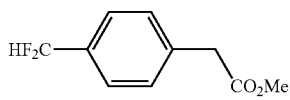

To a stirred solution of methyl 2-(4-formylphenyl)-acetate (1.75 g, 9.83 mmol) in DCM (20 mL) was added DAST (0.96 mL, 7.75 mmol) at 0° C. After stirring for 15 min, the mixture was allowed to warm to room temperature, and stirred overnight. The reaction was quenched with water at 0° C., followed by neutralization with solid $NaHCO_3$ until no gas was evolved. The aqueous layer was extracted with DCM. The combined organic layers were washed with brine, dried over $Na_2SO_4$ and concentrated. The residue was purified by column chromatography over silica gel (Hex/EtOAc=10/1) to afford the title compound as a colorless liquid (790 mg, 40%). $^1$H NMR (400 MHz, $CDCl_3$) δ 7.47 (d, J=8.0 Hz, 2H), 7.37 (d, J=8.0 Hz, 2H), 6.63 (t, J=56.4 Hz, 1H), 3.70 (s, 3H), 3.67 (s, 2H).

Step 2. 2-(4-(difluoromethyl)phenyl)acetaldehyde

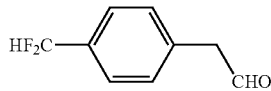

To a solution of methyl 2-(4-(difluoromethyl)phenyl) acetate (350 mg, 1.75 mmol) in dried THF (7 mL) was added dropwise DIBAL (1.0 M, 1.9 mL, 1.9 mmol) with stirring at −78° C. under $N_2$. After stirring for 2 h, the reaction was quenched by addition of 3.0N aqueous HCl (7.0 mL) at −78° C. After stirring for an additional 15 min, the mixture was allowed to warm to room temperature. The aqueous layer was extracted with $Et_2O$. The combined organic layers were washed with aqueous $NaHCO_3$, brine, dried over $Na_2SO_4$ and concentrated to give the title compound (300 mg, ca. 80%).which was used directly in the next step without further purification.

Step 3. (R*)-N-(1-(4-(difluoromethyl)phenethyl)-3,3-difluoropiperidin-4-yl)-1H-pyrazolo-[3,4-d]pyrimidin-4-amine

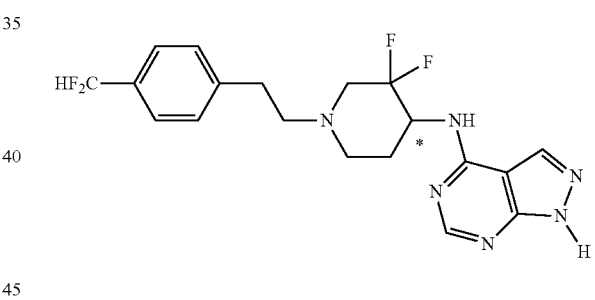

To a solution of 2-(4-(difluoromethyl)phenyl)acetaldehyde (182 mg, 0.92 mmol) and (R*)-N-(3,3-difluoropiperidin-4-yl)-1H-pyrazolo[3,4-d]pyrimidin-4-amine dihydrochloride (200 mg, 0.61 mmol) in MeOH (4 mL) was added TEA (0.25 mL, 1.84 mmol) and 4 drops of AcOH. After stirred at room temperature for 30 min, $NaBH_3CN$ (77 mg, 1.23 mmol) was added and the mixture was stirred for an additional 15 min. The reaction mixture was concentrated and the concentrate was taken up in EtOAc. The organic phase was washed with brine, dried over $Na_2SO_4$ and concentrated. The residue was purified by column chromatography over silica gel (DCM/MeOH=25/1) to afford the title compound as a white solid (121 mg, 48%). MS (ESI) calcd for $C_{19}H_{20}ClF_4N_6$:408.2; found: 409.3 [M+H]. $^1$H NMR (400 MHz, $CD_3OD$) δ 8.26 (s, 1H), 8.25 (s, 1H), 7.46 (d, J=8.0 Hz, 2H), 7.38 (d, J=8.0 Hz, 2H), 6.72 (t, J=56.4 Hz, 1H), 4.95-4.84 (m, 1H), 3.37-3.33 (m, 1H), 3.18-3.08 (m, 1H), 2.94-2.85 (m, 2H), 2.82-2.71 (m, 2H), 2.61-2.51 (m, 1H), 2.44-2.38 (m, 1H), 2.05-1.92 (m, 2H).

Example 1.12a. (R*)-N-(1-(4-(difluoromethyl)phenethyl)-3,3-difluoropiperidin-4-yl)-1H-pyrazolo-[3,4-d]pyrimidin-4-amine hydrochloride (E1-1.6a)

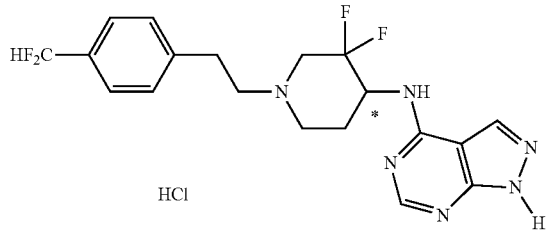

To a solution of (R*)-N-(1-(4-(difluoromethyl)phenethyl)-3,3-difluoropiperidin-4-yl)-1H-pyrazolo [3,4-d]pyrimidin-4-amine (110 mg, 0.27 mmol) in MeOH (3 mL) was added HCl/MeOH (0.135 mL, 2 N, 0.27 mmol) at rt. After stirring for 10 min, the mixture was concentrated to afford the title compound as a white solid (120 mg, 98%). MS (ESI) calcd for $C_{19}H_{20}ClF_4N_6$:408.2; found: 409.2 [M+H]. $^1$H NMR (400 MHz, $CD_3OD$) δ 8.47 (s, 2H), 7.56 (d, J=8.0 Hz, 2H), 7.47 (d, J=8.0 Hz, 2H), 6.78 (t, J=56.4 Hz, 1H), 5.40-5.31 (m, 1H), 4.10-4.02 (m, 1H), 3.73-3.70 (m, 1H), 3.63-3.51 (m, 1H), 3.41-3.39 (m, 1H), 3.29-3.22 (m, 1H), 3.20-3.10 (m, 2H), 2.40-2.19 (m, 2H).

Example 1.13. (S*)-N-(1-(4-(difluoromethyl)phenethyl)-3,3-difluoropiperidin-4-yl)-1H-pyrazolo-[3,4-d]-pyrimidin-4-amine (E2-1.6)

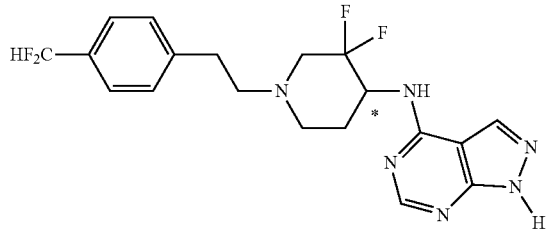

To a solution of 2-(4-(difluoromethyl)phenyl)acetaldehyde (185 mg, 0.92 mmol) and (S*)-N-(3,3-difluoropiperidin-4-yl)-1H-pyrazolo[3,4-d]pyrimidin-4-amine dihydrochloride (200 mg, 0.61 mmol) in MeOH (4 mL) were added TEA (0.25 mL, 1.84 mol) and 4 drops of AcOH. The resulting mixture was stirred at ambient temperature for 30 min, followed by addition of $NaBH_3CN$ (77 mg, 1.23 mmol). The reaction mixture stirred for additional 15 min., concentrated, and the concentrate was taken up in with EtOAc. The organic phase was washed with brine, dried over $Na_2SO_4$ and concentrated. The residue was purified by HPLC to afford the title compound as a white solid (62 mg, 25%), 99% ee. (Column: CHIRALPAKAD-H4.6*150 mm, 5 um; Mobile Phase: A: Hexanes B: Isopropyl Alcohol=75: 25; t=11.62). MS (ESI) calcd for $C_{19}H_{20}ClF_4N_6$:408.2; found: 409.3 [M+H]. $^1$H NMR (400 MHz, $CD_3OD$) δ 8.28 (s, 1H), 8.26 (s, 1H), 7.48 (d, J=8.0 Hz, 2H), 7.40 (d, J=8.0 Hz, 2H), 6.75 (t, J=56.4 Hz, 1H), 4.91-4.86 (m, 1H), 3.37-3.33 (m, 1H), 3.18-3.08 (m, 1H), 2.94-2.85 (m, 2H), 2.84-2.74 (m, 2H), 2.63-2.53 (m, 1H), 2.46-2.39 (m, 1H), 2.05-1.97 (m, 2H).

Example 1.13a. (S*)-N-(1-(4-(difluoromethyl)phenethyl)-3,3-difluoropiperidin-4-yl)-1H-pyrazolo[3,4-d]-pyrimidin-4-amine hydrochloride (E2-1.6a)

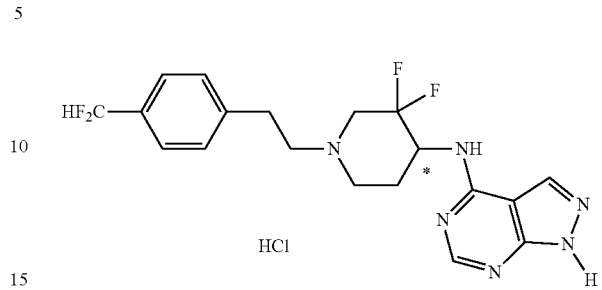

To a solution of (S*)-N-(1-(4-(difluoromethyl)phenethyl)-3,3-difluoropiperidin-4-yl)-1H-pyrazolo [3,4-d]pyrimidin-4-amine (47 mg, 0.12 mmol) in MeOH (3 mL) was added HCl/MeOH (0.06 mL, 2 N, 0.12 mmol) at rt. After stirring for 10 min, the mixture was concentrated to afford the title compound as a white solid (51 mg, 100%). MS (ESI) calcd for $C_{19}H_{20}ClF_4N_6$:408.2; found: 409.3 [M+H].

Example 1.14. (R*)-N-(3,3-difluoro-1-(4-methylphenethyl)piperidin-4-yl)-1H-pyrazolo[3,4-d]-pyrimidin-4-amine (E1-1.4)

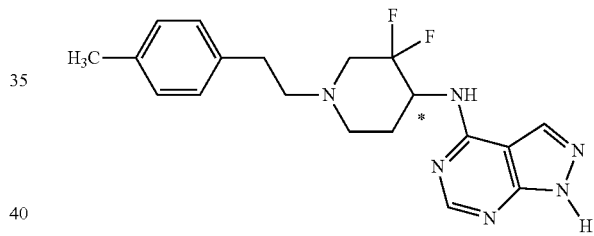

To a stirred solution of 2-p-tolylacetaldehyde (50 mg, 0.3 mmol) and (R*)-N-(3,3-difluoropiperidin-4-yl)-1H-pyrazolo[3,4-d]pyrimidin-4-amine (90 mg, 0.27 mmol) in MeOH (2 mL) were added 4 drops of AcOH. The resulting mixture was stirred for 30 min at room temperature, followed by addition of $NaBH_3CN$ (38 mg, 0.6 mmol). The mixture thus obtained was stirred for an additional 15 min at room temperature. The reaction mixture was concentrated and diluted with EtOAc. The resulting suspension was filtered, and the filtrate was concentrated under reduced pressure. The residue was purified by column chromatography over silica gel (dichloromethane/MeOH=25/1) to afford the title compound as a yellow solid (78 mg, 74%.>99% ee (Column: CHIRALPAKAD-H4.6*150 mm, 5 um; Mobile Phase: A: Hexanes B: Isopropyl Alcohol=70:30; t=2.86) MS (ESI) calcd for $C_{19}H_{22}F_2N_6$: 372.2; found: 373.3 [M+H]. $^1$H NMR (400 MHz, $CD_3OD$) δ 8.28 (s, 1H), 8.26 (s, 1H), 7.14 (d, J=8.4 Hz, 2H), 7.10 (d, J=8.4 Hz, 2H) 4.97-4.92 (m, 1H), 3.39-3.35 (m, 1H), 3.12-3.09 (m, 1H), 2.84-2.78 (m, 2H), 2.75-2.69 (m, 2H), 2.61-2.50 (m, 1H), 2.45-2.38 (m, 1H), 2.31 (s, 3H), 2.05-1.97 (m, 2H).

Example 1.14a. (R*)-N-(3,3-difluoro-1-(4-ethyl-phenethyl)piperidin-4-yl)-1H-pyrazolo[3,4-d]-pyrimidin-4-amine hydrochloride (E1-1.4a)

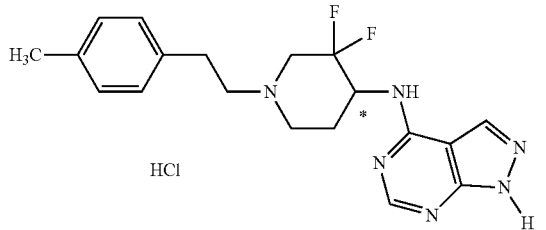 [SMILES: Cc1ccc(CCN2CCC(Nc3ncnc4[nH]ncc34)C(F)(F)C2)cc1 ; Cl]

To a stirred solution of (R*)-N-(3,3-difluoro-1-(4-methylphenyl)piperidin-4-yl)-1H-pyrazolo[3,4-d]pyrimidin-4-amine (70 mg, 0.19 mmol) in MeOH (0.9 mL) was added HCl in MeOH (0.095 mL, 2 N, 0.19 mmol) at rt. After stirring for 10 min, the mixture was concentrated to afford the title compound as a white solid (78 mg, 99%). MS (ESI) calcd for $C_{19}H_{22}F_2N_6$: 372.2; found: 373.3 [M+H]. $^1$H NMR (400 MHz, CD$_3$OD) δ 8.86 (brs, 1H), 8.73 (s, 1H), 7.24 (d, J=8.0 Hz, 2H), 7.19 (d, J=8.0 Hz, 2H), 5.65-5.56 (m, 1H), 4.33-4.28 (m, 1H), 3.97-3.86 (m, 2H), 3.57-3.53 (m, 3H), 3.20-3.08 (m, 2H), 2.56-2.38 (m, 2H), 2.34 (s, 3H).

Example 1.15. (S*)-N-(3,3-difluoro-1-(4-methyl-phenethyl)piperidin-4-yl)-1H-pyrazolo[3,4-d]-pyrimidin-4-amine (E2-1.4)

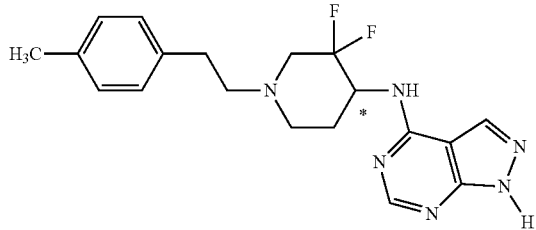

To a stirred solution of 2-p-tolylacetaldehyde (50 mg, 0.3 mmol) and (S*)-N-(3,3-difluoropiperidin-4-yl)-1H-pyrazolo[3,4-d]pyrimidin-4-amine (100 mg, 0.3 mmol) in MeOH (2 mL) were added 4 drops of AcOH at room temperature. After 30 min, NaBH$_3$CN (38 mg, 0.6 mmol) was added. After stirring for 15 min at room temperature, the reaction mixture was concentrated and diluted with EtOAc. The suspension was filtered. The organic phase was concentrated under reduced pressure and purified by column chromatography over silica gel (dichloromethane/MeOH=25/1) to afford the title compound as a yellow solid (77 mg, 65%)>99% ee (Column: CHIRALPAKAD-H4.6*150 mm, 5 um; Mobile Phase: A: Hexanes B: Isopropyl Alcohol=70:30; t=4.03). MS (ESI) calcd for $C_{19}H_{22}F_2N_6$: 372.19; found: 373.3 [M+H]. $^1$H NMR (400 MHz, CD$_3$OD) δ 8.28 (s, 1H), 8.26 (s, 1H), 7.14 (d, J=8.4 Hz, 2H), 7.10 (d, J=8.4 Hz, 2H), 4.96-4.88 (m, 1H), 3.39-3.35 (m, 1H), 3.12-3.09 (m, 1H), 2.85-2.77 (m, 2H), 2.76-2.68 (m, 2H), 2.61-2.51 (m, 1H), 2.45-2.38 (m, 1H), 2.31 (s, 3H), 2.06-1.98 (m, 2H).

Example 1.15a. (S*)-N-(3,3-difluoro-1-(4-methyl-phenethyl)piperidin-4-yl)-1H-pyrazolo[3,4-d]-pyrimidin-4-amine hydrochloride (E2-1.4a)

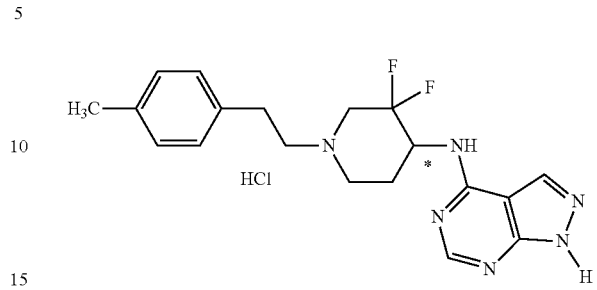

To a stirred solution of (S*)-N-(3,3-difluoro-1-(4-methylphenethyl)piperidin-4-yl)-1H-pyrazolo[3,4-d]-pyrimidin-4-amine (68 mg, 0.18 mmol) in methanol (1.0 mL) was added 2.0N methanolic HCl (90 μL, 0.18 mmol). The mixture was stirred for 30 min at room temperature, and then concentrated under vacuum. The residue was treated with ether to afford the title product as an off-white powder (74 mg, 99%). MS (ESI) calcd for $C_{119}H_{22}F_2N_6$: 372.19; found: 373.3 [M+H].

Example 1.16. (R*)-N-(3,3-difluoro-1-(4-(fluoromethyl)phenethyl)piperidin-4-yl)-1H-pyrazolo[3,4-d]-pyrimidin-4-amine (E1-1.7)

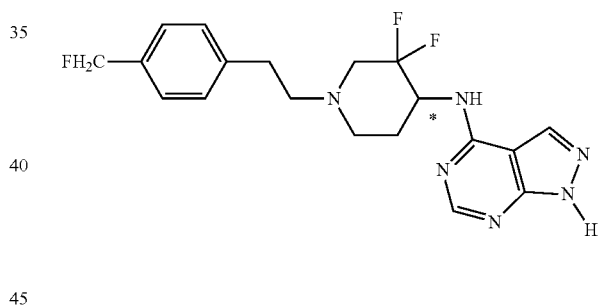

Step 1. methyl 2-(4-(hydroxymethyl)phenyl)acetate

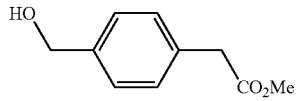

A mixture of 2-(4-(hydroxymethyl)phenyl)acetic acid (1.2 g, 7.2 mmol) and p-toluenesulfonic acid (70 mg, 0.41 mmol) in methyl alcohol (20 mL) was heated under reflux for 13 hours under N$_2$ atmosphere. The mixture was allowed to cool to room temperature and concentrated under reduced pressure. The residue was taken up in ether and the organic phase was washed with brine, dried over anhydrous Na$_2$SO$_4$ and concentrated. The residue was purified by column chromatography over silica gel (EtOAc/Hex=1/5) to afford the title compound as a colorless oil (1.15 g, 88%). $^1$H NMR (400 MHz, CDCl$_3$) δ 7.32 (d, J=8.4 Hz, 2H), 7.27 (d, J=8.4 Hz, 2H), 4.67 (s, 2H), 3.69 (s, 3H), 3.63 (s, 2H).

Step 2. methyl 2-(4-(fluoromethyl)phenyl)acetate

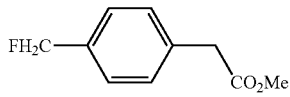

To a stirred solution of methyl 2-(4-(hydroxymethyl) phenyl)acetate (1.0 g, 5.5 mmol) in DCM (20 mL) was added DAST (0.55 mL, 8.2 mmol) at room temperature. The resulting mixture was stirred for 13 hours, quenched with water and neutralized with aqueous NaHCO$_3$ under ice-water bath cooling. The aqueous phase was extracted with DCM and the combined organic phases were washed with brine, dried over anhydrous Na$_2$SO$_4$ and concentrated. The residue was purified by column chromatography over silica gel (EtOAc/Hex=1/10) to afford the title compound as a colorless oil (360 mg, 31%). $^1$H NMR (400 MHz, CDCl$_3$) δ 7.35 (d, J=7.2 Hz, 2H), 7.33 (d, J=7.2 Hz, 2H), 5.36 (d, J=56.0 Hz, 2H), 3.69 (s, 3H), 3.65 (s, 2H).

Step 3. 2-(4-(fluoromethyl)phenyl)acetaldehyde

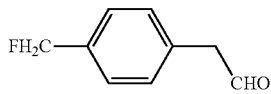

To a stirred solution of methyl 2-(4-(fluoromethyl)phenyl)acetate (360 mg, 2.0 mmol) was added DIBAL in toluene (2.2 mL, 1.0 M, 2.2 mmol) at −78° C. The resulting solution was stirred at −78° C. for 30 min and quenched by the addition of aqueous HCl (3 mL, 3.0 N). The mixture was diluted with water and extracted with Et$_2$O. The combined organic phases were washed with brine, dried over anhydrous Na$_2$SO$_4$, and concentrated to afford the title compound as a colorless oil (400 mg, 100%) which was used in the next step without further purification. $^1$H NMR (400 MHz, CDCl$_3$) δ 9.75 (t, J=2.4 Hz, 1H), 7.40 (d, J=7.8 Hz, 2H), 7.24 (d, J=7.8 Hz, 2H), 5.40 (d, J=47.6 Hz, 2H), 3.72 (s, 2H).

Step 4. (R*)-N-(3,3-difluoro-1-(4-(fluoromethyl) phenethyl)piperidin-4-yl)-1H-pyrazolo-[3,4-d]py- rimidin-4-amine

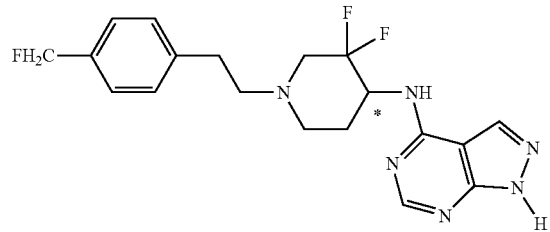

To a stirred solution of crude 2-(4-(fluoromethyl)phenyl) acetaldehyde (230 mg, 1.5 mmol) and (R*)-N-(3,3-difluoropiperidin-4-yl)-1H-pyrazolo[3,4-d]pyrimidin-4-amine dihydrochloride (200 mg, 0.6 mmol) in MeOH (3 mL) were added TEA (180 mg, 1.8 mol) and 2 drops of AcOH. The mixture was stirred at room temperature for 30 min and NaBH$_3$CN (77 mg, 1.2 mmol) was added. The mixture was stirred for 15 min and concentrated. The concentrate was taken up in EtOAc, and the resulting suspension was filtered. The filtrate was concentrated under reduced pressure, and the residue was purified by column chromatography over silica gel (DCM/MeOH=25/1) to afford the title compound as a yellow solid (175 mg, 53%). MS (ESI) calcd for C$_{19}$H$_{21}$F$_3$N$_6$: 390.2; found: 391.3 [M+H]. $^1$H NMR (400 MHz, CD$_3$OD) δ 8.28 (s, 1H), 8.26 (s, 1H), 7.36-7.30 (m, 4H), 5.34 (d, J=48.0 Hz, 2H), 4.96-4.86 (m, 1H), 3.39-3.35 (m, 1H), 3.12-3.10 (m, 1H), 2.91-2.86 (m, 2H), 2.82-2.73 (m, 2H), 2.62-2.52 (m, 1H), 2.46-2.39 (m, 1H), 2.06-1.94 (m, 2H).

Example 1.16a. (R*)-N-(3,3-difluoro-1-(4-(fluoromethyl)phenethyl)piperidin-4-yl)-1H-pyrazolo[3,4-d]-pyrimidin-4-amine hydrochloride (E1-1.7a)

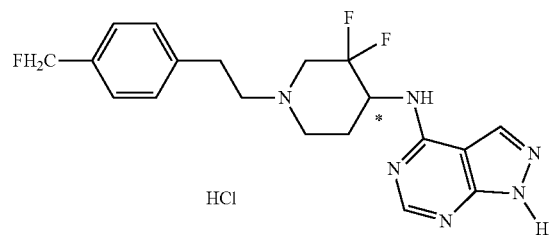

To a stirred solution of (R*)-N-(3,3-difluoro-1-(4-(fluoromethyl)phenethyl)piperidin-4-yl)-1H-pyrazolo[3,4-d]pyrimidin-4-amine (165 mg, 0.42 mmol) in MeOH (5 mL) was added HCl in MeOH (0.21 mL, 2.0 N, 0.42 mmol) at rt. After stirring for 10 min, the mixture was concentrated to afford the title compound as a white solid (172 mg, 99%). MS (ESI) calcd for C$_{19}$H$_{21}$F$_3$N$_6$: 390.2; found: 391.3 [M+H]. $^1$H NMR (400 MHz, CD$_3$OD) δ 8.52 (brs, 2H), 7.43-7.38 (m, 4H), 5.50-5.35 (m, 1H), 5.37 (d, J=48.0 Hz, 2H), 4.18-4.12 (m, 1H), 3.81-3.65 (m, 2H), 3.48-3.44 (m, 2H), 3.40-3.35 (m, 1H), 3.22-3.09 (m, 2H), 2.44-2.27 (m, 2H)

Example 1.17. (S*)-N-(3,3-difluoro-1-(4-(fluoromethyl)phenethyl)piperidin-4-yl)-1H-pyrazolo-[3,4-d]-pyrimidin-4-amine (E2-1.7) C-25a-1-(S)

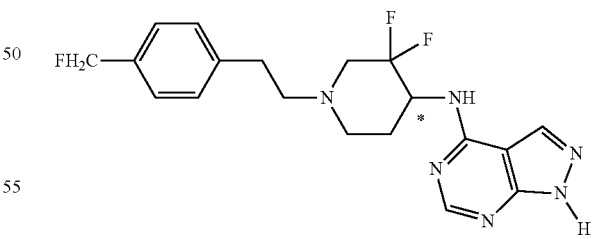

To a stirred solution of crude 2-(4-(fluoromethyl)phenyl) acetaldehyde (170 mg, 1.1 mmol)) and (S*)-N-(3,3-difluoropiperidin-4-yl)-1H-pyrazolo[3,4-d]pyrimidin-4-amine dihydrochloride (130 mg, 0.4 mmol) in MeOH (3 mL) were added TEA (0.13 mL, 1.0 mmol) and 2 drops of AcOH. After stirring for 30 min at room temperature, NaBH$_3$CN (100 mg, 1.5 mmol) was added. The mixture was stirred for 15 min at room temperature and concentrated. The residue was taken up in EtOAc and the resulting suspension was filtered. The filtrate was concentrated under reduced pressure and the residue was purified by column chromatography over silica gel (dichloromethane/MeOH=25/1) to afford the title compound as a yellow solid (105 mg, 53%). MS (ESI) calcd for $C_{19}H_{21}F_3N_6$: 390.2; found: 391.3 [M+H]. $^1$H NMR (400 MHz, CD$_3$OD) δ 8.28 (s, 1H), 8.26 (s, 1H), 7.36-7.30 (m, 4H), 5.34 (d, J=48.0 Hz, 2H), 4.99-4.86 (m, 1H), 3.39-3.35 (m, 1H), 3.13-3.09 (m, 1H), 2.92-2.85 (m, 2H), 2.81-2.73 (m, 2H), 2.62-2.52 (m, 1H), 2.46-2.40 (m, 1H), 2.09-1.94 (m, 2H).

Example 1.17a. (S*)-N-(3,3-difluoro-1-(4-(fluoromethyl)phenethyl)piperidin-4-yl)-1H-pyrazolo[3,4-d]pyrimidin-4-amine hydrochloride (E2-1.7a)

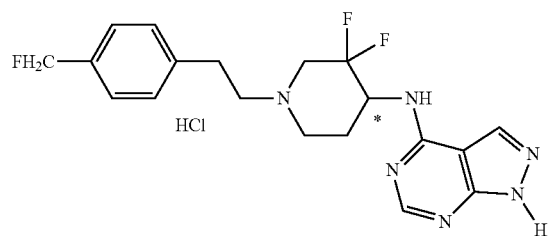

To a solution of (S*)-N-(1-(4-chloro-2-fluorophenethyl)-3,3-difluoropiperidin-4-yl)-1H-pyrazolo[3,4-d]pyrimidin-4-amine (95 mg, 0.24 mmol) in MeOH (3 mL) was added HCl/MeOH (0.12 mL, 2 N, 0.24 mmol) at rt. After stirring for 10 min, the mixture was concentrated to afford the title compound as a white solid (100 mg, 97%). MS (ESI) calcd for $C_{19}H_{21}F_3N_6$:390.2; found: 391.3 [M+H]. Example 1.18. (±)-N-(3,3-difluoro-1-(2-(6-(trifluoromethyl)pyridin-3-yl)ethyl)piperidin-4-yl)-1H-pyrazolo[3,4-d]pyrimidin-4-amine (C-3.5)

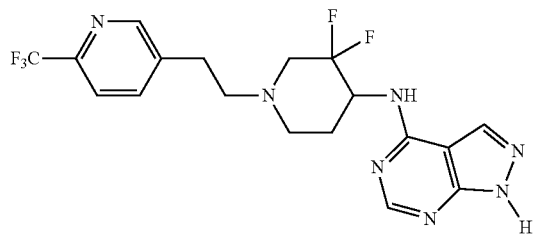 [SMILES: FC(F)(F)c1ccc(CCN2CCC(Nc3ncnc4[nH]ncc34)C(F)(F)C2)cn1]

Step 1. (E)-5-(2-ethoxyvinyl)-2-(trifluoromethyl)pyridine

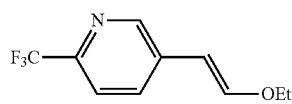 [SMILES: CCO/C=C/c1ccc(C(F)(F)F)nc1]

To a stirred solution of 5-iodo-2-(trifluoromethyl)pyridine (0.2 g, 0.7 mmol) and (E)-2-(2-ethoxyvinyl)-4,4,5,5-tetramethyl-1,3,2-dioxaborolane (290 mg, 1.47 mmol) in DME/H$_2$O (16 mL/4 mL) were added Pd(PPh$_3$)$_4$ (42.8 mg, 0.037 mmol) and Na$_2$CO$_3$ (156 mg, 1.47 mmol) under nitrogen. The resulting mixture was stirred at 75° C. for 3 hr and allowed to cool to room temperature. The mixture was concentrated and extracted with EtOAc. The combined organic phases were washed with H$_2$O, brine, dried over anhydrous Na$_2$SO$_4$ and concentrated. The residue was purified by column chromatography over silica gel (Hex/EtOAc=20/1) to afford the title compound as an oil (85 mg, 76%) comprising a ca. 70:30 mixture of E/Z isomers.

Step 2. 2-(6-(trifluoromethyl)pyridin-3-yl)acetaldehyde

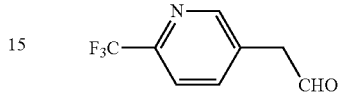

To a stirred solution of 5-(2-ethoxyvinyl)-2-(trifluoromethyl)pyridine (80 mg, 0.37 mmol) in DCM (2 mL) was added HCl (3.5 mL, 3.0 N). The mixture was stirred at 80° C. for 30 min under nitrogen. The resulting mixture was cooled to room temperature and extracted with DCM. The combined organic phases were washed with brine, dried over anhydrous Na$_2$SO$_4$, and concentrated to afford the product as a white solid which was used in the next step without further purification (60 mg, 96%).

Step 3. (±)-N-(3,3-difluoro-1-(2-(6-(trifluoromethyppyridin-3-yl)ethyl)piperidin-4-yl)-1H-pyrazolo[3,4-d]pyrimidin-4-amine

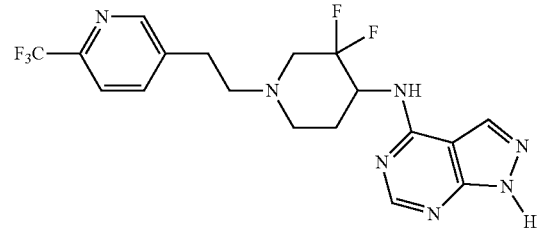

To a solution of 2-(6-(trifluoromethyl)pyridin-3-yl)acetaldehyde (80 mg, 0.421 mmol) and (±)-N-(3,3-difluoropiperidin-4-yl)-1H-pyrazolo[3,4-d]pyrimidin-4-amine (150 mg, 0.46 mmol) in MeOH (3 mL) were added 2 drops of AcOH. The resulting mixture was stirred for 30 min at room temperature, followed by addition of NaBH$_3$CN (164 mg, 2.6 mmol). After stirring for 30 min, the reaction mixture was concentrated. The residue was taken up in EtOAc, and the suspension was filtered. The filtrate was concentrated under reduced pressure and the residue was purified by column chromatography over silica gel (dichloromethane/MeOH=25/1) to afford the title compound as a yellow solid (109 mg, 60%). MS (ESI) calcd for $C_{18}H_{18}F_5N_7$: 427.2; found: 428.2 [M+H]. $^1$H NMR (400 MHz, CD$_3$OD) δ 8.66 (s, 1H), 8.28 (s, 1H), 8.25 (s, 1H), 7.99 (d, J=8.0 Hz, 1H), 7.76 (d, J=8.0 Hz, 1H), 4.98-4.93 (m, 1H), 3.39-3.35 (m, 1H), 3.10-3.07 (m, 1H), 3.01-2.97 (m, 2H), 2.88-2.79 (m, 2H), 2.63-2.53 (m, 1H), 2.46-2.41 (m, 1H), 2.05-1.93 (m, 2H).

Example 1.18a. (±)-N-(3,3-difluoro-1-(2-(6-(trifluoromethyl)pyridin-3-yl)ethyl)piperidin-4-yl)-1H-pyrazolo[3,4-d]pyrimidin-4-amine hydrochloride (C-3.5a)

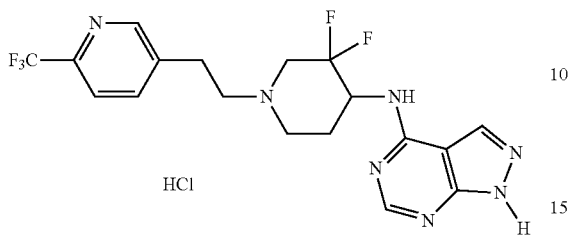

To a solution of N-(3,3-difluoro-1-(2-(6-(trifluoromethyl)pyridin-3-yl)ethyl)piperidin-4-yl)-1H-pyrazolo[3,4-d]pyrimidin-4-amine (104 mg, 0.24 mmol) in MeOH (2 mL) was added HCl in MeOH (0.12 mL, 2.0 N, 0.24 mmol) at rt. After stirring for 10 min, the mixture was concentrated to afford the title compound as a white solid (110 mg, 96%). MS (ESI) calcd for $C_{18}H_{18}F_5N_7$: 427.2; found: 428.2 [M+H]. $^1$H NMR (400 MHz, CD$_3$OD) δ 8.75 (s, 1H), 8.73 (s, 1H), 8.66 (s, 1H), 8.07 (d, J=8.0 Hz, 1H), 7.84 (d, J=8.0 Hz, 1H), 5.53-5.43 (m, 1H), 4.22-4.12 (m, 1H), 3.80-3.77 (m, 1H), 3.71-3.64 (m, 1H), 3.51-3.47 (m, 2H), 3.37-3.26 (m, 2H), 2.47-2.32 (m, 2H).

Example 1.19. (±)-N-(3,3-difluoro-1-(2-(6-methylpyridin-3-yl)ethyl)piperidin-4-yl)-1H-pyrazolo[3,4-d]pyrimidin-4-amine (C-3.4)

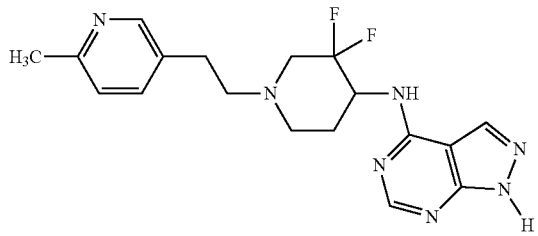 [SMILES: FC(F)(F)c1ccc(CCN2CCC(Nc3ncnc4[nH]ncc34)C(F)(F)C2)cn1]

Step 1. 5-(2-ethoxyvinyl)-2-methylpyridine

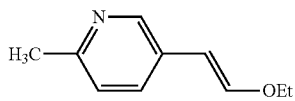

To a solution of 5-iodo-2-methylpyridine (1.0 g, 4.5 mmol) and (E)-2-(2-ethoxyvinyl)-4,4,5,5-tetramethyl-1,3,2-dioxaborolane (1.8 g, 9.0 mmol) in DME/H$_2$O (24 mL/6 mL) was added Pd(PPh$_3$)$_4$ (266 mg, 0.23 mmol) and Na$_2$CO$_3$ (965 mg, 9.1 mmol) under nitrogen. The reaction mixture was stirred at 75° C. for 12 hr and cooled to room temperature. The mixture was concentrated and extracted with EtOAc. The combined organic phases were washed with water, brine, dried over anhydrous Na$_2$SO$_4$ and concentrated. The residue was purified by column chromatography over silica gel (Hex/EtOAc=20/1) to afford the title compound (400 mg, 54%). as an oil comprising a mixture (cs. 6:5 ratio) of E/Z-isomers $^1$H NMR (400 MHz, CDCl$_3$) δ For E-isomer: 8.55 (d, J=2.0 Hz, 1H), 7.89 (dd, J=2.0 and 8.0 Hz, 1H), 7.07 (d, J=8.4 Hz, 1H), 6.99 (d, J=12.8 Hz, 1H), 5.75 (d, J=12.8 Hz, 1H), 3.93 (q, J=6.8 Hz, 2H), 2.51 (s, 3H), 1.37 (t, J=6.8 Hz, 3H). For Z-isomer: 8.33 (d, J=2.4 Hz, 1H), 7.41 (dd, J=2.4 and 8.4 Hz, 1H), 7.54 (d, J=8.4 Hz, 1H), 6.28 (d, J=6.8 Hz, 1H), 5.16 (d, J=6.8 Hz, 1H), 3.90 (q, J=6.8 Hz, 2H), 2.50 (s, 3H), 1.36 (t, J=6.8 Hz, 3H).

Step 2. 2-(6-methylpyridin-3-yl)acetaldehyde

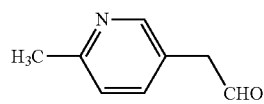

To a solution of 5-(2-ethoxyvinyl)-2-methylpyridine (160 mg, 0.99 mmol) in DCM (2 mL) was added 3N aqueous HCl (3.5 mL) under nitrogen. The resulting mixture was stirred at 80° C. for 30 min. The reaction mixture was then extracted with DCM. The organic phase was washed with brine, dried over anhydrous Na$_2$SO$_4$, and concentrated to afford the title product as a white solid which was used in the next step without further purification (120 mg, 91%).

Step 3. (±)-N-(3,3-difluoro-1-(2-(6-methylpyridin-3-yl)ethyl)piperidin-4-yl)-1H-pyrazolo-[3,4-d]pyrimidin-4-amine

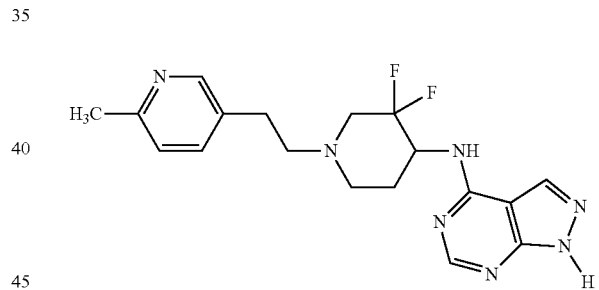

To a solution of 2-(6-methylpyridin-3-yl) acetaldehyde (110 mg, 0.80 mmol) and (±)-N-(3,3-difluoropiperidin-4-yl)-1H-pyrazolo[3,4-d]pyrimidin-4-amine (140 mg, 0.54 mmol) in MeOH (3 mL) were added 2 drops of AcOH. The mixture thus obtained was stirred at ambient temperature for 30 min, followed by addition of NaBH$_3$CN (78 mg, 1.2 mmol). The resulting mixture was stirred for an additional 15 min at room temperature. The reaction mixture was concentrated. The residue was taken up in EtOAc, and the resulting suspension was filtered. The filtrate was concentrated and the concentrate was purified by column chromatography over silica gel (dichloromethane/MeOH=25/1) to afford the title compound as a yellow solid (120 mg, 58%). MS (ESI) calcd for $C_{18}H_{21}F_2N_7$: 373.2; found: 374.3 [M+H]. $^1$H NMR (400 MHz, CD$_3$OD) δ 8.21 (d, J=2.0 Hz, 1H), 8.16 (s, 1H), 8.14 (s, 1H), 7.55 (dd, J=7.6, 2.0 Hz, 1H), 7.13 (d, J=7.6 Hz, 1H), 4.85-4.74 (m, 1H), 3.26-3.23 (m, 1H), 2.99-2.96 (m, 1H), 2.76-2.72 (m, 2H), 2.69-2.59 (m, 2H), 2.50-2.43 (m, 1H), 2.40 (s, 3H), 2.33-2.28 (m, 1H), 1.93-1.82 (m, 2H).

Example 1.19a. (±)-N-(3,3-difluoro-1-(2-(6-methyl-pyridin-3-yl)ethyl)piperidin-4-yl)-1H-pyrazolo-[3,4-d]pyrimidin-4-amine hydrochloride (C-3.4a)

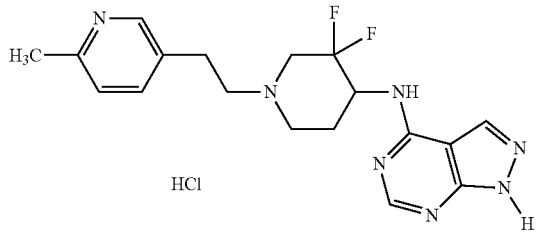 [SMILES: FC(F)(F)c1ccc(CCN2CCC(Nc3ncnc4[nH]ncc34)C(F)(F)C2)cn1 ; Cl]

To a solution of (±)-N-(3,3-difluoro-1-(2-(6-methylpyridin-3-yl)ethyl)piperidin-4-yl)-1H-pyrazolo[3,4-d]pyrimidin-4-amine (110 mg, 0.29 mmol) in MeOH (2 mL) was added HCl in MeOH (0.14 mL, 2 N, 0.28 mmol) at rt. After stirring for 10 min, the mixture was concentrated to afford the title compound as a white solid (118 mg, 98%). MS (ESI) calcd for $C_{18}H_{18}F_5N_7$: 373.2; found: 374.3 [M+H]. $^1$H NMR (400 MHz, $CD_3OD$) δ 8.68 (d, J=1.6 Hz, 1H), 8.55-8.45 (m, 3H), 7.85 (d, J=8.0 Hz, 1H), 5.12-5.01 (m, 1H), 3.58-3.49 (m, 1H), 3.26-3.23 (m, 1H), 3.13-3.09 (m, 2H), 3.05-2.97 (m, 2H), 2.89-2.82 (m, 1H), 2.78 (s, 3H), 2.68-2.62 (m, 1H), 2.20-2.00 (m, 2H).

Example 1.20. (R*)-N-(1-(4-chloro-2-fluorophenethyl)-3,3-difluoropiperidin-4-yl)-1H-pyrazolo-[3,4-d]pyrimidin-4-amine (E1-1.16)

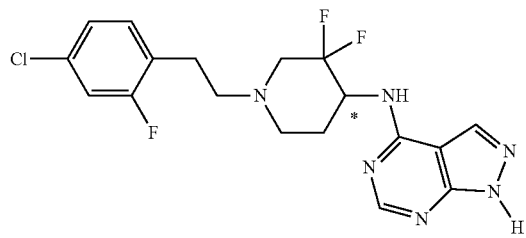 [SMILES: Fc1cc(Cl)ccc1CCN1CCC(Nc2ncnc3[nH]ncc23)C(F)(F)C1]

Step 1. 2-(4-chloro-2-fluorophenyl)acetaldehyde

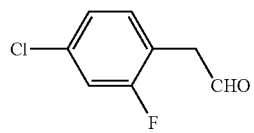 [SMILES: O=CCc1ccc(Cl)cc1F]

To a stirred solution of 1-bromo-4-chloro-2-fluorobenzene (0.9 g, 4.32 mmol) and (E)-2-(2-ethoxyvinyl)-4,4,5,5-tetramethyl-1,3,2-dioxaborolane (1.5 g, 7.5 mmol) in DME/$H_2O$ (v/v=4:1, 30 mL) were added $Pd(PPh_3)_4$ (218 mg, 0.19 mmol) and $Na_2CO_3$ (795 mg, 7.5 mmol) under nitrogen. The reaction mixture was heated to 75° C. After stirring at 75° C. for 12 hr, the mixture was concentrated and treated with EtOAc. The organic phase was washed with water, brine, dried over anhydrous $Na_2SO_4$ and concentrated under reduced pressure to give the coupling product 1-(2-butoxyvinyl)-4-chloro-2-fluorobenzene which was purified by filtration through a pad of silica gel (Hex/EtOAc=20/1) to afford an oil (500 mg, 55%). The above 1-(2-butoxyvinyl)-4-chloro-2-fluorobenzene (200 mg, 0.88 mmol) was dissolved in a mixture of acetone (2 mL) and 3N aqueous HCl (2 mL). The mixture was heated at 40° C. under nitrogen for 5 hours, cooled to room temperature and extracted with ether. The organic phase was washed with brine, dried over anhydrous $Na_2SO_4$, and concentrated to afford the title compound which was used in the next step without further purification (185 mg). $^1$H NMR (400 MHz, $CDCl_3$) δ 9.76 (s, 1H), 7.16-7.14 (m, 3H), 3.74 (s, 2H).

Step 2. (R*)-N-(1-(4-chloro-2-fluorophenethyl)-3,3-difluoropiperidin-4-yl)-1H-pyrazolo-[3,4-d]pyrimidin-4-amine

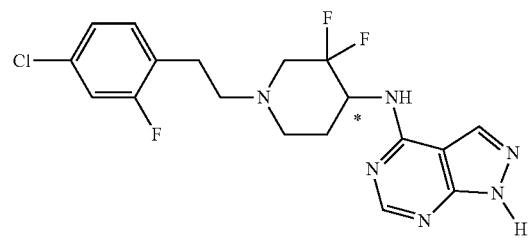 [SMILES: Fc1cc(Cl)ccc1CCN1CCC(Nc2ncnc3[nH]ncc23)C(F)(F)C1]

To a stirred solution of 2-(4-chloro-2-fluorophenyl)acetaldehyde (160 mg) and (R*)-N-(3,3-difluoropiperidin-4-yl)-1H-pyrazolo[3,4-d]pyrimidin-4-amine dihydrochloride (189 mg, 0.6 mmol) in MeOH (3 mL) were added TEA (175 mg, 1.73 mol) and 2 drops of AcOH. The mixture was stirred at room temperature for 30 min, followed by addition of $NaBH_3CN$ (74 mg, 1.1 mmol). The mixture was stirred for an additional 15 min, concentrated and taken up in EtOAc. The resulting suspension was filtered, and the filtrate was concentrated under reduced pressure. The residue was purified by column chromatography over silica gel (DCM/MeOH=25/1) to afford the title compound as a yellow solid (185 mg, 74%) 98% ee. (Column: CHIRALPAKAD-H4.6*150 mm, 5 um; Mobile Phase: A: Hexanes/B: Ethanol=70:30; t=3.57). MS (ESI) calcd for $C_{18}H_{18}ClF_3N_6$: 410.1, 312.1; found: 411.2, 413.2 [M+H]. $^1$H NMR (400 MHz, $CD_3OD$) δ 8.28 (s, 1H), 8.26 (s, 1H), 7.33 (t, J=8.0 Hz, 1H), 7.18-7.14 (m, 2H), 4.97-4.83 (m, 1H), 3.37-3.30 (m, 1H), 3.11-3.08 (m, 1H), 2.91-2.87 (m, 2H), 2.80-2.68 (m, 2H), 2.62-2.52 (m, 1H), 2.45-2.36 (m, 1H), 2.07-1.92 (m, 2H).

Example 1.20a. (R*)-N-(1-(4-chloro-2-fluorophenethyl)-3,3-difluoropiperidin-4-yl)-1H-pyrazolo-[3,4-d]pyrimidin-4-amine hydrochloride (E1-1.16a)

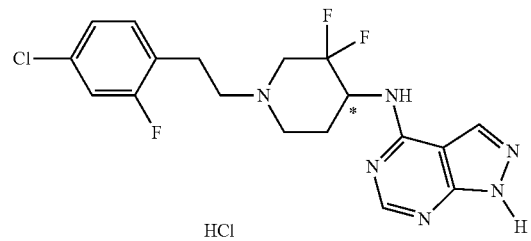 [SMILES: Fc1cc(Cl)ccc1CCN1CCC(Nc2ncnc3[nH]ncc23)C(F)(F)C1 ; Cl]

To a solution of (R*)-N-(1-(4-chloro-2-fluorophenethyl)-3,3-difluoropiperidin-4-yl)-1H-pyrazolo[3,4-d]pyrimidin-4-amine (164 mg, 0.4 mmol) in MeOH (3 mL) was added HCl in MeOH (0.2 mL, 2.0 N, 0.4 mmol) at rt. After stirring for 10 min, the mixture was concentrated to afford the title compound as a white solid (175 mg, 98%). MS (ESI) calcd for $C_{18}H_{18}ClF_3N_6$: 410.1, 412.1; found: 411.2, 413.2 [M+H]. $^1$H NMR (400 MHz, CD$_3$OD) δ 8.64 (s, 1H), 8.57 (s, 1H), 7.42 (t, J=8.0 Hz, 1H), 7.28-7.23 (m, 2H), 5.47-5.37 (m, 1H), 4.17-4.09 (m, 1H), 3.79-3.75 (m, 1H), 3.70-3.60 (m, 1H), 3.42-3.36 (m, 2H), 3.35-3.26 (m, 1H), 3.22-3.13 (m, 2H), 2.43-2.27 (m, 2H).

Example 1.21. (S*)-N-(1-(4-chloro-2-fluorophenethyl)-3,3-difluoropiperidin-4-yl)-1H-pyrazolo-[3,4-d]pyrimidin-4-amine (E2-1.16)

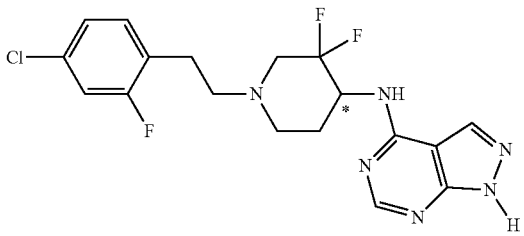 [SMILES: Fc1cc(Cl)ccc1CCN1CCC(Nc2ncnc3[nH]ncc23)C(F)(F)C1]

To a stirred solution of 2-(4-chloro-2-fluorophenyl)acetaldehyde (210 mg, 1.22 mmol) and (S*)-N-(3,3-difluoropiperidin-4-yl)-1H-pyrazolo[3,4-d]pyrimidin-4-amine hydrochloride (200 mg, 0.61 mmol) in MeOH (4 mL) were added TEA (185 mg, 1.8 mol) and 2 drops of AcOH. The mixture was stirred at ambient temperature for 30 min, followed by addition of NaBH$_3$CN (80 mg, 1.2 mmol). The mixture was stirred for additional 15 min. concentrated and taken up in EtOAc. The resulting suspension was filtered, and the filtrate was concentrated under reduced pressure. The residue was purified by column chromatography over silica gel (DCM/MeOH=25/1) to afford the title compound as a yellow solid (137 mg, 55%) 98% ee. (Column: CHIRALPAKAD-H4.6*150 mm, 5 um; Mobile Phase: A: Hexanes/B: Ethanol=70:30; t=4.48). MS (ESI) calcd for $C_{18}H_{18}ClF_3N_6$: 410.1, 412.1; found: 411.2, 413.2 [M+H]. $^1$H NMR (400 MHz, DMSO-d6) δ 13.46 (s, 1H), 8.30 (s, 1H), 8.28 (s, 1H), 8.24 (s, 1H), 8.24 (s, 1H), 7.41 (t, J=8.4 Hz, 1H), 7.37 (dd, J=8.0 and 2.0 Hz, 1H), 7.23 (dd, J=8.0 and 2.0 Hz, 1H), 4.93-4.81 (m, 1H), 3.32-3.22 (m, 1H), 3.00-2.97 (m, 1H), 2.81-2.78 (m, 2H), 2.67-2.53 (m, 3H), 2.45-2.36 (m, 1H), 1.92-1.70 (m, 2H). $^1$H NMR (400 MHz, DMSO-d6) δ 13.46 (s, 1H), 8.30 (s, 1H), 8.28 (s, 1H), 8.24 (s, 1H), 8.24 (s, 1H), 7.41 (t, J=8.4 Hz, 1H), 7.37 (dd, J=8.0 and 2.0 Hz, 1H), 7.23 (dd, J=8.0 and 2.0 Hz, 1H), 4.93-4.81 (m, 1H), 3.32-3.22 (m, 1H), 3.00-2.97 (m, 1H), 2.81-2.78 (m, 2H), 2.67-2.53 (m, 3H), 2.

Example 1.22. (±)-N-(3,3-difluoro-1-(2-(6-(trifluoromethyl)pyridin-3-yl)ethyl)piperidin-4-yl)-7H-pyrrolo[2,3-d]pyrimidin-4-amine (C-4.5)

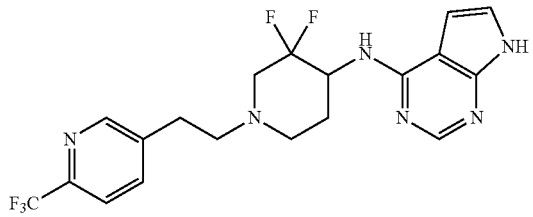 [SMILES: FC(F)(F)c1ccc(CCN2CCC(Nc3ncnc4[nH]ccc34)C(F)(F)C2)cn1]

To a stirred solution of 2-(6-(trifluoromethyl)pyridin-3-yl)acetaldehyde (102 mg, 0.54 mmol) and N-(3,3-difluoropiperidin-4-yl)-7-tosyl-7H-pyrrolo[2,3-d]pyrimidin-4-amine (200 mg, 0.491 mmol) in MeOH (4 mL) were added 2 drops of acetic acid. The mixture was stirred for 30 min at room temperature, and then NaBH$_3$CN (93 mg, 1.47 mmol) was added. After stirring for additional 15 min at room temperature, the reaction mixture was concentrated. The concentrate was diluted with ethyl acetate, washed with water, brine, dried Na$_2$SO$_4$, and concentrated. The residue was purified by column chromatography over silica gel (dichloromethane/methanol=50/1) to afford the Ts-protected intermediate, N-(3,3-difluoro-1-(2-(6-(trifluoromethyl)-pyridin-3-ypethyl)piperidin-4-yl)-7-tosyl-7H-pyrrolo[2,3-d]-pyrimidin-4-amine, as a yellow solid (210 mg, 0.36 mmol, 67%). The solid was dissolved in THF (3 mL) and 50% aqueous sodium hydroxide (3 mL) was added. The resulting mixture was stirred at 60° C. for 3 hours, and then cooled down to room temperature. The mixture was neutralized with 1 N aqueous HCl, and extracted with ethyl acetate. The combined organic phases were washed with brine, dried over Na$_2$SO$_4$ and concentrated. The residue was purified by column chromatography over silica gel (dichloromethane/MeOH=25/1) to afford the title compound as a yellow solid (120 mg, 81%). MS (ESI) calcd for $C_{18}H_{18}F_5N_6$:426.2; found: 427.2 [M+H]. $^1$H NMR (400 MHz, CD$_3$OD) δ 8.66 (d, J=1.2 Hz, 1H), 8.13 (s, 1H), 7.97 (dd, J=1.2, 8.0 Hz, 1H), 7.76 (d, J=8.0 Hz, 1H), 7.11 (d, J=3.6 Hz, 1H), 6.72 (d, J=3.6 Hz, 1H), 4.86-4.73 (m, 1H), 3.40-3.34 (m, 1H), 3.09-3.06 (m, 1H), 3.01-2.97 (m, 2H), 2.85-2.78 (m, 2H), 2.62-2.50 (m, 1H), 2.46-2.39 (m, 1H), 2.05-1.93 (m, 2H).

Example 1.22a. (±)-N-(3,3-difluoro-1-(2-(6-(trifluoromethyl)pyridin-3-yl)ethyl)-piperidin-4-yl)-7H-pyrrolo[2,3-d]pyrimidin-4-amine hydrochloride (C-4.5a)

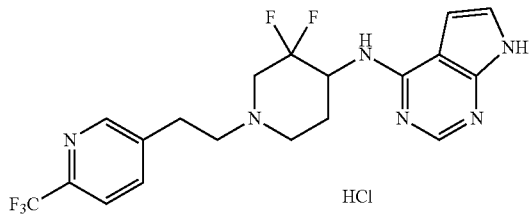 [SMILES: FC(F)(F)c1ccc(CCN2CCC(Nc3ncnc4[nH]ccc34)C(F)(F)C2)cn1 ; Cl]

To a stirred solution of N-(3,3-difluoro-1-(2-(6-(trifluoromethyl)pyridin-3-yl)-ethyl)piperidin-4-yl)-7H-pyrrolo[2, 3-d]pyrimidin-4-amine (120 mg, 0.282 mmol) in MeOH (2.3 mL) was added HCl in MeOH (0.14 mL, 2.0 M, 0.28 mmol) at rt. After stirring for 10 min, the mixture was concentrated to afford the title compound as a white solid (125 mg, 96%). MS (ESI) calcd for $C_{18}H_{18}F_5N_6$:426.2; found: 427.2 [M+H]. $^1$H NMR (400 MHz, CD$_3$OD) δ 8.60 (s, 1H), 8.31 (s, 1H), 7.93 (d, J=8.0 Hz, 1H), 7.70 (d, J=8.0 Hz, 1H), 7.30 (d, J=3.6 Hz, 1H), 6.94 (d, J=3.6 Hz, 1H), 5.03-4.85 (m, 1H), 3.83 (brs, 1H), 3.57-3.46 (m, 1H), 3.38-3.29 (m, 2H), 3.13-2.91 (m, 3H), 2.30-2.20 (m, 2H), 0.85-0.70 (m, 1H).

Example 1.23. (R*)-N-(3,3-difluoro-1-(4-(trifluoromethoxy)phenethyl)piperidin-4-yl)-1H-pyrazolo[3,4-d]pyrimidin-4-amine (E1-1.11)

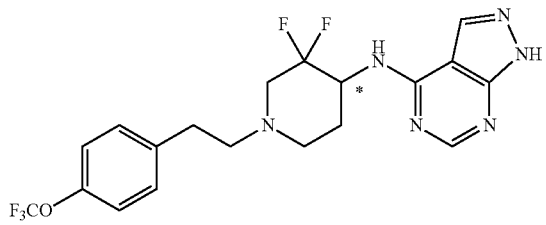 [SMILES: FC(F)(F)Oc1ccc(CCN2CCC(Nc3ncnc4[nH]ncc34)C(F)(F)C2)cc1]

Step 1. 2-(4-(trifluoromethoxy)phenyl)ethanol

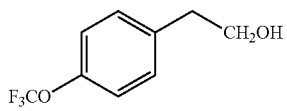 [SMILES: OCCc1ccc(OC(F)(F)F)cc1]

To a stirred suspension of lithium aluminumhyride (390 mg, 10.26 mmol) in dry THF (30 mL) was added a solution of 2-(4-(trifluoromethoxy)phenyl)acetic acid (1.5 g, 6.80 mmol) dropwise in dry THF at 0° C. under nitrogen atmosphere. The resulting mixture was stirred at room temperature for 3 hours. The mixture was carefully quenched by addition of water at 0° C. The white suspension was filtered through a pad of celite, and the filter mass was extracted with ethyl acetate. The combined organic phases were washed with brine, dried over Na$_2$SO$_4$, and concentrated. The resulting light brown oil (1.4 g) was directly used in the next step without further purification. $^1$H NMR (400 MHz, CDCl$_3$) δ 7.26 (d, J=8.0 Hz, 2H), 7.16 (d, J=8.0 Hz, 2H), 3.87 (t, J=6.4 Hz, 2H), 2.88 (t, J=6.4 Hz, 2H).

Step 2. 2-(4-(trifluoromethoxy)phenyl)acetaldehyde

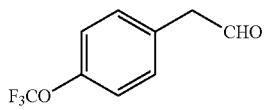

To a stirred solution of 2-(4-(trifluoromethoxy)phenyl) ethanol (380 mg, 1.84 mmol) in acetonitrile (9 mL) was added 2-iodoxybenzoic acid (1.0 g, 3.7 mmol). The resulting suspension was heated to reflux, and stirred for 1 hour under reflux. The suspension was allowed to cool to room temperature, filtered and concentrated to afford the title compound as a pale brown oil (376 mg, 100%) which was used in the next step without further purification. $^1$H NMR (400 MHz, CDCl$_3$) δ 9.77 (t, J=2.0 Hz, 1H), 7.25-7.20 (m, 4H), 3.73 (d, J=2.0 Hz, 2H).

Step 3. (R*)-N-(3,3-difluoro-1-(4-(trifluoromethoxy)phenethyl)piperidin-4-yl)-1-tosyl-1H-pyrazolo[3,4-d]pyrimidin-4-amine

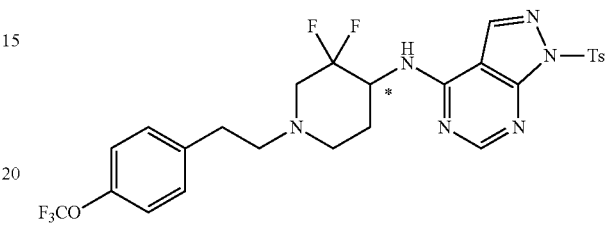

To a stirred solution of 2-(4-(trifluoromethoxy)phenyl) acetaldehyde (372 mg, 1.84 mmol) in methanol (9 mL) was added (R*)-N-(3,3-difluoropiperidin-4-yl)-1-tosyl-1H-pyrazolo[3,4-d]-pyrimidin-4-amine (376 mg, 0.92 mmol). The resulting solution was stirred at ambient temperature for 10 min. Subsequently, NaBH$_3$CN (63 mg, 1.84 mmol) was added to the reaction mixture. After stirring for 1 h, the mixture was concentrated. The residue was partitioned into aqueous NaHCO$_3$ and dichloromethane. The organic phase was washed with brine, dried over Na$_2$SO$_4$, and concentrated. The residue was purified by column chromatography over silica gel (eluent: hexane/EtOAc=2/1) to afford the title compound as a pale yellow solid (203 mg, 37%). MS (ESI) calcd for $C_{26}H_{25}F_5N_6O_3S$: 596.2; found: 597.2 [M+H]. $^1$H NMR (400 MHz, CDCl$_3$) δ 8.58 (s, 1H), 8.11 (s, 1H), 8.07 (d, J=8.0 Hz, 2H), 7.30 (d, J=8.0 Hz, 2H), 7.22 (d, J=8.0 Hz, 2H), 7.14 (d, J=8.0 Hz, 2H), 5.56 (brs, 1H), 4.90-4.70 (m, 1H), 3.36-3.26 (m, 1H), 3.07-2.99 (m, 1H), 2.85-2.76 (m, 2H), 2.75-2.65 (m, 2H), 2.54-2.41 (m, 1H), 2.39 (s, 3H), 2.38-2.30 (m, 1H), 2.17-2.10 (m, 1H), 1.86-1.74 (m, 1H).

Step 4. (R*)-N-(3,3-difluoro-1-(4-(trifluoromethoxy)phenethyl)piperidin-4-yl)-1H-pyrazolo[3,4-d]pyrimidin-4-amine

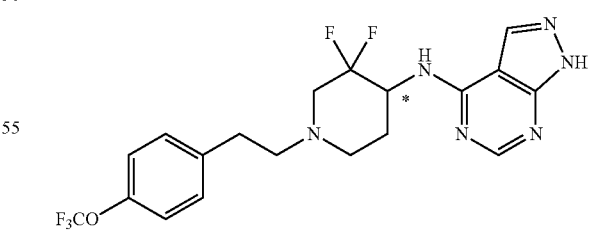

To a stirred solution of (R*)-N-(3,3-difluoropiperidin-4-yl)-1-tosyl-1H-pyrazolo[3,4-d]-pyrimidin-4-amine (203 mg, 0.34 mmol) in DCM/MeOH (1 mL/1 mL) was added HCl/ether (1 mL, 1.0M). After stirring overnight, the mixture was concentrated. The residue was suspended in water, basified with aqueous NaOH (1.0 M), and extracted with EtOAc. The combined organic phases were washed with brine, dried over Na$_2$SO$_4$, and concentrated. The residue was purified by column chromatography over silica gel (eluent: hexane/EtOAc=1/1) to afford the title compound as an off-white powder (54 mg, 37%). MS (ESI) calcd for C$_{19}$H$_{19}$F$_5$N$_6$O: 442.2; found: 443.0 [M+H]. $^1$H NMR (400 MHz, CDCl$_3$) δ 12.20 (brs, 1H), 8.48 (s, 1H), 8.04 (s, 1H), 7.24 (d, J=8.0 Hz, 2H), 7.15 (d, J=8.0 Hz, 2H), 5.68-5.56 (m, 1H), 4.98-4.75 (m, 1H), 3.40-3.30 (m, 1H), 3.12-3.04 (m, 1H), 2.88-2.64 (m, 4H), 2.58-2.48 (m, 1H), 2.46-2.36 (m, 1H), 2.24-2.14 (m, 1H), 1.92-1.80 (m, 1H).

Example 1.23a. (R*)-N-(3,3-difluoro-1-(4-(trifluoromethoxy)phenethyl)piperidin-4-yl)-1H-pyrazolo[3,4-d]-pyrimidin-4-amine hydrochloride (E1-1.11a)

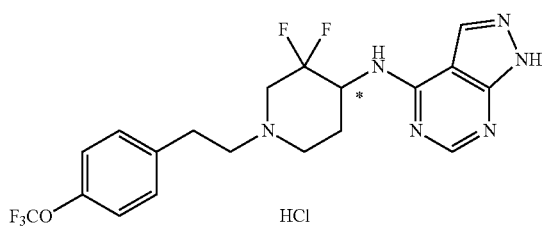 [SMILES: FC(F)(F)Oc1ccc(CCN2CCC(Nc3ncnc4[nH]ncc34)C(F)(F)C2)cc1 ; Cl]

To a solution of (R*)-N-(3,3-difluoro-1-(4-(trifluoromethoxy)phenethyl)piperidin-4-yl)-1H-pyrazolo[3,4-d]-pyrimidin-4-amine (54 mg, 0.12 mmol) in DCM/MeOH (0.5 mL/0.5 mL) was added HCl in methanol (0.12 mL, 1.0M, 0.12 mmol). After stirring for 30 min, the solution was concentrated to afford the title compound as an off-white powder (55 mg, 98%). MS (ESI) calcd for C$_{119}$H$_{19}$F$_5$N$_6$O: 442.2; found: 443.2 [M+H]. $^1$H NMR (400 MHz, CD$_3$OD) δ 8.32 (brs, 2H), 7.32 (d, J=8.0 Hz, 2H), 7.16 (d, J=8.0 Hz, 2H), 5.27-2.13 (m, 1H), 3.92-3.84 (m, 1H), 3.58-3.52 (m, 1H), 3.45-3.28 (m, 1H), 3.12-2.94 (m, 4H), 2.28-2.06 (m, 2H), 1.26-1.18 (m, 2H).

Example 1.24. (R*)-N-(1-(4-(difluoromethoxy)phenethyl)-3,3-difluoropiperidin-4-yl)-1H-pyrazolo[3,4-d]pyrimidin-4-amine (E1-1.12)

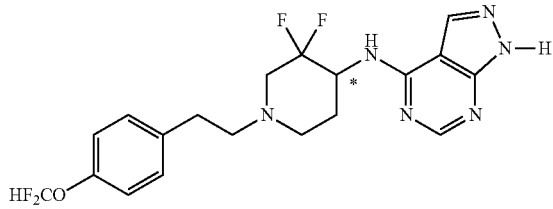

Step 1. 1-(difluoromethoxy)-4-(2-methoxyvinyl)benzene

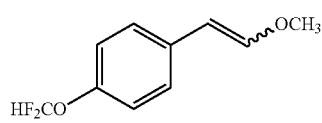

To a stirred solution of (methoxymethyl)triphenylphosphonium chloride (6.69 g, 19.5 mmol) in dry THF (200 mL) was added n-BuLi (2.5 M in hexane, 7.2 mL, 18 mmol) at −20° C. After stirring for 15 min at −20° C. 4-(difluoromethoxy)benzaldehyde (2.6 g, 15 mmol) in dry THF (50 mL) was added dropwise, and the mixture was gradually warmed to room temperature. The mixture was stirred overnight at room temperature, and quenched with sat.NH$_4$Cl. The mixture was extracted with ethyl acetate. The organic layer was washed with water, brine, dried with Na$_2$SO$_4$ and concentrated in vacuo. The residue was purified by column chromatography over silica gel (ethyl acetate/hexane=1/10) to afford the title compound as a colorless oil which was comprised of a ca. 2:1 of E to Z isomers (1.8 g, 60%) by $^1$H NMR analysis. $^1$H NMR (400 MHz, CDCl$_3$) E-isomer δ 7.20 (d, J=8.8 Hz, 2H), 7.01 (d, J=8.8 Hz, 2H), 6.99 (d, J=12.8 Hz, 1H), 6.46 (t, J=74.0 Hz, 1H), 5.78 (d, J=12.8 Hz, 1H), 3.68 (s, 3H). Z-isomer δ 7.55 (d, J=8.8 Hz, 2H), 7.04 (d, J=8.8 Hz, 2H), 6.47 (t, J=74.0 Hz, 1H), 6.13 (d, J=6.8 Hz, 1H), 5.19 (d, J=6.8 Hz, 1H), 3.78 (s, 3H).

Step 2. 2-(4-(difluoromethoxy)phenyl)acetaldehyde

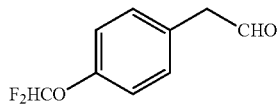

A stirred solution of 1-(difluoromethoxy)-4-(2-methoxyvinyl)benzene (500 mg, 2.5 mmol) in acetone (5 mL) and aqueous HCl (3 mL, 3.0 M) was heated to 50° C. under nitrogen. After stirring for 3 hr, the mixture was cooled to room temperature and extracted with ether. The organic phase was washed with brine, dried over anhydrous Na$_2$SO$_4$, and concentrated to afford the title compound as a colorless oil (360 mg, 78%) which was directly used into the next step without further purification. $^1$H NMR (400 MHz, CDCl$_3$) δ 9.75 (t, J=2.0 Hz, 1H), 7.21 (d, J=8.8 Hz, 2H), 7.13 (d, J=8.8 Hz, 2H), 6.51 (t, J=73.6 Hz, 1H), 3.70 (d, J=2.0 Hz, 2H).

Step 3. (R*)-N-(1-(4-(difluoromethoxy)phenethyl)-3,3-difluoropiperidin-4-yl)-1-tosyl-1H-pyrazolo[3,4-d]pyrimidin-4-amine

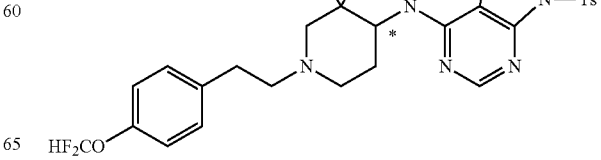

To a stirred solution of the above 2-(4-(difluoromethoxy)phenyl)acetaldehyde (360 mg) and (R*)-N-(3,3-difluoropiperidin-4-yl)-1-tosyl-1H-pyrazolo[3,4-d]pyrimidin-4-amine (410 mg, 1.0 mmol) in MeOH (10 mL) was added catalytic amount of AcOH. The mixture was stirred at room temperature for 30 min, followed by addition of NaBH$_3$CN (130 mg, 2.0 mmol), and stirred for additional 15 min. The mixture was concentrated, and dissolved in ethyl acetate. The organic layer was washed with brine, dried with Na$_2$SO$_4$ and concentrated in vacuo. The residue was purified by column chromatography over silica gel (DCM/MeOH=50/1) to afford the title product as a white solid (200 mg, 35%). $^1$H NMR (400 MHz, CDCl$_3$) δ 8.58 (s, 1H), 8.13 (s, 1H), 8.07 (d, J=8.4 Hz, 2H), 7.31 (d, J=8.4 Hz, 2H), 7.19 (d, J=8.4 Hz, 2H), 7.05 (d, J=8.4 Hz, 2H), 6.48 (t, J=74.0 Hz, 1H), 5.65-5.63 (m, 1H), 4.88-4.71 (m, 1H), 3.35-3.28 (m, 1H), 3.04-3.01 (m, 1H), 2.81-2.76 (m, 2H), 2.74-2.66 (m, 2H), 2.52-2.42 (m, 1H), 2.39 (s, 3H), 2.39-2.31 (m, 1H), 2.15-2.09 (m, 1H), 1.86-1.76 (m, 1H).

Step 4. (R*)-N-(1-(4-(difluoromethoxy)phenethyl)-3,3-difluoropiperidin-4-yl)-1H-pyrazolo[3,4-d]pyrimidin-4-amine

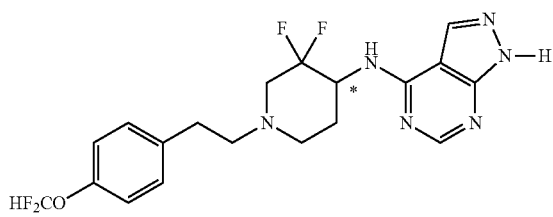

To a stirred solution of (R*)-N-(1-(4-(difluoromethoxy)phenethyl)-3,3-difluoropiperidin-4-yl)-1-tosyl-1H-pyrazolo[3,4-d]pyrimidin-4-amine (200 mg, 0.346 mmol) in methanol (2 mL) was added HCl in ether (2 mL, 1.0 M) at room temperature. After stirring for 2 hr, the white suspension was concentrated to dryness. The residue was dissolved in water, and basified with aqueous NaOH (1.0 M). The aqueous phase was extracted with EtOAc. The combined organic phases were washed with brine, dried over Na$_2$SO$_4$ and concentrated. The residue was purified by column chromatography over silica gel (DCM/MeOH=30/1) to afford the title compound as a white powder (85 mg, 53%). MS (ESI) calcd for C$_{19}$H$_{20}$F$_4$N$_6$O: 424.2; found: 425.3 [M+H]. $^1$H NMR (400 MHz, CD$_3$OD) δ 8.28 (s, 1H), 8.26 (s, 1H), 7.30 (d, J=8.4 Hz, 2H), 7.08 (d, J=8.4 Hz, 2H), 6.78 (t, J=74.4 Hz, 1H), 4.99-4.88 (m, 1H), 3.40-3.33 (m, 1H), 3.14-3.08 (m, 1H), 2.88-2.82 (m, 2H), 2.78-2.74 (m, 2H), 2.62-2.52 (m, 1H), 2.46-2.39 (m, 1H), 2.07-1.93 (m, 2H).

Example 1.24a. (R*)-N-(1-(4-(difluoromethoxy)phenethyl)-3,3-difluoropiperidin-4-yl)-1H-pyrazolo[3,4-d]pyrimidin-4-amine hydrochloride (E1-1.12a)

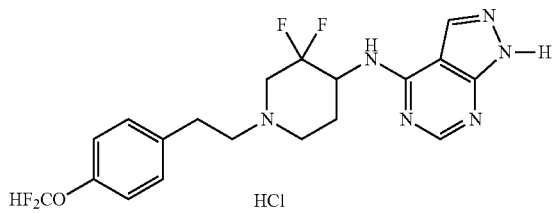

To a stirred solution of (R*)-N-(1-(4-(difluoromethoxy)phenethyl)-3,3-difluoropiperidin-4-yl)-1H-pyrazolo[3,4-d]pyrimidin-4-amine (85 mg, 0.2 mmol) in MeOH (3 mL) was added HCl in methanol (2.0 M, 0.1 mL). The reaction solution was stirred at room temperature for 15 min. The solvent was evaporated to afford the title compound as a white powder (91 mg, 99%). MS (ESI) calcd for C$_{19}$H$_{20}$F$_4$N$_6$O: 424.2; found: 425.3 [M+H]. $^1$H NMR (400 MHz, CD$_3$OD) δ 8.72 (s, 1H), 8.63 (s, 1H), 7.40 (d, J=8.4 Hz, 2H), 7.16 (d, J=8.4 Hz, 2H), 6.83 (t, J=74.0 Hz, 1H), 5.60-5.48 (m, 1H), 4.30-4.22 (m, 1H), 3.93-3.79 (m, 2H), 3.57-3.45 (m, 3H), 3.22-3.14 (m, 2H), 2.51-2.36 (m, 2H).

Example 2. Activity

Example 2.1. NR2B Antagonist Activity

HEK293 cell lines stably expressing cloned human NR1/NR2B and NR1/NR2A, respectively, were established according to standard previously described methods (Hansen et al., *Comb. Chem High Throughput Screen.* 11:304, 2008). Activation of the NR2A or NR2B subtype of NMDA receptor with glutamate as an agonist and glycine co-agonist on these cells results in calcium influx, which can be monitored with fluorescent indicator Fluo-4. A cell based assay has been implemented to evaluate the effect of a compound on NR2A and NR2B receptors by measuring the fluorescent changes (Hansen et al., *Comb. Chem High Throughput Screen.* 11:304, 2008).

HEK293 cells stably expressing NR2A or NR2B receptors were cultured at 37° C. in a humidified CO$_2$ incubator in DMEM supplemented with 10% fetal bovine serum (FBS) (Hyclone), 10 μM MK801 (Sigma-Aldrich) and 50 μM AP-5 (Tocris). For experiments, the cells were seeded onto poly-D-lysine-coated 96-well black plates with clear bottom (Corning) at a density of ~50,000 cells/well. After overnight culture, the growth medium was removed from the wells and the cells were incubated at 37° C. for 60 min in Hanks buffer containing 4 μM fluo-4-AM (Invitrogen) and 0.1% bovine serum albumin (BSA). After dye-loading, the cells were washed three times with Hanks buffer and incubated for 10 min at room temperature with various concentrations of test compounds prepared in Hanks buffer with 0.1% BSA. The cell plates were placed onto FDSS μCell fluorescence reader (Hamamatsu). After 20 sec reading of background fluorescence, agonist glutamate at final 100 μM and co-agonist glycine at final 50 μM were added to the cells to activate the receptor, and the resulting fluorescence changes were recorded and quantified. Based on the changes in fluorescence intensity, the pharmacological effect of test compounds were analyzed and the IC$_{50}$ values derived from a non-linear least squares fitting of the concentration-dependent response to a standard logistic equation using Prism (Graphpad, Inc):

Amplitude=Max Amplitude/(1+(IC50/[antagonist])$^n$).

Results are shown in Table 2.1.

TABLE 2.1

| Cmpd. No. | Free Base Structure | hNR2B IC$_{50}$ (nM) | hNR2A IC$_{50}$ |
|---|---|---|---|
| E1-1.5 | | 32.9 | >10 μM |
| E2-1.5 | | 37.8 | >10 μM |
| C-1.1 | | 98.8 | >10 μM |
| C-2.5 | | 105 | >10 μM |
| C-1.33 | | 103 | >10 μM |
| C-3.5 | | 822 | >10 μM |

TABLE 2.1-continued

| Cmpd. No. | Free Base Structure | hNR2B IC$_{50}$ (nM) | hNR2A IC$_{50}$ |
|---|---|---|---|
| C-3.4 | | 2270 | >10 μM |
| E1-1.3 | | 25.0 | >10 μM |
| E2-1.3 | | 31.7 | >10 μM |
| C-1.2 | | 68.3 | >10 μM |
| E1-1.4 | | 18.5 | >10 μM |
| E2-1.4 | | 21.9 | >10 μM |

TABLE 2.1-continued

| Cmpd. No. | Free Base Structure | hNR2B IC$_{50}$ (nM) | hNR2A IC$_{50}$ |
|---|---|---|---|
| C-1.15 | 2,4-difluorophenethyl-(3,3-difluoropiperidin-4-yl)-NH-pyrazolo[3,4-d]pyrimidine | 78.9 | >10 μM |
| C-1.34 | 4-trifluoromethylphenethyl-(3,3-difluoropiperidin-4-yl)-NH-3-methyl-pyrazolo[3,4-d]pyrimidine | 72.8 | >10 μM |
| C-4.5 | 6-(trifluoromethyl)pyridin-3-yl-ethyl-(3,3-difluoropiperidin-4-yl)-NH-pyrrolo[2,3-d]pyrimidine | 1740 | >10 μM |
| C-1.35 | 2,5-difluorophenethyl-(3,3-difluoropiperidin-4-yl)-NH-pyrazolo[3,4-d]pyrimidine | 329 | >10 μM |
| C-1.36 | 3-trifluoromethylphenethyl-(3,3-difluoropiperidin-4-yl)-NH-pyrazolo[3,4-d]pyrimidine | 291 | >10 μM |
| E1-1.6 | 4-(difluoromethyl)phenethyl-(3,3-difluoropiperidin-4-yl)*-NH-pyrazolo[3,4-d]pyrimidine | 21.2 | >10 μM |

TABLE 2.1-continued

| Cmpd. No. | Free Base Structure | hNR2B IC$_{50}$ (nM) | hNR2A IC$_{50}$ |
|---|---|---|---|
| E2-1.6 | HF$_2$C-phenyl-CH$_2$CH$_2$-N(piperidine-3,3-F$_2$)-4-NH-pyrazolo[3,4-d]pyrimidine | 17.0 | >10 μM |
| E1-1.7 | FH$_2$C-phenyl-CH$_2$CH$_2$-N(piperidine-3,3-F$_2$)-4-NH-pyrazolo[3,4-d]pyrimidine | 22.4 | >10 μM |
| E2-1.7 | FH$_2$C-phenyl-CH$_2$CH$_2$-N(piperidine-3,3-F$_2$)-4-NH-pyrazolo[3,4-d]pyrimidine | 38.1 | >10 μM |
| E1-1.16 | 4-Cl-2-F-phenyl-CH$_2$CH$_2$-N(piperidine-3,3-F$_2$)-4-NH-pyrazolo[3,4-d]pyrimidine | 27.9 | >10 μM |
| E2-1.16 | 4-Cl-2-F-phenyl-CH$_2$CH$_2$-N(piperidine-3,3-F$_2$)-4-NH-pyrazolo[3,4-d]pyrimidine | 61.9 | >10 μM |
| E1-1.11 | F$_3$CO-phenyl-CH$_2$CH$_2$-N(piperidine-3,3-F$_2$)-4-NH-pyrazolo[3,4-d]pyrimidine | 68.4 | >10 μM |

TABLE 2.1-continued

| Cmpd. No. | Free Base Structure | hNR2B IC$_{50}$ (nM) | hNR2A IC$_{50}$ |
|---|---|---|---|
| E1-1.12 | 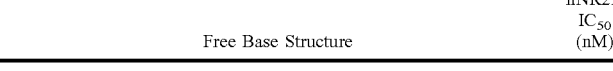 | 83.8 | >10 μM |

Example 2.2. hERG Channel Inhibition

The assay was performed on hERG channel stably expressed in HEK293 cells. The cells were cultured at 37° C. in a humidified CO$_2$ incubator in the growth medium consisting of DMEM, 10% fetal bovine serum and antibiotics. Prior to the assay, the cells were seeded onto a 12 mm PDL-coated glass coverslip and cultured in a 35 mm Petri dish. After 16 to 40 hr culture, the cover slip was transferred into the chamber of OctaFlow perfusion system (ALA Instrument) and under a constant flow of extracellular solution (140 mM NaCl, 4 mM KCl, 1 mM MgCl$_2$, 2 mM CaCl$_2$, 10 mM HEPES, 10 mM D-glucose, pH 7.35, osmolarity 290). Whole cell patch clamping was performed with a glass micropipette filled with intracellular solution (120 mM KCl, 1.75 mM MgCl$_2$, 5.4 mM CaCl$_2$, 10 mM HEPES, 10 mM EGTA, and 4 mM ATP-K$_2$, PH 7.2, osmolarity 310). Giga-seal was maintained during the test. The voltage control and current measurement were carried out using Axon amplifier 700B, Digidata 1440A and CLAMPEX10 software (Molecular Devices). Whole-cell hERG currents were recorded following the Petroski protocol: the cell was held at −80 mV, and the voltage step jumped from −80 to 30 mV and stay for 2 sec with a 20 ms prepulse at −40 mV. After depolarization, the voltage was decreased to −40 mV and stay for 2 sec, and returned back to −80 mV. Test compound was applied by quartz capillary tubes tip (200 μm inner diameter), and the flow rate was controlled at 2-3 ml/min with OctaFlow perfusion system. Different concentrations of the compound were applied to the cells for 5 min and the hERG current was measured three times before, during and after compound treatment. The data were analyzed using Clampfit 10 software (Molecular Devices) to generate IC$_{50}$ values. Results are shown in Table 2.2.

TABLE 2.2

| Cmpd. No. | Free Base Structure | hNR2B IC$_{50}$ (nM) | hERG IC$_{50}$ (μM) | hERG @ 10 μM (%) |
|---|---|---|---|---|
| LX-1 | 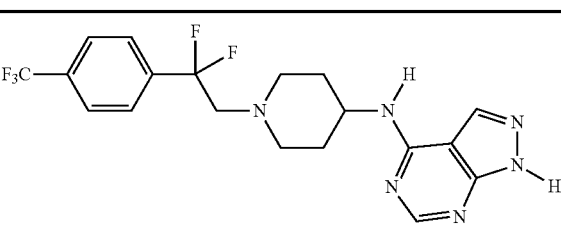 | 24 | 4.5 | 61 |
| E1-1.5 | 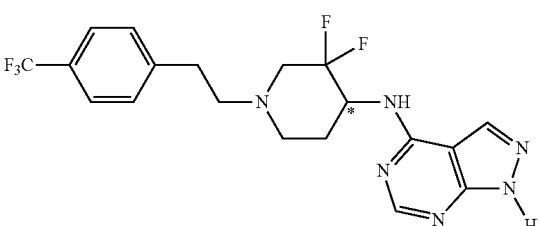 | 32.9 | 9.8 | |
| E2-1.5 | 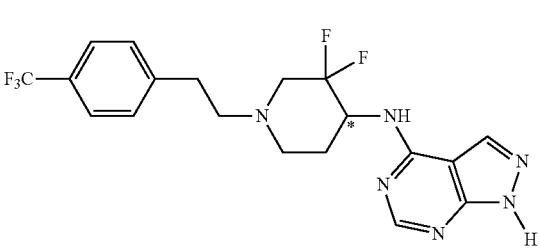 | 37.8 | 7.6 | |

TABLE 2.2-continued

| Cmpd. No. | Free Base Structure | hNR2B IC$_{50}$ (nM) | hERG IC$_{50}$ (μM) | hERG @ 10 μM (%) |
|---|---|---|---|---|
| C-1.1 | | 98.8 | 71 | |
| C-2.5 | | 105 | | 60 |
| C-1.33 | | 103 | | 59 |
| C-3.5 | | 822 | | 23 |
| C-3.4 | | 2270 | | 18 |
| E1-1.3 | | 25.0 | | 58 |

TABLE 2.2-continued

| Cmpd. No. | Free Base Structure | hNR2B IC$_{50}$ (nM) | hERG IC$_{50}$ (μM) | hERG @ 10 μM (%) |
|---|---|---|---|---|
| E2-1.3 | | 31.7 | | 64 |
| C-1.2 | | 68.3 | 16.3 | |
| E1-1.4 | | 18.5 | 21.9 | |
| E2-1.4 | | 21.9 | 15.5 | |
| C-1.15 | | 78.9 | | 37 |
| C-1.34 | | 72.8 | | 68 |

TABLE 2.2-continued

| Cmpd. No. | Free Base Structure | hNR2B IC$_{50}$ (nM) | hERG IC$_{50}$ (μM) | hERG @ 10 μM (%) |
|---|---|---|---|---|
| C-4.5 | | 1740 | | 24 |
| C-1.35 | | 329 | | 17 |
| C-1.36 | | 291 | | 56 |
| E1-1.6 | | 21.2 | 3.5 | 63 |
| E2-1.6 | | 17.0 | | 70 |
| E1-1.7 | | 22.4 | | 36 |

TABLE 2.2-continued

| Cmpd. No. | Free Base Structure | hNR2B IC$_{50}$ (nM) | hERG IC$_{50}$ (μM) | hERG @ 10 μM (%) |
|---|---|---|---|---|
| E2-1.7 | | 38.1 | | 49 |
| E1-1.16 | | 27.9 | | 47 |
| E2-1.16 | | 61.9 | | 64 |
| E1-1.11 | | 68.4 | | |
| E1-1.12 | | 83.8 | | 79 |

Example 2.3. CYP P450 Enzyme Inhibition

Inhibitory activities of test compounds on 5 major isoforms of CYP P450 were evaluated by using pooled human liver microsome (HLM, purchased from BD Gentest) and selective substrates for those isoforms. Those CYP isoforms and their corresponding probe substrates are as follows: CYP1A2 (phenacetin, 30 μM), CYP2C9 (tolutamide, 100 μM), CYP2C19 (S-mephenytoin, 40 μM), CYP2D6 (dextromethorphan, 5 μM) and CYP3A4 (midazolam, 1 μM). All probe substrates were used at concentrations near or below their K$_{ms}$. For experiment, a reaction mixture of test compound at 10 uM or in serial dilution, CYP probe substrate described above and 0.2 mg/mL pooled HLM in phosphate buffer, pH 7.4 in a final volume of 200 μL was pre-incubated at 37° C. for 10 minutes in triplicate. The reaction was initiated by addition of NADPH at final concentration of 1 mM. The reaction was terminated after 10 minutes (CYP1A2, CYP2D6 and CYP3A4) or 30 minutes (CYP2C9 and CYP2C19) by addition of 100 μL ice-cold acetonitrile with internal standard (IS). The samples were then centrifuged at 13,000 rpm and the supernatants were injected to LC-MS/MS (Agilent Technologies) to quantify the concentration of the specific metabolites of the probe substrates formed by individual CYP450 isoforms. The inhibition ratio is calculated as:

$(M_t - M_0)/M_{water} \times 100\%$ in which $M_t$ and $M_0$ represent the concentrations of the specific probe substrate metabolite, which was formed by individual CYP450 isoform, at the beginning and end of the reaction in the presence of test compound; while $M_{water}$ represents the concentration of the specific metabolite at the end of the reaction in the absence of test compound. Test compound concentration-dependent response data experiments performed in triplicate. Mean CYP2D6 $IC_{50}$ values were derived from non-linear, least-squares fitting of dose-dependent response data to a standard logistic equation (Prism, GraphPad Software, Inc) to generate the CYP2D6 $IC_{50}$ results shown in Table 2.3.

TABLE 2.3

| Cmpd. No. | Free Base Structure | hNR2B $IC_{50}$ (nM) | CYP2D6 $IC_{50}$ (μM) | CYP2D6 @ 10 μM (%) |
|---|---|---|---|---|
| LX-1 | 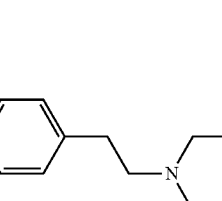 | 24 | 1.0 | 93 |
| E1-1.5 | 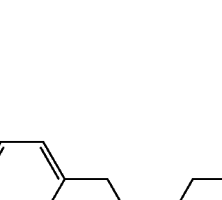 | 32.9 | 34.1 | 27.6 |
| E2-1.5 | 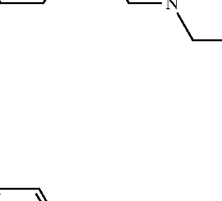 | 37.8 | 15.2 | 37.9 |
| E1-1.3 | 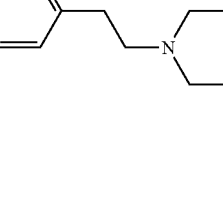 | 25.0 | | 21.5 |
| E2-1.3 | 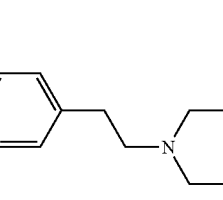 | 31.7 | | 27.6 |

TABLE 2.3-continued
| Cmpd. No. | Free Base Structure | hNR2B IC$_{50}$ (nM) | CYP2D6 IC$_{50}$ (μM) | CYP2D6 @ 10 μM (%) |
|---|---|---|---|---|
| C-1.2 | 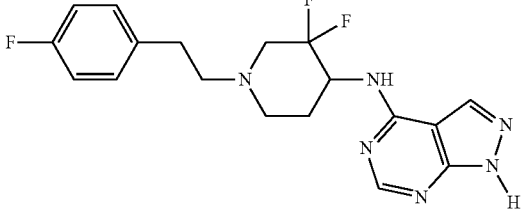 | 68.3 | | 45.1 |
| C-1.36 | 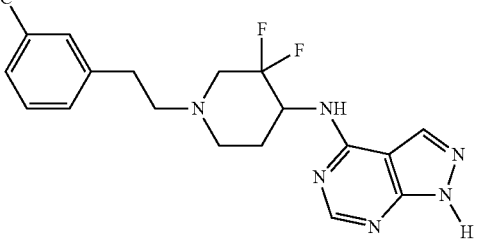 | 291 | | 27.9 |
| E1-1.6 | 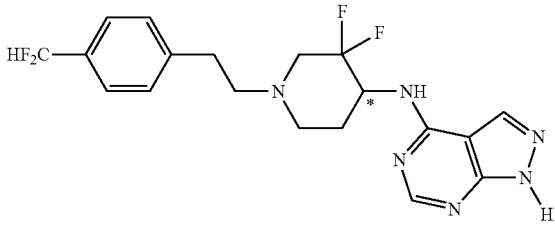 | 21.2 | | 24.4 |
| E2-1.6 | 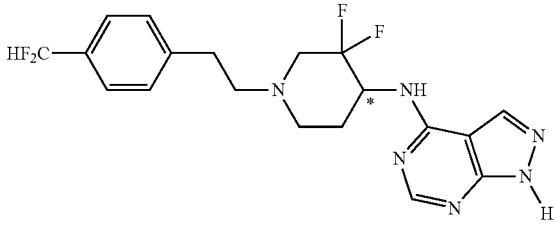 | 17.0 | | 37.1 |
| E1-1.7 | 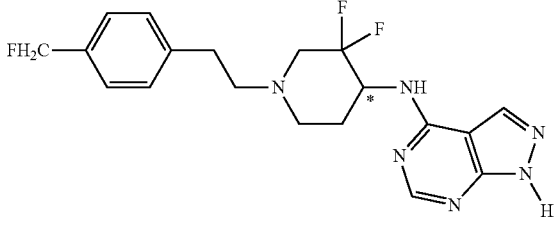 | 22.4 | | 23.2 |
| E1-1.16 | 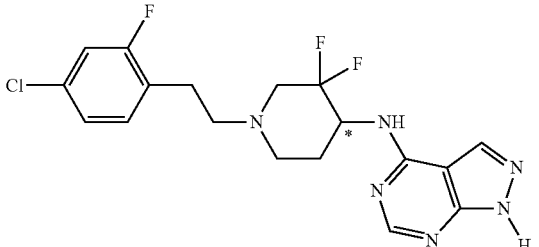 | 27.9 | | 23.2 |

Example 2.4. Forced Swim Test (FST)

The forced swim test was used to evaluate antidepressant activity (Porsolt et al., 1977 *Arch. Int. Pharmacodyn.* 229: 327-336). Mice that are forced to swim in a situation from which they cannot escape, rapidly become immobile. Drugs with antidepressant activity, such as imipramine, reduce the amount of time spent in the immobile state. Therefore, the amount of immobility time during a test conducted after drug administration represents a useful indicator of antidepressant activity (Lucki et el., 2001, *Psychopharmacology* 155:315-322).

Procedure. Male mice (strain NLMN) weighing 25-35 g were used for testing. All animals were housed in a temperature (22-24° C.) and humidity (50-60%) controlled environment with free access to food and water on a 12-hour light-dark cycle. Test compounds were dissolved in 0.5% dimethylsulfoxide, 4% hydroxypropyl-β-cyclodextrin water to generate the appropriate dosing solution. Drugs were administered by intraperitoneal injection at a dose volume of 10 mL/kg. Testing was initiated 20-60 minutes after dosing. Testing for antidepressant activity was conducted as described by Darci et al. (Darci et al., 2004, *Eur. J. Pharmacol.* 499:135-146). Mice were placed in a white plastic cylinder 20 cm high with a diameter of 21 cm containing 10 cm of water at 25±2° C. The mice were videotaped for 6 minutes, and the last 4 minutes of video were analyzed by a blinded observer off-line. The observer judged the animal to be immobile when it ceased all activity (struggling, swimming, jumping etc.) and floated passively atop the water. The amount of time each animal spent in the immobile state was recorded and used for statistical analysis of compound effect. Group differences were evaluated by student's t-test or one-way ANOVA followed by post-hoc Dunnett's test.

Results.

In Examples 2.4.1 and 2.4.2, the positive control compound, imipramine (32 mg/kg, IP) showed the expected antidepressant activity. These results indicate that provided compounds exhibit antidepressant activity when tested in a standard model for human depression.

Example 2.4.1. Compounds E1-1.5 and E2-1.5

Figure 1B:
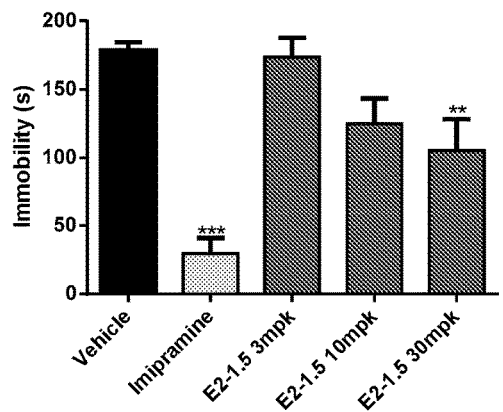

Results are shown in FIGS. 1A and 1B. Bars represent the mean±SEM immobility time for each dose group (n=10, \*\*\*/\*\*/\*: different from vehicle group, p<0.001/0.01/0.05 respectively, One-way ANOVA, Dunnett's post-test). Doses are given as milligram per kilogram (mpk). The dose of imipramine was 32 mpk.

Example 2.4.2. Compounds E1-1.3 and E2-1.3

Figure 2:
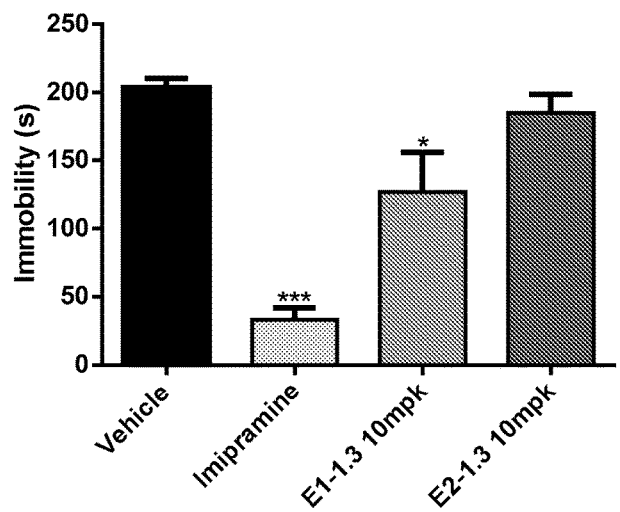
FIG. 2 shows results of the forced swim test as described in Example 2.4.2 with compounds E1-1.3 ((R*)-N-(1-(4-chlorophenethyl)-3,3-difluoropiperidin-4-yl)-1H-pyrazolo[3,4-d]pyrimidin-4-amine) and E2-1.3 ((S*)-N-(1-(4-chlorophenethyl)-3,3-difluoropiperidin-4-yl)-1H-pyrazolo[3,4-d]pyrimidin-4-amine).

Results are shown in FIG. 2. Bars represent the mean±SEM immobility time for each dose group (n=10, \*\*\*/\*: different from vehicle group, p<0.001/0.05 respectively, One-way ANOVA, Dunnett's post-test). Doses are given as milligram per kilogram (mpk). The dose of imipramine was 32 mpk.

What is claimed is:
1. A chemical entity, which is a compound of formula I:

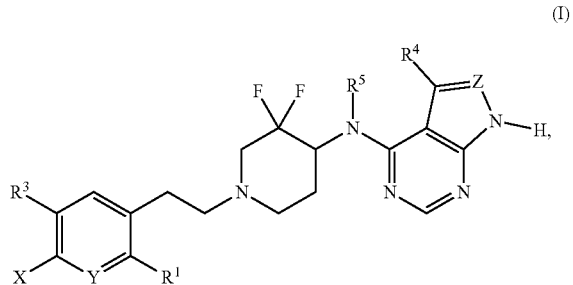

(I)

or a pharmaceutically acceptable salt thereof, wherein:
X is —H; halo; $C_1$-$C_6$ alkyl optionally substituted with 1 to 6 fluoro; $C_3$-$C_6$ cycloalkyl;
  $C_1$-$C_4$ alkoxy optionally substituted with 1 to 6 fluoro; —CN; —NO$_2$; —N(R$^7$)(R$^8$); —SR$^7$; —S(O)$_2$R$^6$; or —CO$_2$R$^7$;
Y is C(R$^2$) or N;
Z is C(H) or N;
R$^1$ is —H, halo, $C_1$-$C_4$ alkyl optionally substituted with 1 to 3 fluoro; $C_3$-$C_6$ cycloalkyl;
  $C_1$-$C_4$ alkoxy optionally substituted with 1 to 3 fluoro; —CN; —NO$_2$; —N(R$^7$)(R$^8$); —CO$_2$R$^7$; or —C(O)N(R$^7$)(R$^8$);
R$^2$ is —H; halo; $C_1$-$C_4$ alkyl optionally substituted with 1 to 3 fluoro; cyclopropyl; or $C_1$-$C_4$ alkoxy optionally substituted with 1 to 3 fluoro;
R$^3$ is —H, —F, —Cl, —CH$_3$, —CF$_3$ or —OCH$_3$;
R$^4$ is —H; —F; —Cl; $C_1$-$C_3$ alkyl optionally substituted with 1 to 3 fluoro; or cyclopropyl;
R$^5$ is —H or —CH$_3$;
each instance of R$^6$ independently is $C_1$-$C_4$ alkyl optionally substituted with 1 to 3 fluoro;
each instance of R$^7$ independently is $C_1$-$C_4$ alkyl; and
each instance of R$^8$ independently is —H or $C_1$-$C_4$ alkyl.
2. The chemical entity of claim 1, wherein:
X is —H; —F; —Cl; $C_1$-$C_4$ alkyl; $C_1$-$C_3$ alkyl substituted with 1 to 6 fluoro; cyclopropyl; $C_1$-$C_4$ alkoxy; $C_1$-$C_2$ alkoxy substituted with 1 to 3 fluoro; —CN; —NO$_2$; —N(R$^7$)(R$^8$); —SR$^7$; or —S(O)$_2$R$^6$;
Y is C(R$^2$) or N;
Z is C(H) or N;
R$^1$ is —H; —F; —Cl; $C_1$-$C_4$ alkyl; $C_1$-$C_2$ alkyl substituted with 1 to 3 fluoro; cyclopropyl; $C_1$-$C_4$ alkoxy; $C_1$-$C_2$ alkoxy substituted with 1 to 3 fluoro; —CN; —NO$_2$; —N(R$^7$)(R$^8$); —CO$_2$R$^7$; or —C(O)N(R$^7$)(R$^8$);
R$^2$ is —H; —F; —Cl; $C_1$-$C_4$ alkyl; $C_1$-$C_2$ alkyl substituted with 1 to 3 fluoro; cyclopropyl; $C_1$-$C_4$ alkoxy; $C_1$-$C_2$ alkoxy substituted with 1 to 3 fluoro;
R$^3$ is —H, —F, —Cl, —CH$_3$, —CF$_3$ or —OCH$_3$;
R$^4$ is —H, —F, —Cl, —CH$_3$, —CF$_3$, or cyclopropyl;
R$^5$ is —H or —CH$_3$;
each instance of R$^6$ independently is $C_1$-$C_2$ alkyl optionally substituted with 1 to 3 fluoro;
each instance of R$^7$ independently is $C_1$-$C_2$ alkyl; and
each instance of R$^8$ independently is —H or $C_1$-$C_2$ alkyl.
3. The chemical entity of claim 1, wherein:
X is —H; —F; —Cl; $C_1$-$C_2$ alkyl optionally substituted with 1 to 3 fluoro; or $C_1$-$C_2$ alkoxy optionally substituted with 1 to 3 fluoro;

Y is C(R²) or N;
Z is C(H) or N;
R¹ is —H, halo or —CH₃;
R² is —H, —F, —Cl or —CH₃;
R³ is —H, —F, —Cl, —CH₃ or —CF₃;
R⁴ is —H, —F, —CH₃ or —CF₃; and
R⁵ is —H or —CH₃.

4. The chemical entity of claim 1, wherein:
X is —H, —F, —Cl, —CH₃, —CH₂F, —CHF₂, —CF₃, —OCHF₂ or —OCF₃;
Y is C(R²) or N;
Z is C(H) or N;
R¹ is —H or —F;
R² is —H;
R³ is —H, —F or —CF₃;
R⁴ is —H or —CH₃; and
R⁵ is —H or —CH₃.

5. The chemical entity of claim 1 of formula (II):

(II)

[Structure]

6. The chemical entity of claim 5, wherein:
X is —H, —F, —Cl, —CH₃, —CH₂CH₃, —CH(CH₃)₂, —CF₃, —CH₂F, —CF₂CF₃, —CH(CF₃)₂, —CH₂CF₂CF₃, cyclopropyl, —OCH₃, —OCF₃, —OCHF₂, —OCFH₂, —CN, —NO₂, —N(CH₃)₂, —SCH₃, —SO₂CH₃ or —SO₂CF₃;
R¹ is —H, —F, —Cl, —CH₃, —CH₂CH₃, —CH(CH₃)₂, —CF₃, cyclopropyl, —OCH₃, —OCF₃, —OCHF₂, —OCFH₂, —CN, —NO₂, —CO₂CH₃, —CO₂CH₂CH₃, —C(O)N(CH₃)₂ or —C(O)NH(CH₃);
R³ is —H, —F, —Cl, —CH₃, —CF₃ or —OCH₃;
R⁴ is —H, —F; —Cl; C₁-C₃ alkyl optionally substituted with 1 to 3 fluoro; or cyclopropyl; and
R⁵ is —H or —CH₃.

7. The chemical entity of claim 5, wherein:
X is —H, —F, —Cl, —CH₃, —CH₂F, —CHF₂, —CF₃, —OCHF₂ or —OCF₃;
R¹ is —H or —F;
R³ is —H, —F or —CF₃;
R⁴ is —H or —CH₃; and
R⁵ is —H or —CH₃.

8. The chemical entity of claim 5 of formula (IIa):

(IIa)

[Structure]

9. The chemical entity of claim 1 of formula (III):

(III)

[Structure]

10. The chemical entity of claim 9, wherein:
X is —H, —F, —Cl, —CH₃, —CH₂CH₃, —CH(CH₃)₂, —CF₃, —CHF₂, —CH₂F, —CF₂CF₃, —CH(CF₃)₂, —CH₂CF₂CF₃, cyclopropyl, —OCH₃, —OCF₃, —OCHF₂, —OCFH₂, —CN, —NO₂, —N(CH₃)₂, —SCH₃, —SO₂CH₃ or —SO₂CF₃;
R¹ is —H, —F, —Cl, —CH₃, —CH₂CH₃, —CH(CH₃)₂, —CF₃, cyclopropyl, —OCH₃, —OCF₃, —OCHF₂, —OCFH₂, —CN, —NO₂, —CO₂CH₃, —CO₂CH₂CH₃, —C(O)N(CH₃)₂ or —C(O)NH(CH₃);
R³ is —H, —F, —Cl, —CH₃, —CF₃ or —OCH₃;
R⁴ is —H, —F; —Cl; C₁-C₃ alkyl optionally substituted with 1 to 3 fluoro; or cyclopropyl; and
R⁵ is —H or —CH₃.

11. The chemical entity of claim 9, wherein:
X is —H, —F, —Cl, —CH₃, —CH₂F, —CHF₂, —CF₃, —OCHF₂ or —OCF₃;
R¹ is —H or —F;
R³ is —H, —F or —CF₃;
R⁴ is —H or —CH₃; and
R⁵ is —H or —CH₃.

12. The chemical entity of claim 9 of formula (IIIa):

(IIIa)

[Structure]

13. The chemical entity of claim 1 of formula (IV):

(IV)

[Structure]

14. The chemical entity of claim 1 of formula (V):

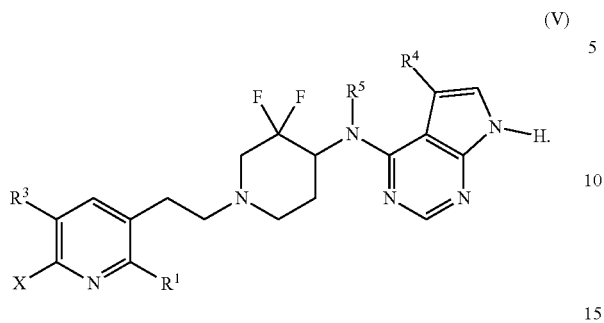

15. A pharmaceutical composition comprising the chemical entity claim 1 and a pharmaceutically acceptable carrier.

16. The pharmaceutical composition of claim 15, which is suitable for oral administration.

17. A method of treating a disease or disorder responsive to NR2B antagonism in a subject in need of such treatment, comprising administering an effective amount of the chemical entity of claim 1.

18. The method of claim 17, wherein the disease or disorder is depression, pain, Parkinson's disease, Huntington's disease, Alzheimer's disease, cerebral ischaemia, traumatic brain injury, epilepsy or migraine.

19. The method of claim 18, wherein the disease or disorder is depression.

* * * * *